US012569552B2

(12) United States Patent (10) Patent No.: US 12,569,552 B2

Torikai et al. (45) Date of Patent: Mar. 10, 2026

(54) FUSION PROTEIN OF PENTAMER AND gB OF CYTOMEGALOVIRUS, AND VACCINE CONTAINING SAID FUSION PROTEIN

(71) Applicant: KM Biologics Co., Ltd., Kumamoto (JP)

(72) Inventors: Masaharu Torikai, Kumamoto (JP); Hiroaki Mori, Kumamoto (JP); Kohsuke Hazeyama, Koshi (JP); Miyuki Matsumoto, Kikuyo-machi (JP)

(73) Assignee: KM Biologics Co., Ltd., Kumamoto (JP)

( * ) Notice: Subject to any disclaimer, the term of this patent is extended or adjusted under 35 U.S.C. 154(b) by 0 days.

(21) Appl. No.: 18/009,022

(22) PCT Filed: Jun. 8, 2021

(86) PCT No.: PCT/JP2021/021752
§ 371 (c)(1),
(2) Date: Dec. 8, 2022

(87) PCT Pub. No.: WO2021/251384
PCT Pub. Date: Dec. 16, 2021

(65) Prior Publication Data
US 2023/0248821 A1 Aug. 10, 2023

(30) Foreign Application Priority Data

Jun. 9, 2020 (JP) ................................. 2020-100100

(51) Int. Cl.
*A61K 39/245* (2006.01)
*A61K 39/00* (2006.01)
*A61P 37/04* (2006.01)
*C12N 15/63* (2006.01)

(52) U.S. Cl.
CPC ............ *A61K 39/245* (2013.01); *A61K 39/00* (2013.01); *A61P 37/04* (2018.01); *C12N 15/63* (2013.01)

(58) Field of Classification Search
None
See application file for complete search history.

(56) References Cited

U.S. PATENT DOCUMENTS

| | | | |
|---|---|---|---|
| 2008/0187545 A1 | 8/2008 | Shenk et al. | |
| 2013/0216613 A1* | 8/2013 | Baudoux ................ | A61K 39/12 |
| | | | 424/186.1 |
| 2015/0174237 A1 | 6/2015 | Mond et al. | |
| 2015/0322115 A1* | 11/2015 | Wellnitz ............... | C07K 14/005 |
| | | | 435/320.1 |
| 2016/0296619 A1 | 10/2016 | Orlinger et al. | |
| 2018/0057539 A1 | 3/2018 | Sodoyer et al. | |
| 2018/0265551 A1* | 9/2018 | Carfi ...................... | A61K 39/12 |

FOREIGN PATENT DOCUMENTS

| | | | |
|---|---|---|---|
| CN | 105980570 A | | 9/2016 |
| JP | 2017-515503 A | | 6/2017 |
| JP | 7271794 B2 | | 5/2023 |
| KR | 10-2015-0031322 A | | 3/2015 |
| KR | 10-2022-0062143 A | | 5/2022 |
| WO | 03/004647 A1 | | 1/2003 |
| WO | WO/13/006838 | * | 1/2013 |
| WO | 2014/005959 A1 | | 1/2014 |
| WO | 2015/165480 A1 | | 11/2015 |
| WO | 2015/170287 A1 | | 11/2015 |
| WO | 2017/153954 A1 | | 9/2017 |
| WO | 2020/085457 A1 | | 4/2020 |
| WO | 2020/121983 A1 | | 6/2020 |
| WO | 2021/251384 A1 | | 12/2021 |

OTHER PUBLICATIONS

Azuma et al., "Cytomegalovirus seropositivity in pregnant women in Japan during 1996-2009," Journal of Japan Society of Perinatal and Neonatal Medicine, 46: 1273-1279 (2010) (see English abstract).

Stratton et al., "Vaccines for the 21st century : a tool for decision making," The National Academies Press, (2000).

Revello et al., "Randomized trial of hyperimmune globulin to prevent congenital cytomegalovirus," New England Journal of Medicine, 370: 1316-1326 (2014).

Rieder et al., "Cytomegalovirus vaccine: phase II clinical trial results," Clinical Microbiology and Infection, 20 Suppl 5: 95-102 (2014).

Yamada et al., "Characterization of the guinea pig cytomegalovirus genome locus that encodes homologs of human cytomegalovirus major immediate early genes, UL128, and UL130," Virology, 391: 99-106 (2009).

Schleiss et al., "Glycoprotein B (gB) vaccines adjuvanted with AS01 or AS02 protect female guinea pigs against cytomegalovirus (CMV) viremia and offspring mortality in a CMV-challenge model," Vaccine 32: 2756-2762 (2014).

Hashimoto et al., "Effects of immunization of pregnant guinea pigs with guinea pig cytomegalovirus glycoprotein B on viral spread in the placenta," Vaccine, 31: 3199-3205 (2013).

Coleman et al., "A Homolog Pentameric Complex Dictates Viral Epithelial Tropism, Pathogenicity and Congenital Infection Rate in Guinea Pig Cytomegalovirus," PLoS Pathogens, 12: e1005755 (2016).

Zydek et al., "HCMV Infection of Human Trophoblast Progenitor Cells of the Placenta Is Neutralized by a Human Monoclonal Antibody to Glycoprotein B and Not by Antibodies to the Pentamer Complex," Viruses, 6: 1346-1364 (2014).

(Continued)

*Primary Examiner* — Benjamin P Blumel
(74) *Attorney, Agent, or Firm* — Morgan, Lewis & Bockius LLP

(57) ABSTRACT

An object of the present invention is to provide an effective vaccine that can prevent and treat infection with CMV. A fusion protein of the present invention is a fusion protein of envelope glycoprotein B (gB protein) and a pentamer of the cytomegalovirus (CMV). A vaccine for prevent or treat infection with cytomegalovirus (CMV) of the present invention is a subunit vaccine containing a fusion protein of envelope glycoprotein B (gB protein) and a pentamer of CMV as an antigen.

23 Claims, 32 Drawing Sheets

Specification includes a Sequence Listing.

(56)         References Cited

OTHER PUBLICATIONS

Yamada et al., "An Ex vivo culture model for placental cytomegalovirus infection using slices of Guinea pig placental tissue," Placenta, 37: 85-88 (2016).

Patel et al., "In Vitro Characterization of Human Cytomegalovirus-Targeting Therapeutic Monoclonal Antibodies LJP538 and LJP539," Antimicrobial Agents and Chemotherapy, 60: 4961-4971 (2016).

Burke et al., "Crystal Structure of the Human Cytomegalovirus Glycoprotein B," PLoS Pathogens, 11: e1005227 (2015).

Ciferri et al., "Structural and biochemical studies of HCMV gH/gL/gO and Pentamer reveal mutually exclusive cell entry complexes," PNAS, 112: 1767-1772 (2015).

Chandramouli et al., "Structural basis for potent antibody-mediated neutralization of human cytomegalovirus," Science Immunology, 2: eaan1457 (2017).

Chiuppesi et al., "Vaccine-Derived Neutralizing Antibodies to the Human Cytomegalovirus gH/gL Pentamer Potently Block Primary Cytotrophoblast Infection," Journal of Virology, 89 (23): 11884-11898 (2015).

International Search Report issued in corresponding International Patent Application No. PCT/JP2021/021752 dated Aug. 17, 2021.

International Preliminary Report on Patentability and Written Opinion issued in corresponding International Patent Application No. PCT/JP2021/021752 dated Dec. 22, 2022.

Notice of Reasons for Rejection issued in Japanese Patent Application No. 2022-530580 dated Sep. 27, 2022.

Notice of Reasons for Rejection issued in Japanese Patent Application No. 2022-530580 dated Jan. 17, 2023.

Decision to Grant issued in Japanese Patent Application No. 2022-530580 dated Apr. 18, 2023.

Extended European Search Report issued in European Patent Application No. 21822804.7 dated Feb. 9, 2024.

* cited by examiner

*Fig.1*
(a) N-UL128-gB
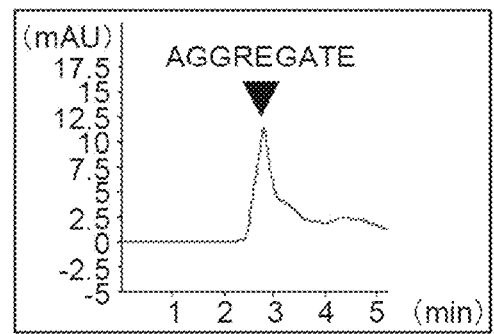
(b) N-UL130-gB
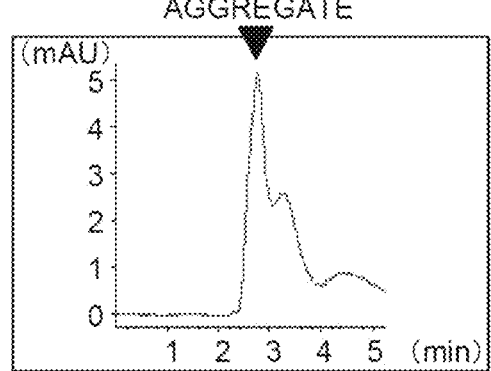
(c) N-UL131-gB
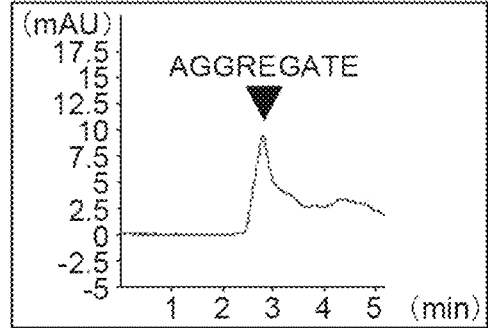
(d) N-UL128-gB/N-UL130-gB/N-UL131-gB
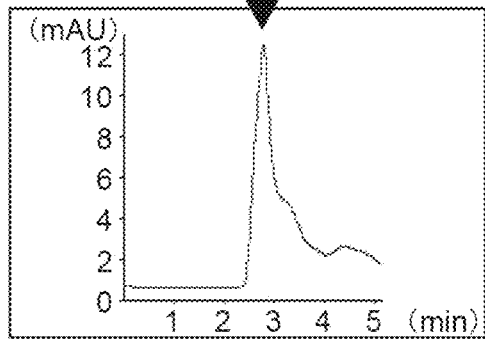

*Fig.2*
(a) C-UL128-gB
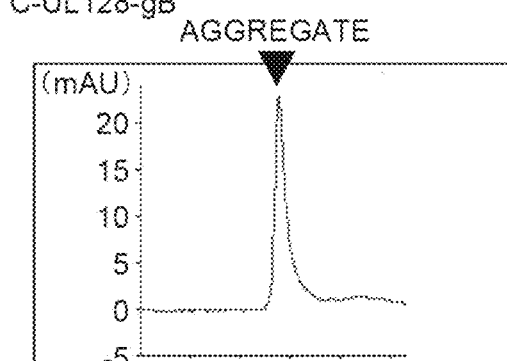
(b) C-UL130-gB
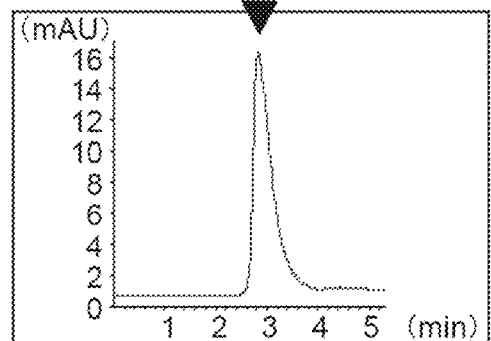
(c) C-UL131-gB
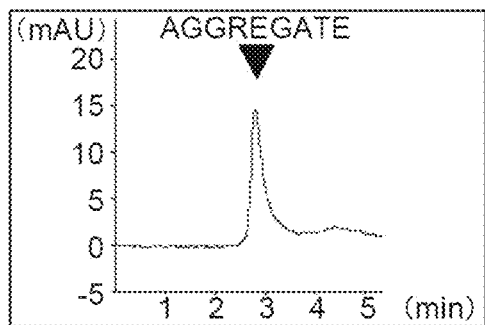
(d) C-UL128-gB/C-UL130-gB/C-UL131-gB
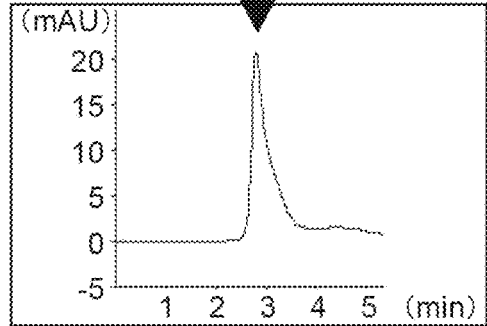

*Fig.3*
(a) Δd4-UL128-gB
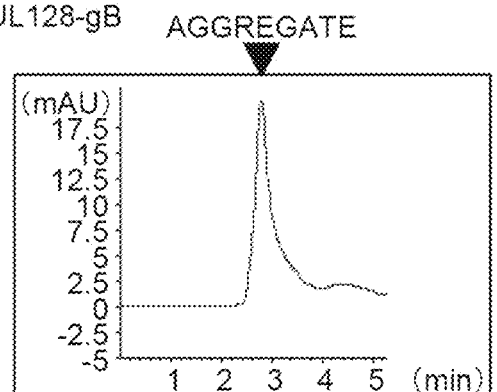
(b) Δd4-UL130-gB
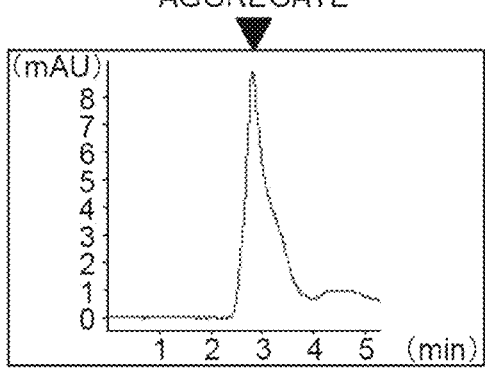
(c) Δd4-UL131-gB
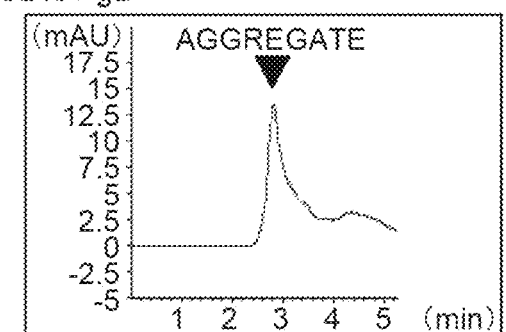
(d) Δd4-UL128-gB/Δd4-UL130-gB/Δd4-UL131-gB
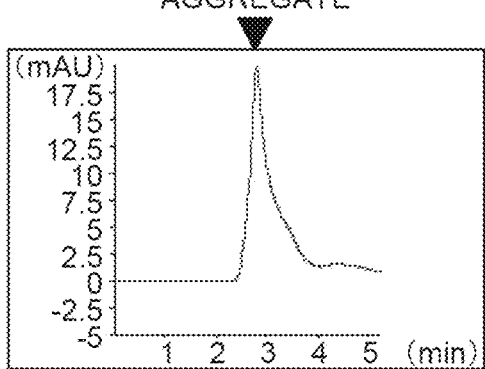

1: N-UL128-gB/N-UL130-gB/N-UL131-gB

2: UL128(C162S)-gB/N-UL130-gB/N-UL131-gB

3: UL128(C162S)-VC37/UL130-VC37/UL131-VC37

4: UL128(C162S)-Δd4/UL130-Δd4/UL131-Δd4

5: PENTAMER

6: gBv9

*Fig.5*
(a) UL128(C162S)-Δd4/UL130-Δd4/UL131-Δd4
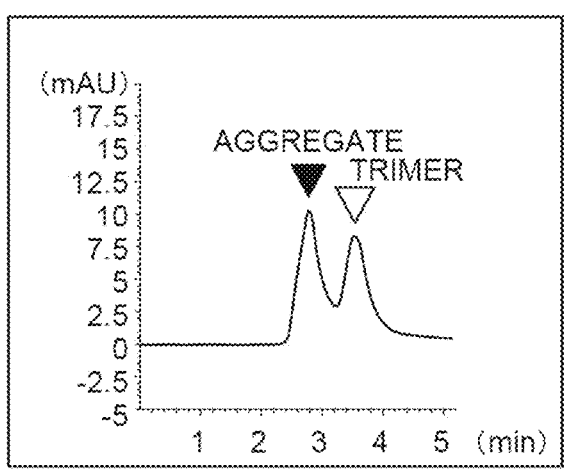
(b) UL128-Δd4/UL130-Δd4/UL131-Δd4
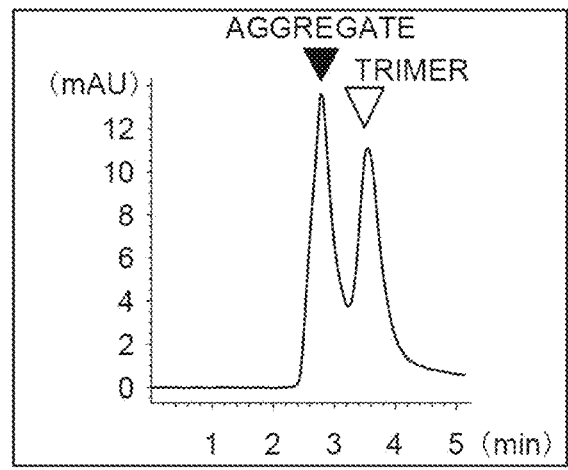

CULTURE SUPERNATANT

1: UL128(C162S)-VC37/UL130-VC37/UL131-VC37

2: UL128(C162S)-VC37/UL130/UL131

3: gH(His-)/gL(C144S)/UL128(C162S)-VC37/UL130-VC37/UL131-VC37

4: gH(His-)/gL/UL128/UL130-VC37/UL131

5: PENTAMER

6: gBv9

7: gBVC37

CULTURE SUPERNATANT

Legend:
☐ PENTAMER IMMUNE SERUM    ☐ gB IMMUNE SERUM    ☒ SALINE IMMUNE SERUM

1: UL128(C162S)-Δd4/UL130-Δd4/UL131-Δd4

2: UL128(C162S)-Δd4/UL130/UL131

3: gH(His-)/gL(C144S)/UL128(C162S)-Δd4/UL130-Δd4/UL131-Δd4

4: gH(His-)/gL/UL128/UL130-Δd4/UL131

5: PENTAMER

6: gBv9

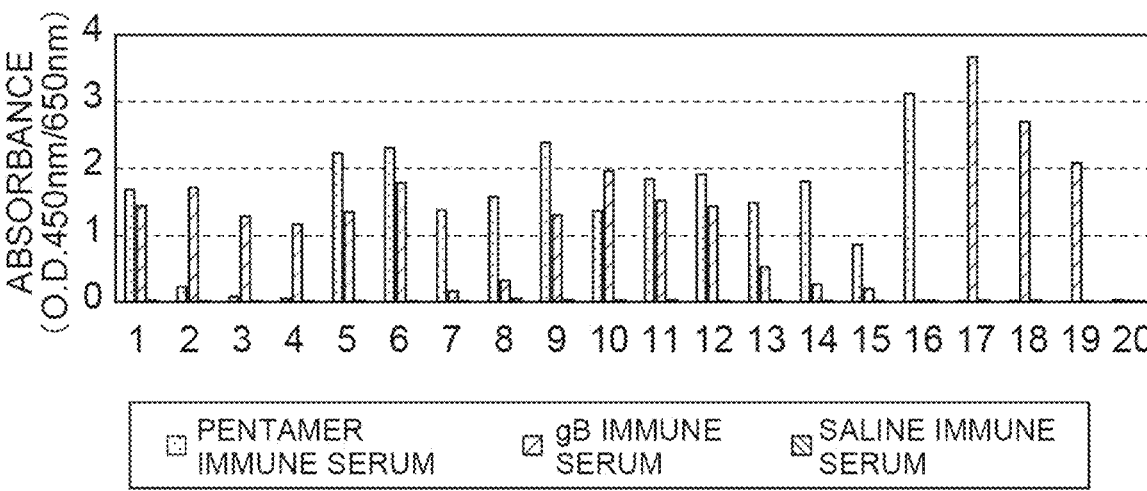

CULTURE SUPERNATANT

□ PENTAMER IMMUNE SERUM          ☑ gB IMMUNE SERUM          ▨ SALINE IMMUNE SERUM

1: UL128(C162S)-Δd4/UL130-Δd4/UL131-Δd4

2: UL128(C162S)-Δd4/UL130/UL131/Δd4

3: UL128(C162S)/UL130-Δd4/UL131/Δd4

4: UL128(C162S)/UL130/UL131-Δd4/Δd4

5: gH(His-)/gL/UL128/UL130-VC37/UL131/VC37

6: gH(His-)/gL/UL128/UL130/UL131-VC37/VC37

7: gH(His-)/gL/UL128/UL130-VC37/UL131

8: gH(His-)/gL/UL128/UL130/UL131-VC37

9: gH(His-)/gL(C144S)/UL128(C162S)-Δd4/UL130-Δd4/UL131-Δd4

10: gH(His-)/gL(C144S)/UL128(C162S)-Δd4/UL130/UL131/Δd4

11: gH(His-)/gL/UL128/UL130-Δd4/UL131/Δd4

12: gH(His-)/gL/UL128/UL130/UL131-Δd4/Δd4

13: gH(His-)/gL(C144S)/UL128(C162S)-Δd4/UL130/UL131

14: gH(His-)/gL/UL128/UL130-Δd4/UL131

15: gH(His-)/gL/UL128/UL130/UL131-Δd4

16: PENTAMER

17: gBv9

18: gBVC37

19: gBΔd4

20: BUFFER

CULTURE SUPERNATANT

1: gH(His-)/gL-VC37-L15aa/UL128-VC37-L15aa/UL130-VC37-L15aa/UL131

2: gH(His-)/gL-VC37-L15aa/UL128-VC37-L15aa/UL130/UL131-VC37-L15aa

3: gH(His-)/gL-VC37-L15aa/UL128/UL130-VC37-L15aa/UL131-VC37-L15aa

4: gH(His-)/gL-Δd4/UL128(C162S)-Δd4/UL130-Δd4/UL131

5: gH(His-)/gL-Δd4/UL128(C162S)-Δd4/UL130/UL131-Δd4

6: gH(His-)/gL-Δd4/UL128/UL130-Δd4/UL131-Δd4

7: UL128-VC37-L15aa/UL130-VC37-L15aa/UL131-VC37-L15aa

8: PENTAMER

9: VC37

10: gBΔd4

*Fig.10*
(a) gH(His-)/gL/UL128/UL130-VC37/UL131/VC37
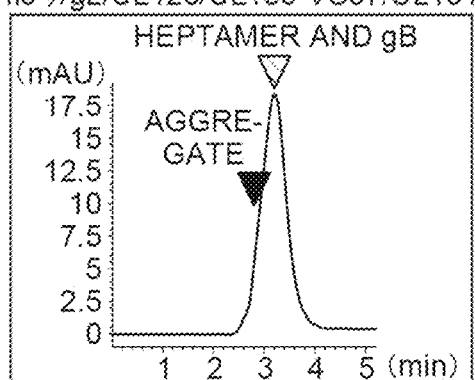
(b) gH(His-)/gL/UL128/UL130/UL131-VC37/VC37
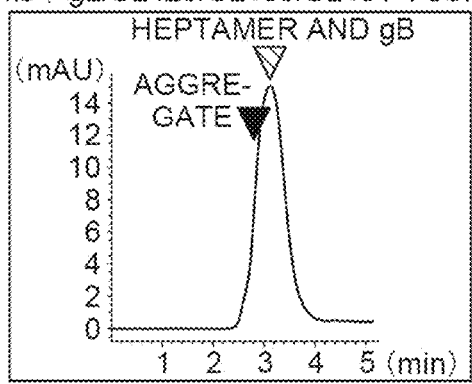
(c) gH(His-)/gL/UL128/UL130-Δd4/UL131/Δd4
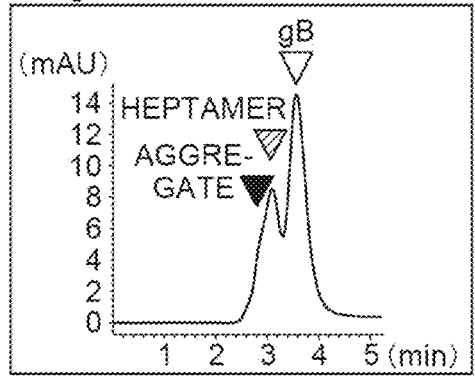
(d) gH(His-)/gL/UL128/UL130/UL131-Δd4/Δd4
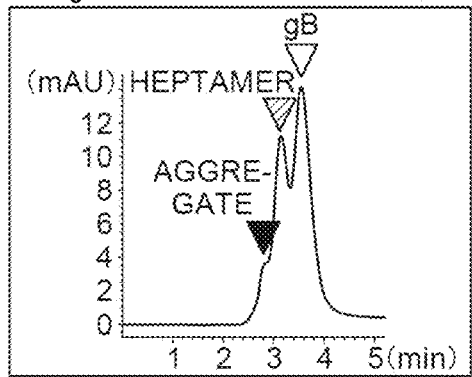

*Fig.11*   (a) gH(His-)/gL(C144S)/UL128(C162S)-Δd4/UL130-Δd4/UL131-Δd4
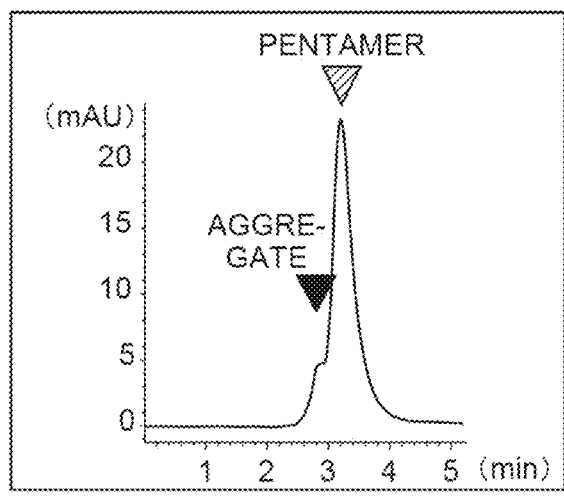
(b) gH(His-)/gL/UL128/UL130-Δd4/UL131
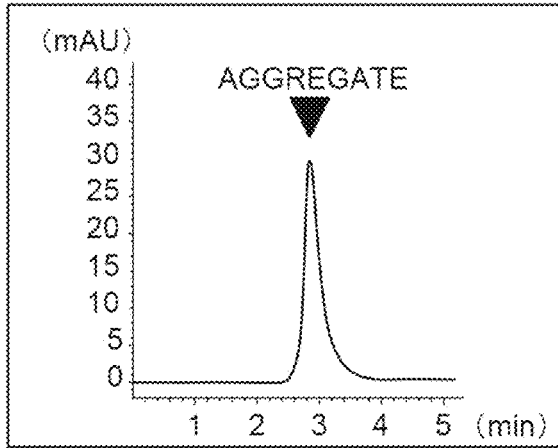
(c) UL128(C162S)-Δd4/UL130-Δd4/UL131-Δd4
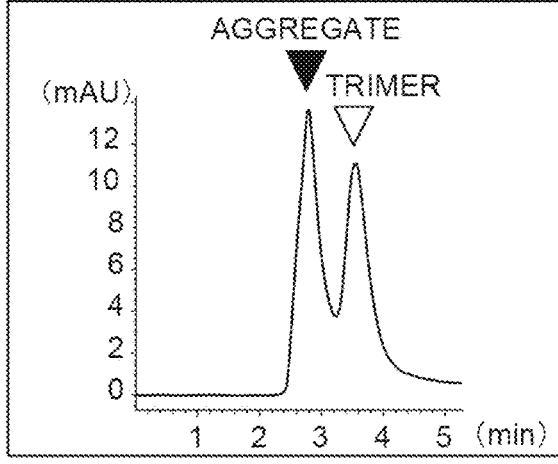

*Fig.12*   (a) gH(His-)/gL-VC37-L15aa/UL128-VC37-L15aa/UL130-VC37-L15aa/UL131
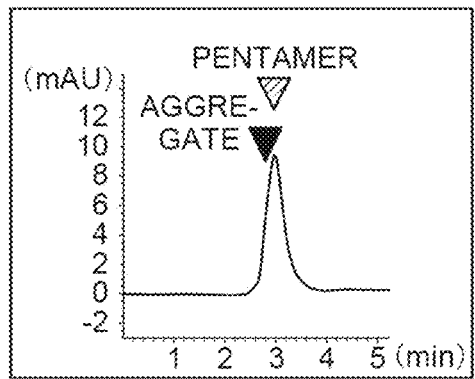
(b) gH(His-)/gL-VC37-L15aa/UL128-VC37-L15aa/UL130/UL131-VC37-L15aa
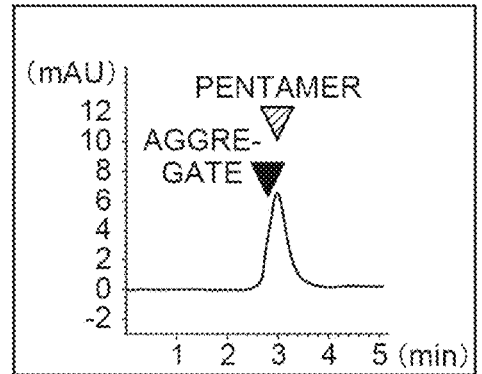
(c) gH(His-)/gL-VC37-L15aa/UL128/UL130-VC37-L15aa/UL131-VC37-L15aa
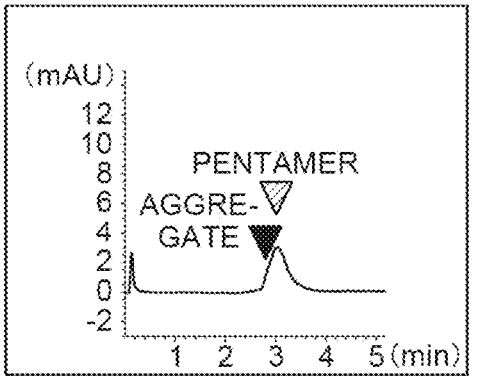
(d) gH(His-)/gL-Δd4/UL128(C162S)-Δd4/UL130-Δd4/UL131
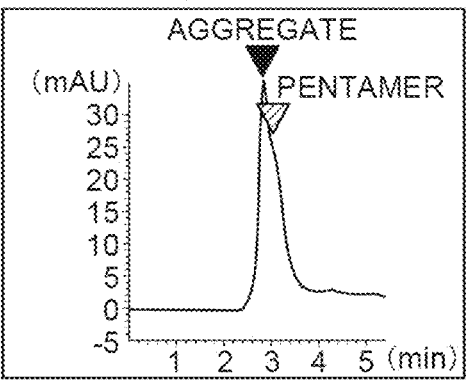

*Fig.13*
(a) gH(His-)/gL-Δd4/UL128(C162S)-Δd4/UL130/UL131-Δd4
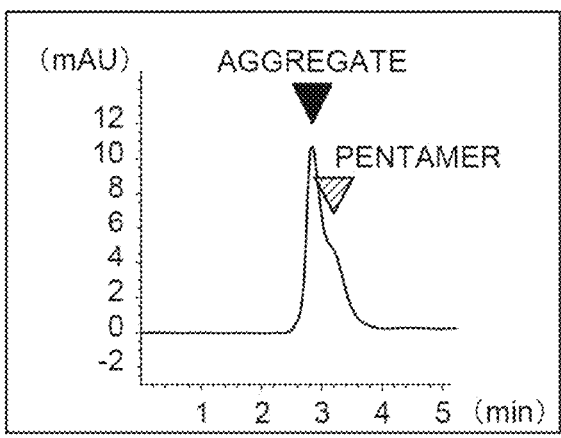
(b) gH(His-)/gL-Δd4/UL128/UL130-Δd4/UL131-Δd4
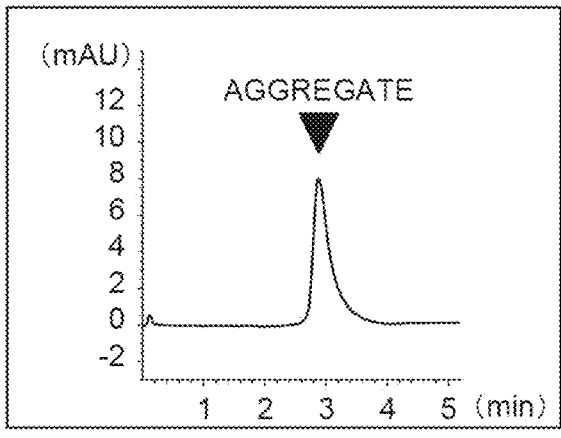

*Fig.14*
(a)
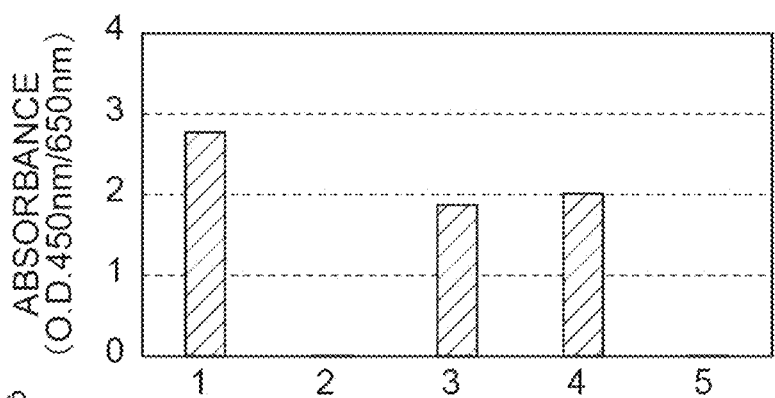
ANTI-gB ANTIBODY TITER (1/12800)
1: gBv9
2: PENTAMER
3: gH(His-)/gL-VC37-L15aa/UL128-VC37-L15aa/UL130/UL131-VC37-L15aa
4: gH(His-)/gL-Δd4/UL128(C162S)-Δd4/UL130-Δd4/UL131
5: saline
(b)
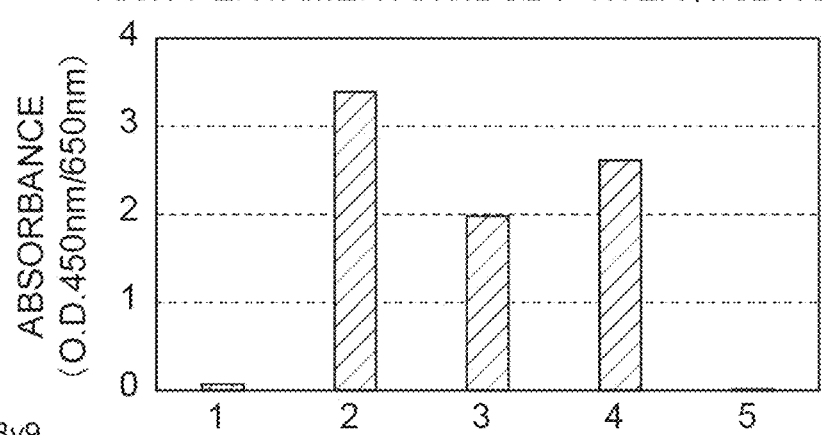
ANTI-PENTAMER ANTIBODY TITER (1/32000)
1: gBv9
2: PENTAMER
3: gH(His-)/gL-VC37-L15aa/UL128-VC37-L15aa/UL130/UL131-VC37-L15aa
4: gH(His-)/gL-Δd4/UL128(C162S)-Δd4/UL130-Δd4/UL131
5: saline

*Fig.15*
(a)
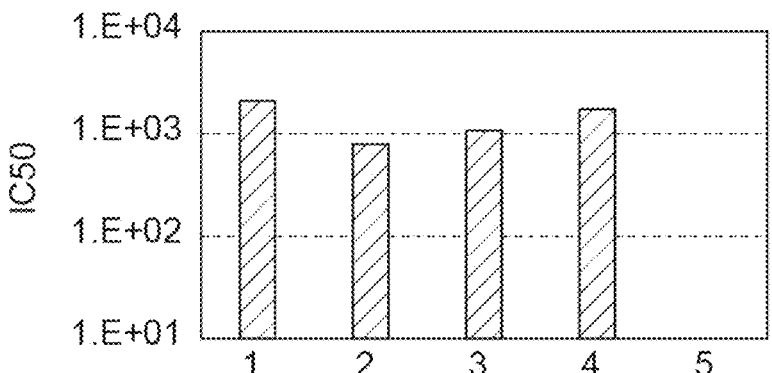
NEUTRALIZATION ACTIVITY TO MRC-5
1: gBv9
2: PENTAMER
3: gH(His-)/gL-VC37-L15aa/UL128-VC37-L15aa/UL130/UL131-VC37-L15aa
4: gH(His-)/gL-Δd4/UL128(C162S)-Δd4/UL130-Δd4/UL131
5: saline
(b)
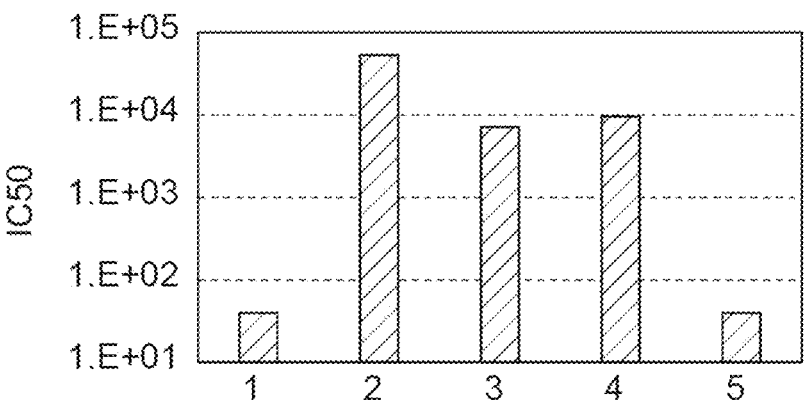
NEUTRALIZATION ACTIVITY TO ARPE-19
1: gBv9
2: PENTAMER
3: gH(His-)/gL-VC37-L15aa/UL128-VC37-L15aa/UL130/UL131-VC37-L15aa
4: gH(His-)/gL-Δd4/UL128(C162S)-Δd4/UL130-Δd4/UL131
5: saline

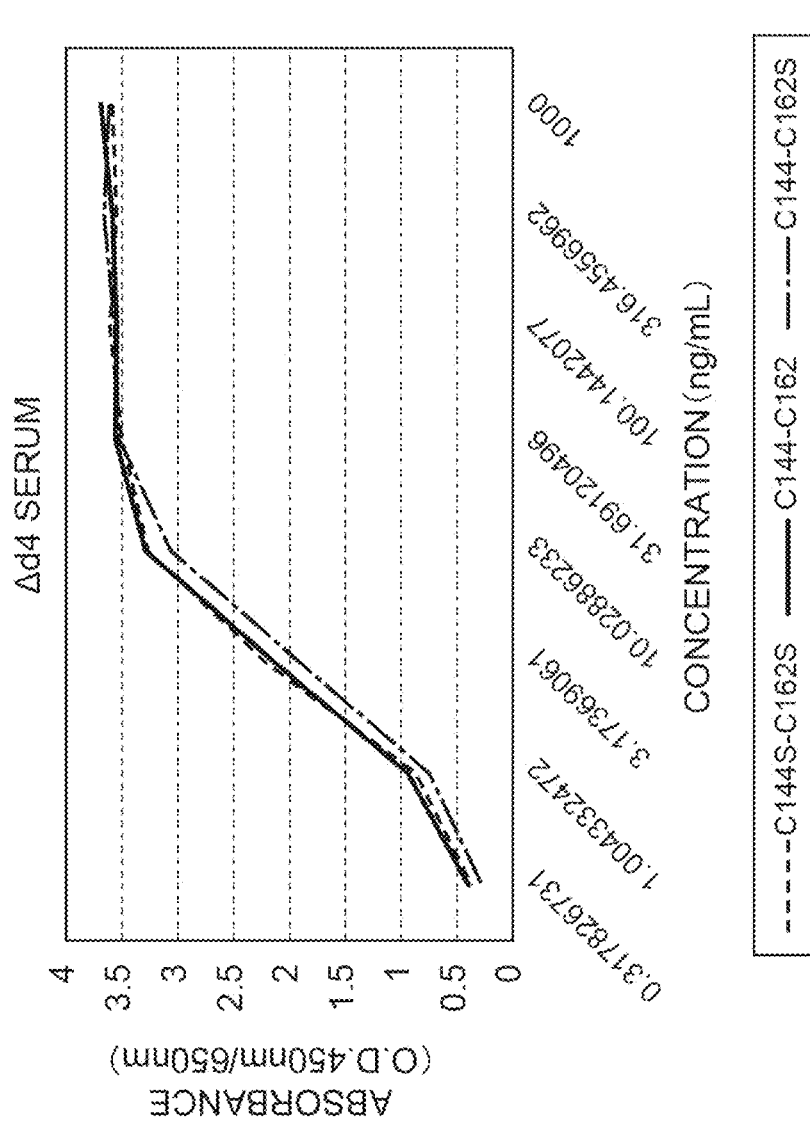
*Fig.16*

C144S-C162S: gH(His-)/gL(C144S)-Δd4/UL128(C162S)-Δd4/UL130-Δd4/UL131

C144-C162: gH(His-)/gL-Δd4/UL128-Δd4 /UL130-Δd4/UL131

C144-C162S: gH(His-)/gL-Δd4/UL128(C162S)-Δd4/UL130-Δd4/UL131

*Fig.20*
(a) gH(His-)/gL-Δd4/UL128-Δd4 /UL130-Δd4/UL131
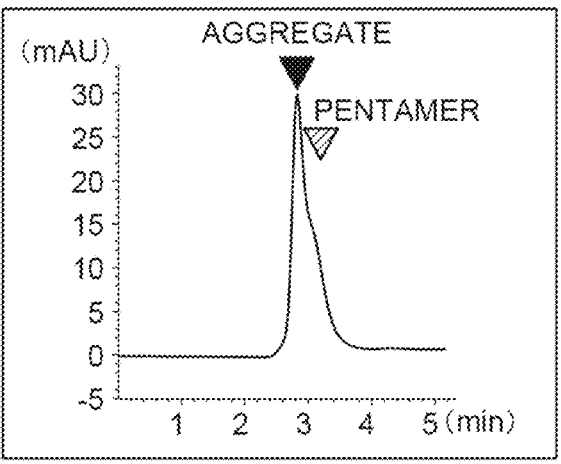
(b) gH(His-)/gL(C144S)-Δd4/UL128(C162S)-Δd4/UL130-Δd4/UL131
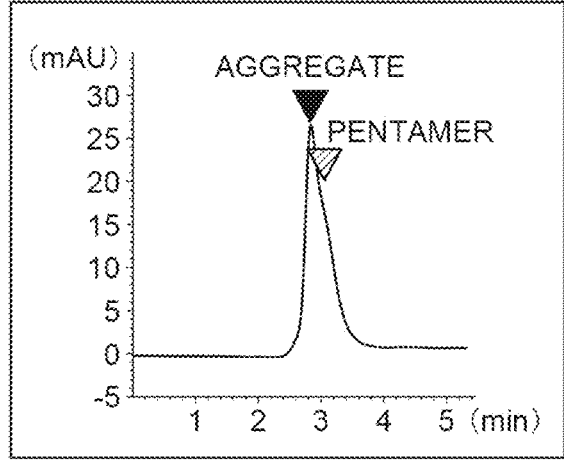

Fig.21

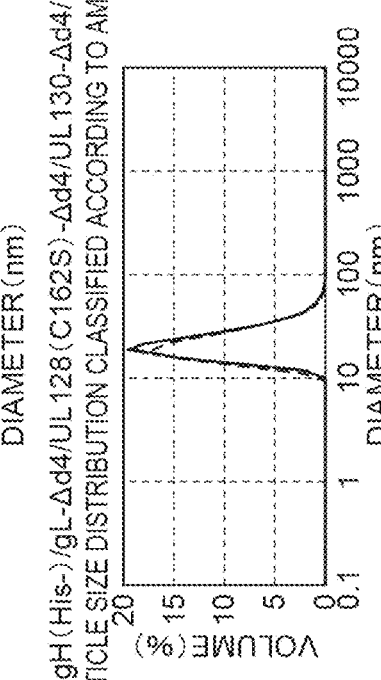

(a) gH(His-)/gL-Δd4/UL128-Δd4/UL130-Δd4/UL131
PARTICLE SIZE DISTRIBUTION CLASSIFIED ACCORDING TO AMOUNT

|  | DIAMETER (nm) | VOLUME (%) | WIDTH (nm) |
|---|---|---|---|
| PEAK 1 | 23.09 | 99.5 | 9.519 |
| PEAK 2 | 308.3 | 0.5 | 135.5 |
| PEAK 3 | 0 | 0 | 0 |

(b) gH(His-)/gL(C144S)-Δd4/UL128(C162S)-Δd4/UL130-Δd4/UL131
PARTICLE SIZE DISTRIBUTION CLASSIFIED ACCORDING TO AMOUNT

|  | DIAMETER (nm) | VOLUME (%) | WIDTH (nm) |
|---|---|---|---|
| PEAK 1 | 22.94 | 99.6 | 10.39 |
| PEAK 2 | 363.1 | 0.4 | 160.7 |
| PEAK 3 | 0 | 0 | 0 |

(c) gH(His-)/gL-Δd4/UL128(C162S)-Δd4/UL130-Δd4/UL131
PARTICLE SIZE DISTRIBUTION CLASSIFIED ACCORDING TO AMOUNT

|  | DIAMETER (nm) | VOLUME (%) | WIDTH (nm) |
|---|---|---|---|
| PEAK 1 | 22.86 | 98.8 | 11.15 |
| PEAK 2 | 434.3 | 1.2 | 239.4 |
| PEAK 3 | 0 | 0 | 0 |

*Fig.22*
(a) gBv9
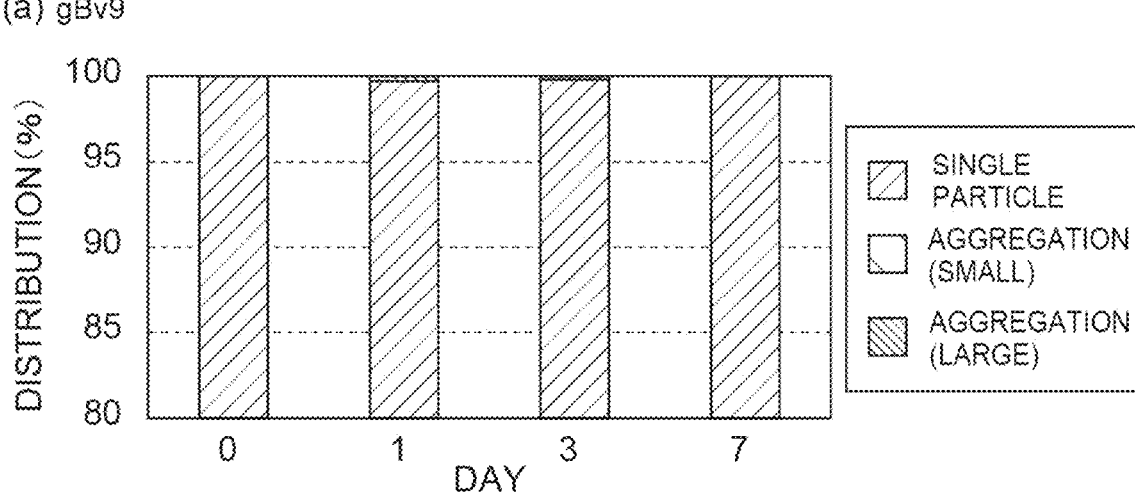
(b) PENTAMER
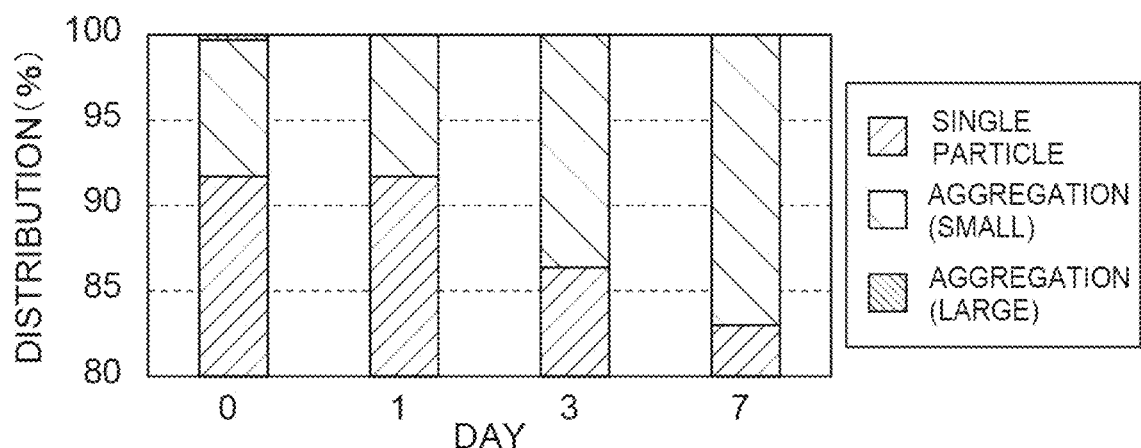

*Fig.23*
(a) gH(His-)/gL-Δd4/UL128(C162S)-Δd4/UL130-Δd4/UL131
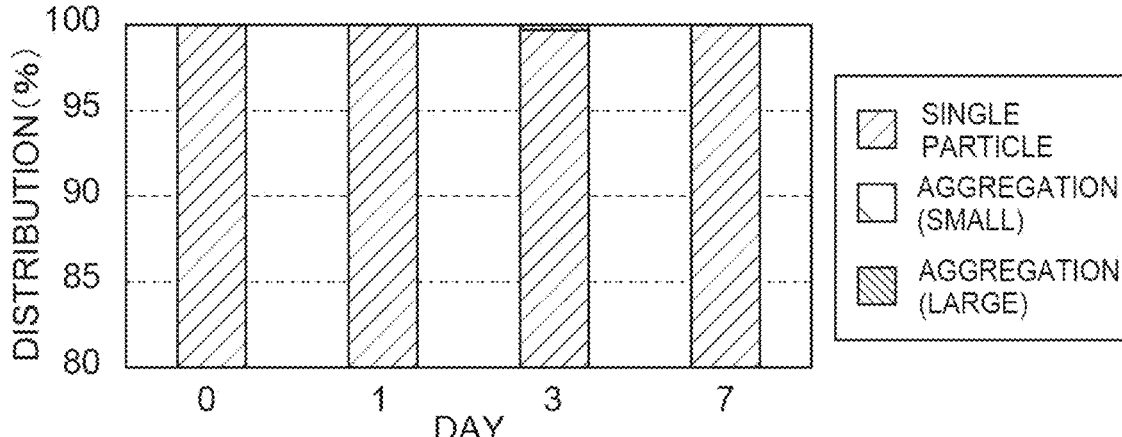
(b) gH(His-)/gL/UL128(C162S)-Δd4/UL130-Δd4/UL131-Δd4
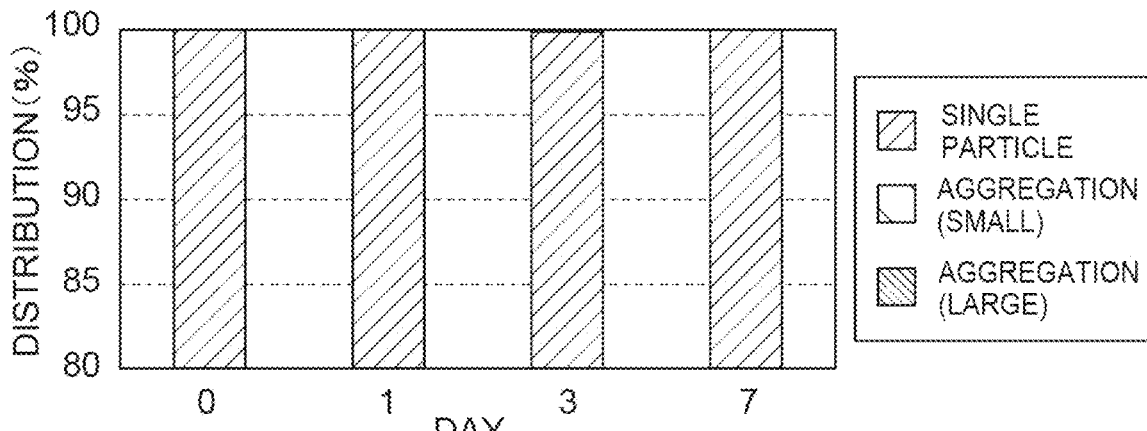
(c) gH(His-)/gL/UL128-Δd4/UL130-Δd4/UL131-Δd4
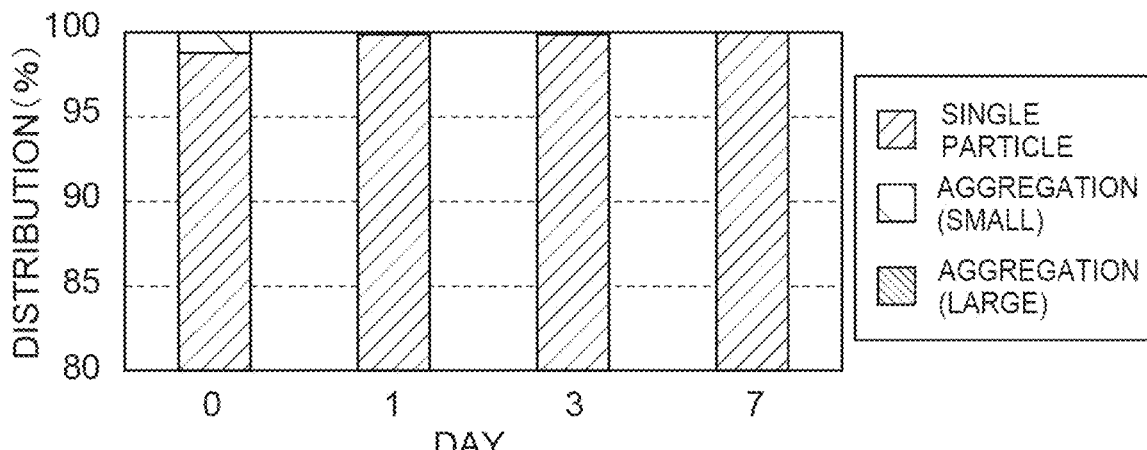

1: gBv9

2: PENTAMER

3: gH(His-)/gL-Δd4/UL128(C162S)-Δd4/UL130-Δd4/UL131

4: gH(His-)/gL-Δd4/UL128-Δd4/UL130-Δd4/UL131

5: gH(His-)/gL/UL128-Δd4/UL130-Δd4/UL131-Δd4

6: NEGATIVE CONTROL

*Fig.25*     (a) GP75(His-)/GP115-Δd4/GP129-Δd4/GP131-Δd4/GP133
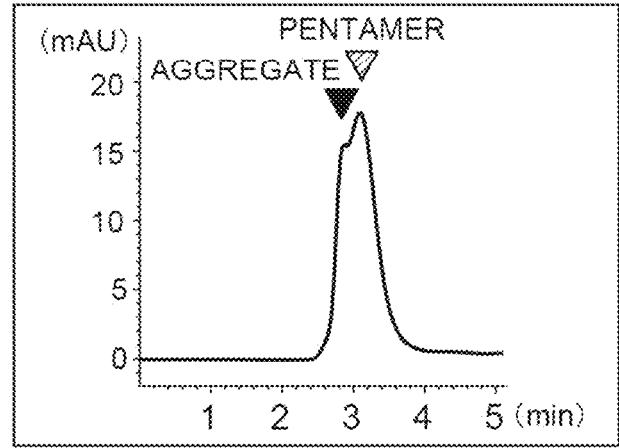
(b) GP75(His-)/GP115/GP129-Δd4/GP131-Δd4/GP133-Δd4
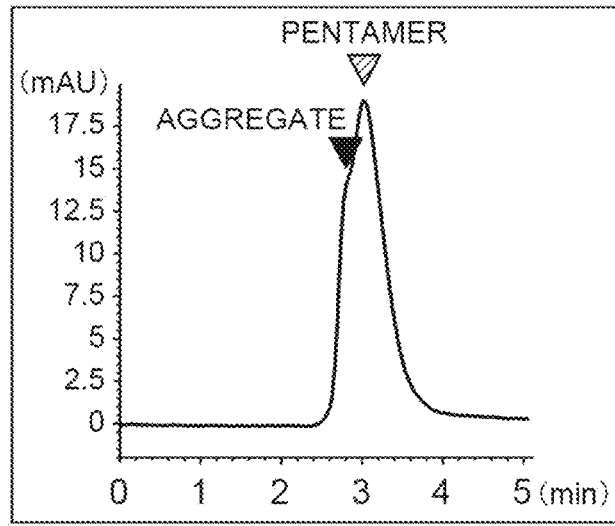
(c) GP129(C167S)-Δd4/GP131-Δd4/GP133-Δd4
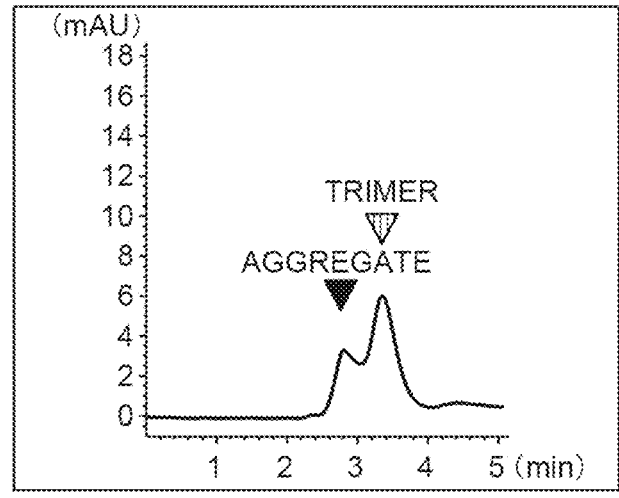

1. GPCMV-gB
2. GPCMV PENTAMER
3. GPCMV-gB+GPCMV PENTAMER
4. GP75(His-)/GP115-Δd4/GP129-Δd4/GP131-Δd4/GP133
5. GP75(His-)/GP115/GP129-Δd4/GP131-Δd4/GP133-Δd4
6. saline

|  | MOTHER'S BODY | | | | | | PLACENTA | | | | | | FETUS (PANCREAS) | | | | | |
|---|---|---|---|---|---|---|---|---|---|---|---|---|---|---|---|---|---|---|
|  | 1 | 2 | 3 | 4 | 5 | 6 | 1 | 2 | 3 | 4 | 5 | 6 | 1 | 2 | 3 | 4 | 5 | 6 |
| THE NUMBER OF INFECTIONS | 6 | 6 | 6 | 6 | 6 | 17 | 4 | 3 | 6 | 1 | 2 | 58 | 3 | 6 | 2 | 0 | 0 | 41 |
| THE NUMBER OF SPECIMENS | 6 | 6 | 6 | 6 | 6 | 18 | 17 | 21 | 21 | 19 | 17 | 60 | 17 | 21 | 21 | 19 | 17 | 60 |
| INFECTION RATE | 100% | 100% | 100% | 100% | 100% | 94% | 24% | 14% | 29% | 5% | 12% | 97% | 18% | 29% | 10% | 0% | 0% | 68% |

*Fig.28*
(a) gH(His-)/gL/UL128(C162S)-Δd4/UL130-Δd4/UL131-Δd4
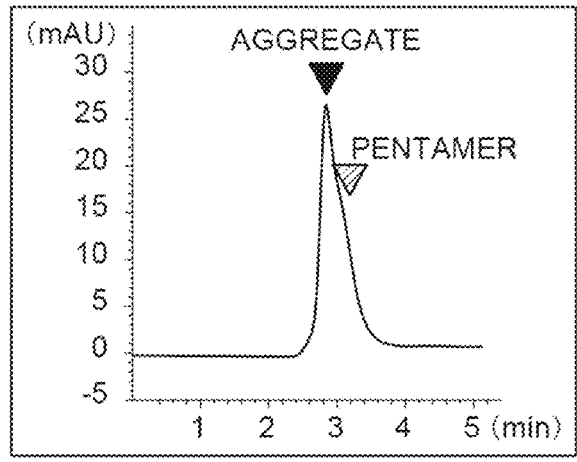
(b) gH(His-)/gL/UL128-Δd4/UL130-Δd4/UL131-Δd4
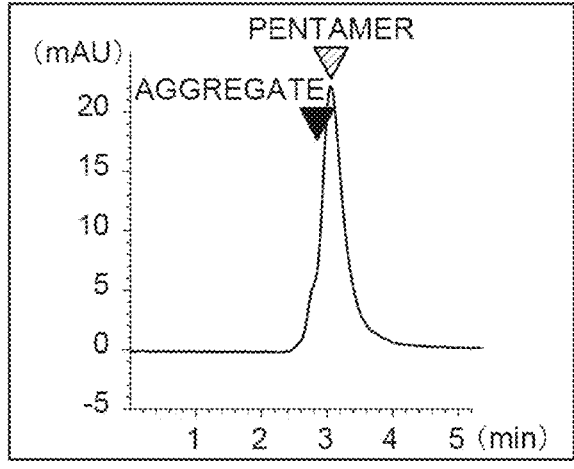

Fig.29

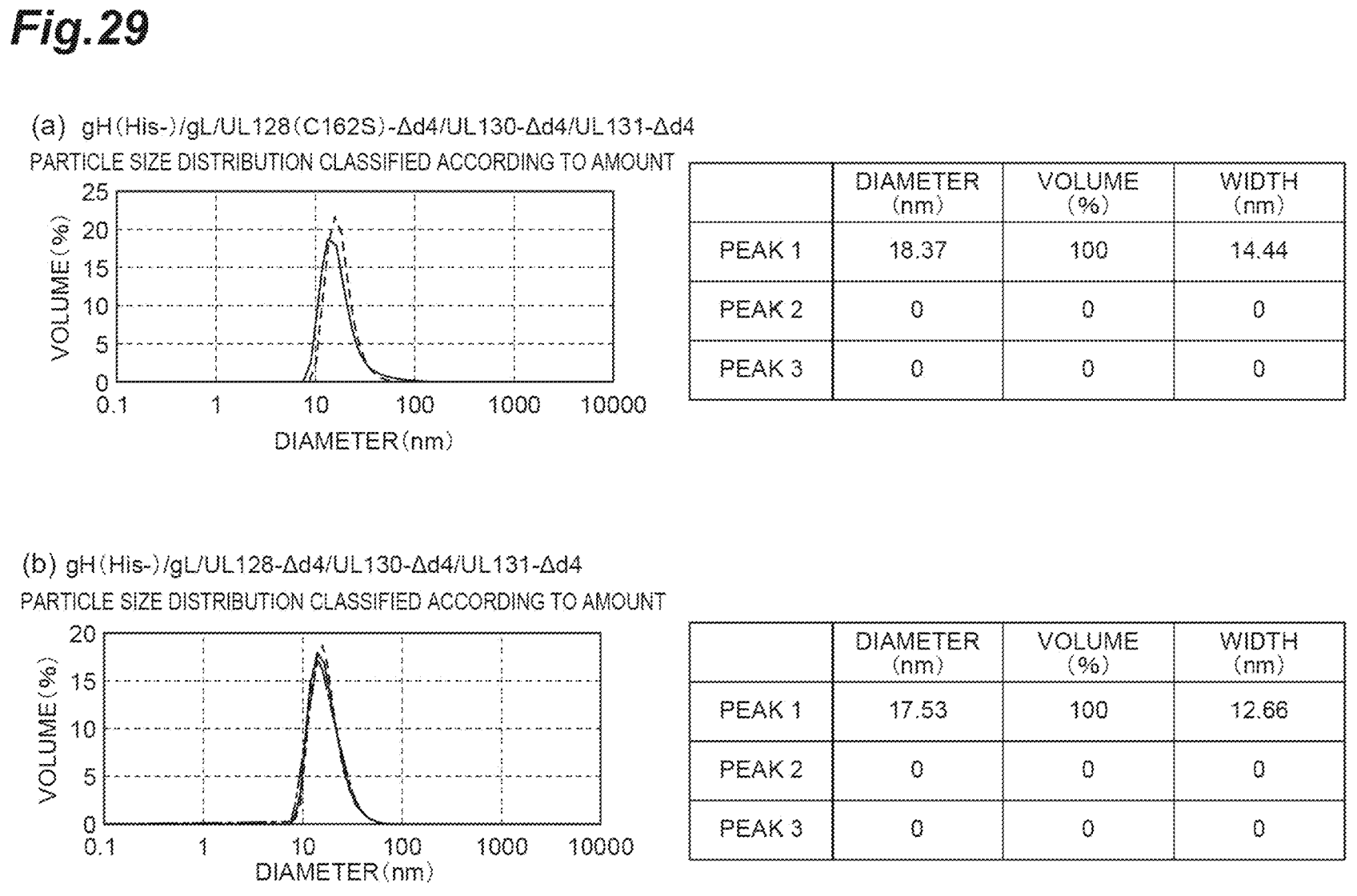

(a) gH(His-)/gL/UL128(C162S)-Δd4/UL130-Δd4/UL131-Δd4
PARTICLE SIZE DISTRIBUTION CLASSIFIED ACCORDING TO AMOUNT

| | DIAMETER (nm) | VOLUME (%) | WIDTH (nm) |
|---|---|---|---|
| PEAK 1 | 18.37 | 100 | 14.44 |
| PEAK 2 | 0 | 0 | 0 |
| PEAK 3 | 0 | 0 | 0 |

(b) gH(His-)/gL/UL128-Δd4/UL130-Δd4/UL131-Δd4
PARTICLE SIZE DISTRIBUTION CLASSIFIED ACCORDING TO AMOUNT

| | DIAMETER (nm) | VOLUME (%) | WIDTH (nm) |
|---|---|---|---|
| PEAK 1 | 17.53 | 100 | 12.66 |
| PEAK 2 | 0 | 0 | 0 |
| PEAK 3 | 0 | 0 | 0 |

*Fig.30*
(a)
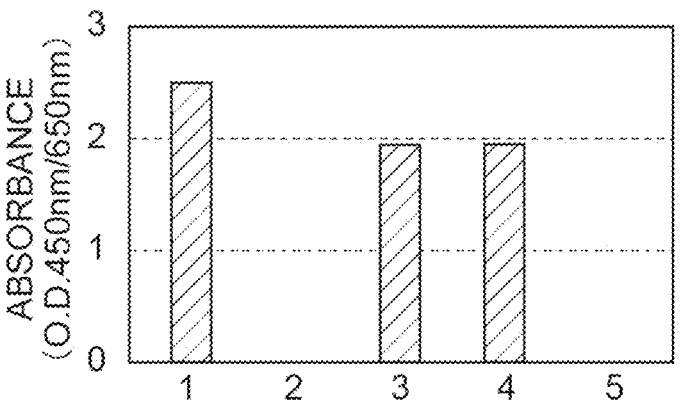
ANTI-gB ANTIBODY TITER(1/32000)
1.gBv9
2.PENTAMER
3.gH(His-)/gL-Δd4/UL128-Δd4/UL130-Δd4/UL131
4.gH(His-)/gL/UL128-Δd4/UL130-Δd4/UL131-Δd4
5.saline
(b)
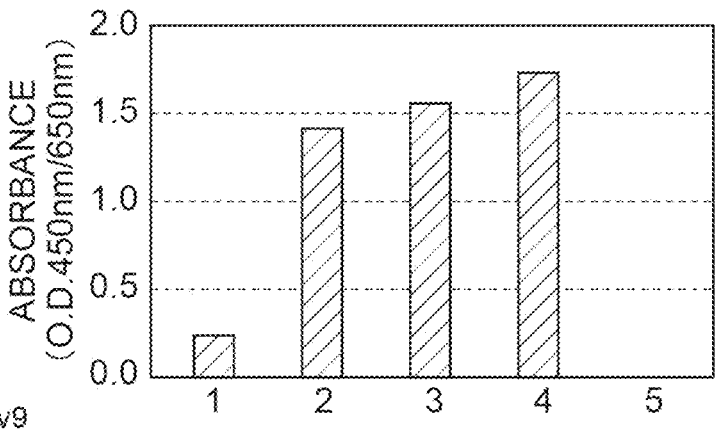
ANTI-PENTAMER ANTIBODY TITER(1/2000)
1.gBv9
2.PENTAMER
3.gH(His-)/gL-Δd4/UL128-Δd4/UL130-Δd4/UL131
4.gH(His-)/gL/UL128-Δd4/UL130-Δd4/UL131-Δd4
5.saline

*Fig.31*
(a)     NEUTRALIZATION ACTIVITY TO MRC-5
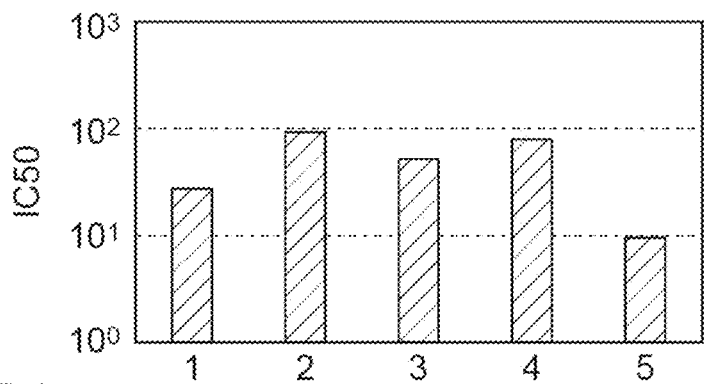
1.gBv9
2.PENTAMER
3.gH(His-)/gL-Δd4/UL128-Δd4/UL130-Δd4/UL131
4.gH(His-)/gL/UL128-Δd4/UL130-Δd4/UL131-Δd4
5.saline
(b)     NEUTRALIZATION ACTIVITY TO ARPE-19
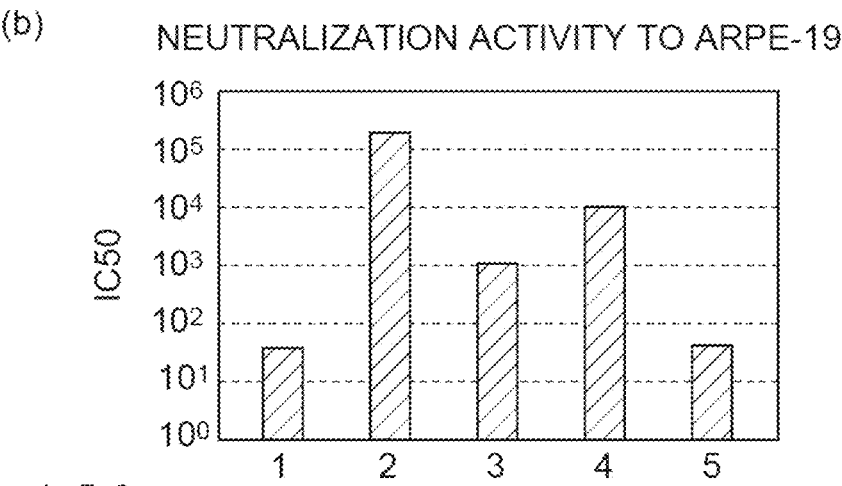
1.gBv9
2.PENTAMER
3.gH(His-)/gL-Δd4/UL128-Δd4/UL130-Δd4/UL131
4.gH(His-)/gL/UL128-Δd4/UL130-Δd4/UL131-Δd4
5.saline gH(His-)/gL-Δd4 /UL128-Δd4 /UL130-Δd4 /UL131

FUSION PROTEIN OF PENTAMER AND gB OF CYTOMEGALOVIRUS, AND VACCINE CONTAINING SAID FUSION PROTEIN

SEQUENCE LISTING SUBMISSION VIA EFS-WEB

A computer readable text file, entitled "SequenceListing.txt" created on Jan. 7, 2023, with a file size of 89,676 bytes and contains the sequence listing for this application and is hereby incorporated by reference in its entirety.

TECHNICAL FIELD

The present invention relates to a fusion protein of gB and a pentamer of cytomegalovirus, and a vaccine for preventing or treating infection with cytomegalovirus containing the fusion protein.

BACKGROUND ART

Cytomegalovirus (CMV) infections mainly include major two: organ dysfunctions such as CMV pneumonia, enteritis, and retinitis that develop in patients in immunocompromised states such as transplantation, AIDS, and congenital immunodeficiency; and congenital CMV infections, which develop in a fetus when a pregnant woman is infected for the first time. Of these, the congenital CMV infection is an important congenital infection that is one of the TORCH syndromes and causes malformation or severe clinical manifestations in fetuses. When pregnant women are infected with CMV for the first time, the congenital infection occurs in approximately 40% of the fetuses via the placenta (the term "congenital infection" herein is used synonymously with the term "infection via the placenta"). Moreover, there is a report that approximately 15% of stillbirths are due to congenital CMV infection. The annual number of occurrences of infants with congenital infection is 3000 or more in Japan and approximately 40000 in the United States, and symptomatic ones are said to be approximately 1000 in Japan and approximately 8000 in the United States, and aftereffects such as central nerve disorders and hearing loss persist in approximately 90% of the symptomatic ones.

The CMV antibody prevalence rate in Japan is higher than in North American and European countries, 80% to 90% of Japanese adults are CMV-antibody positive, and most people are infected in infancy. However, the CMV antibody prevalence rate in young people has shown a tendency to decrease from the 90% range to the 60% range as a recent tendency, and the need for prophylaxis against congenital CMV infections is further increasing (Non Patent Literature 1).

The Institute of Medicine has estimated that congenital CMV infection has an impact exceeding Down syndrome as a cause of congenital central nerve disorders in developed countries, and CMV vaccines are classified in the category with the highest medical economic effectiveness on the basis of the calculation of decrease in the lifetime QOLs of infants with congenital infection who have lasting disorders and socioeconomic loss as QALYs (quality-adjusted life years) (Non Patent Literature 2).

Pathogens that cause infections are classified roughly into Class I pathogens, on which conventional vaccines can produce sufficient effects, and Class II pathogens, of which sufficient protective immunity cannot be acquired by conventional vaccines or the history of infection with the pathogens, and CMV is classified in the latter.

As the reason why it is difficult to conquest Class II pathogens, sophisticated immune escape mechanisms thereof have been indicated. Humankind has so far developed many effective vaccines against Class I pathogens and defeated the menace of infections that they cause. The focus of future vaccine development is shifting to Class II pathogens.

Although uninfected pregnant women are also identified by screening pregnant women and enlightened on notes in lives to minimize damage from congenital CMV infections, the identification and enlightenment are not enough. Furthermore, although there is also a report claiming that it is effective in prevention of infection and reduction of aggravation in fetuses to identify pregnant women infected for the first time and administer an anti-CMV hyperimmunoglobulin to the pregnant women, its efficacy has been questioned now (Non Patent Literature 3). Meanwhile, although ganciclovir has also been marketed as a small molecule drug, its effect is limited, and there are the problems of side effects. A vaccine does not exist currently, there is not a therapy that is enough effective as mentioned above, and an unmet need therefor is therefore high.

About CMV vaccine development, studies using attenuated live vaccines, subunit vaccines, DNA vaccines, and the like have so far been attempted in a plurality of pharmaceutical companies and academia, but both T-cell immune and B-cell immune responses to any of such vaccines are insufficient, and as a result, an effect worthy of practical use as a vaccine has been not gained.

Among described above, a vaccine of Sanofi K. K. is a genetically-modified subunit vaccine having gB, which is a CMV glycoprotein, as an antigen, but approximately 50% infection-preventive effect was exhibited in a clinical trial targeted at uninfected adult women. Since the effect was limited, the development has been actually suspended, but important knowledge that "a certain effect can be exhibited with only a gB antigen (but the effect is not enough)" has been obtained (Non Patent Literature 4).

About the experimental proof of the effect of CMV vaccine candidates, the specificity of CMV to a species needs to be considered. Since CMV has specificity to a species, animal experiments using human cytomegalovirus (HCMV) are basically impossible. The animal experiments are conducted with mice, rats, guinea pigs, monkeys, and the like, and are conducted using CMVs peculiar to various animal species. About the infection via the placenta, only guinea pigs are an animal model system wherein it can be confirmed that fetuses are infected without special treatment by infecting the mothers' bodies with the virus, and the system for testing the infection via the placenta using guinea pigs has been widely utilized (Non Patent Literature 5).

It has been reported about the effect of a gB vaccine on the infection via the placenta that the administration of a gB protein of recombinant guinea pig cytomegalovirus (GPCMV)+an adjuvant to female guinea pigs suppressed the initial infection of female guinea pigs and also suppressed the infection of fetuses via the placenta (Non Patent Literature 6).

It was disclosed in Non Patent Literature 7 that an adenovirus vector vaccine into which a gB protein of GPCMV is incorporated is used, and gB suppresses the infection of fetuses via the placenta in the model of the infection of guinea pigs via the placenta.

Meanwhile, it is a pentamer antigen that attracts great attention as a main antigen of CMV for the past several years. The pentamer is a cell directional determinant of CMV, and is a molecule comprising five subunits that are gH, gL, UL128, UL130, and UL131 (gH/gL/UL128/UL130/UL131) in the case of human CMV (Non Patent Literature 15).

It has been reported about the contribution of the pentamer to the infection via the placenta that GPCMV in which the pentamer gene is deleted loses infectivity to epithelial and endothelial cells and the ability to infect via the placenta, and they are recovered by expressing the deleted gene ectopically (Non Patent Literature 8).

It has been reported about the effect of a pentamer vaccine that a monoclonal antibody induced by administering the vector vaccine MVA-PC that expressed the pentamer to mice was analyzed in detail, so that the neutralizing capacity of an anti-pentamer antibody in epithelial and endothelial cell lines was clearly high as compared with that of an anti-gH antibody, and the neutralizing capacity in trophoblast cells, which are considered to be important in the infection via the placenta, is also similar (Non Patent Literature 9).

Meanwhile, there is also a contrary report. It is claimed in Non Patent Literature 10 that trophoblast precursor cells in the placenta in humans are targets of CMV, the contribution of a pentamer to the infection of the cells with CMV was hardly observed, and the contribution of gB was definitely observed.

It is claimed in Non Patent Literature 11 that the contribution of a pentamer to the infection of placenta tissue with GPCMV and the proliferation is hardly observed using an ex vivo placenta infection test system.

Although reports that suggest the usefulness of a pentamer as a vaccine antigen thus appear occasionally, and the role of the pentamer in the infection via the placenta is not clear, and it has not been able to be said yet that the effect of suppressing the infection via the placenta that the pentamer vaccine has is concluded.

Although it has been reported in the Patent Literature 1 about the effect of the combination of a pentamer and gB that the combination of a recombinant pentamer and a recombinant gB was effective in an infection prevention test targeted at monkeys, the reports suggest nothing about influence on the infection via the placenta at all.

Although it is shown that a group of the combined use of the pentamer+gB is excellent as compared with a pentamer single use group and an unimmunized group, a gB single use group is not set up, the effect of the combination is not correctly shown.

Although it is claimed in Non Patent Literature 12 that the effect of the combination of an anti-gB monoclonal antibody and an anti-pentamer monoclonal antibody is inspected in vitro, and the combination is beneficial for the neutralizing capacity and the suppression of resistant strain appearance, the effect of the combination is not proved about the ability to prevent infection in vivo.

In Patent Literature 2, there are furthermore data stating that some cytokines are more highly produced by immunization against a divalent vaccine of gB+a pentamer than the single use groups, but the combined use group is not excellent in neutralizing capacity, and an infection experiment is not conducted, either. A modified CMV gB protein and a CMV vaccine containing this are disclosed in Patent Literature 4.

The X-ray crystal structure of the pentamer is clarified in Non Patent Literature 15. According to this, a pentamer is a molecule having a helical structure and a major axis of approximately 18 nm, and gH exists at its end, and a part of gH and gL are tangled with each other to form a gH/gL domain. UL128/UL130/UL131 interacts with the N-terminus of gL while having gently curved forms. In UL128/UL130/UL131, UL131 is present at the center of the three. UL130 forms a sheet structure with a β-strand of UL131 on the C-terminus side thereof, and one surface thereof is covered with a helix structure of UL131. Both UL128 and UL130 form spherical structures on the N-terminus sides thereof, and these are located directly oppositely with the core structure between these. The C-terminus side of UL128 interacts with gL through a very flexible linker that reaches 5 nm and fits into a groove of gL to form a small helix structure. In this way, the pentamer has many interactions between internal molecules. However, since the interfaces thereof are small, the pentamer has a very flexible structure, but it is shown that the pentamer can be stabilized when the pentamer binds to Fab. Therefore, the stability may be improved by introducing suitable site-specific mutations.

The X-rays crystal structure of extracellular domains (ectodomains) of gB in which the cohesiveness is improved by site-specific mutation is clarified in Non Patent Literature 13. According to this, a homotrimer has a spike-like structure in gB, and its protomer comprises five domains. Domain I and Domain II are adjacently located on the side near the cell membrane, and Domain III forms a coiled-coil structure by a very long helix structure. Domain IV is located on the directly opposite side of the cell membrane, and Domain V exists from Domain I to Domain III along the full-length gB. The N-terminus is located near Domain IV, and the C-terminus exists in domain V.

The three-dimensional structure of the CMV gB protein is analyzed (Non Patent Literature 13), and for example, it is known that gB protein derived from the strain AD169 (SEQ ID NO: 1) has Domain I, consisting of the amino acid residues at positions 109-319; Domain II, consisting of the amino acid residues at positions 97-108 and the amino acid residues at positions 320-414; Domain III, consisting of the amino acid residues at positions 71-87, the amino acid residues at positions 453-525, and the amino acid residues at positions 614-643; Domain IV, consisting of the amino acid residues at positions 65-70 and the amino acid residues at positions 526-613; and Domain V, consisting of the amino acid residues at positions 644-675 in SEQ ID NO: 1.

There are five antigenic domains (ADs) in gB (AD-1-AD-5), and AD-1 is supposed to have the highest antigenicity. It is believed that AD-1 is located in Domain IV, relatively few N-sugar chains are in Domain IV, and an antigen is exposed, an antibody therefore accesses easily. In Patent Literature 4, it is furthermore reported that non-neutralizing antibodies are concentrated in a region containing Domain IV (head region) and reported that gB in which the head region is removed may be used as a vaccine.

CITATION LIST

Patent Literature

Patent Literature 1
International Publication No. WO 2017153954
Patent Literature 2
Japanese Unexamined Patent Publication No. 2017-515503
Patent Literature 3
International Publication No. WO 2003004647
Patent Literature 4
International Publication No. WO 2020085457

Non Patent Literature

Non Patent Literature 1
Azuma H et al., "Cytomegalovirus seropositivity in pregnant women in Japan during 1996-2009" J Jpn Soc Perin Neon Med 46 (2010) 1273-1279
Non Patent Literature 2
Kathleen R. Stratton et al., "Vaccines for the 21st century: a tool for decision making" The National Academies Press, 2000 Non Patent Literature 3
Revello M G et al., "Randomized trial of hyperimmune globulin to prevent congenital cytomegalovirus" N Engl J Med 370 (2014) 1316-1326
Non Patent Literature 4
Rieder F et al., "Cytomegalovirus vaccine: phase II clinical trial results" Clin Microbiol Infect 20 Suppl 5 (2014) 95-102
Non Patent Literature 5
Yamada S et al., "Characterization of the guinea pig cytomegalovirus genome locus that encodes homologs of human cytomegalovirus major immediate-early genes, UL128, and UL130" Virology 391 (2009) 99-106
Non Patent Literature 6
Schleiss M R et al., "Glycoprotein B (gB) vaccines adjuvanted with AS01 or AS02 protect female guinea pigs against cytomegalovirus (CMV) viremia and offspring mortality in a CMV-challenge model" Vaccine 32 (2014) 2756-2762
Non Patent Literature 7
Hashimoto K et al., "Effects of immunization of pregnant guinea pigs with guinea pig cytomegalovirus glycoprotein B on viral spread in the placenta" Vaccine 31 (2013) 3199-3205
Non Patent Literature 8
Coleman S et al., "A Homolog Pentameric Complex Dictates Viral Epithelial Tropism, Pathogenicity and Congenital Infection Rate in Guinea Pig Cytomegalovirus" PLoS Pathog 12 (2016) e1005755
Non Patent Literature 9
Flavia Chiuppesi et al., "Vaccine-Derived Neutralizing Antibodies to the Human Cytomegalovirus gH/gL Pentamer Potently Block Primary Cytotrophoblast Infection" J Virol 89 (2015) 11884-11898
Non Patent Literature 10
Martin Zydek et al., "HCMV Infection of Human Trophoblast Progenitor Cells of the Placenta Is Neutralized by a Human Monoclonal Antibody to Glycoprotein B and Not by Antibodies to the Pentamer Complex" Viruses 6 (2014) 1346-1364
Non Patent Literature 11
Yamada S et al., "An Ex vivo culture model for placental cytomegalovirus infection using slices of Guinea pig placental tissue" Placenta 37 (2016) 85-88
Non Patent Literature 12
Hetalkumar D et al., "In Vitro Characterization of Human Cytomegalovirus-Targeting Therapeutic Monoclonal Antibodies LJP538 and LJP539" Antimicrob Agents Chemother 60 (2016) 4961-4971
Non Patent Literature 13
Burke H G et al., "Crystal Structure of the Human Cytomegalovirus Glycoprotein B" PLoS Pathog 11 (2015) e1005227
Non Patent Literature 14
Ciferri C et al., "Structural and biochemical studies of HCMV gH/gL/gO and Pentamer reveal mutually exclusive cell entry complexes" Proc Natl Acad Sci USA 112 (2015) 1767-1772
Non Patent Literature 15
Chandramouli S et al., "Structural basis for potent antibody-mediated neutralization of human cytomegalovirus." Sci Immunol 2(2017) eaanl 457

SUMMARY OF INVENTION

Technical Problem

As mentioned above, an effective CMV vaccine that can suppress especially congenital infection with CMV in the prevention of CMV infection does not exist. An object of the present invention is therefore to provide an effective vaccine that can prevent and treat infection with CMV.

Solution to Problem

The present inventors have proposed a vaccine for preventing and treating congenital infection with CMV containing a CMV gB antigen and a pentamer antigen in the previous investigation (disclosed as international application PCT/JP2019/047966, WO2020/121983 on Jun. 18, 2020). The present inventors have earnestly investigated to provide a further effective vaccine, thereby to found that congenital infection of guinea pigs with CMV can be strongly suppressed, and the stability of the pentamer molecules is improved in the form of a fusion protein by creating a protein complex in which gB and a pentamer, which are main antigens of CMV, are fused by genetic engineering to produce a subunit vaccine consisting of one protein, and completed the present invention.

That is, the present invention relates to the following inventions.

[1] A fusion protein of envelope glycoprotein B (gB protein) and a pentamer of cytomegalovirus (CMV).

[2] The fusion protein according to [1], wherein a homotrimer of the gB protein consisting of three gB protein constituent molecules and a heteropentamer of the pentamer consisting of five pentamer constituent molecules form a protein complex by fusion of at least one gB protein constituent molecule with at least one pentamer constituent molecule by genetic engineering.

[3] The fusion protein according to [2], wherein at least two gB protein constituent molecules are fused with at least two pentamer constituent molecules by genetic engineering.

[4] The fusion protein according to [2] or [3], wherein the three gB protein constituent molecules are fused with any three pentamer constituent molecules of the five pentamer constituent molecules by genetic engineering.

[5] The fusion protein according to any one of [2] to [4], wherein the three gB protein constituent molecules are fused with gL, UL128, and UL130 as pentamer constituent molecules by genetic engineering.

[6] The fusion protein according to any one of [2] to [4], wherein the three gB protein constituent molecules are fused with UL128, UL130, and UL131 as pentamer constituent molecules by genetic engineering.

[7] The fusion protein according to any one of [2] to [6], wherein at least one fusion of fusions by genetic engineering is a fusion in which a pentamer constituent molecule is bound to an N-terminus side of the gB protein constituent molecule.

[8] The fusion protein according to any one of [3] to [6], wherein at least two fusions of the fusions by genetic engineering are fusions in which pentamer constituent molecules are bound to an N-terminus side of the gB protein constituent molecules.

[9] The fusion protein according to any one of [4] to [6], wherein all three fusions by genetic engineering are fusions in which pentamer constituent molecules are bound to an N-terminus side of the gB protein constituent molecules.

[10] The fusion protein according to any one of [2] to [9], wherein the fusion protein has a linker and/or a tag between the gB protein constituent molecule and the pentamer constituent molecule.

[11] The fusion protein according to [10], wherein the linker is a linker consisting of an amino acid sequence having one to three repeats of an amino acid sequence unit set forth in SEQ ID NO: 22.

[12] The fusion protein according to any one of [1] to [11], wherein the gB protein is an ectodomain of the CMV gB protein.

[13] The fusion protein according to [12], wherein the gB protein is an ectodomain of a gB protein of human cytomegalovirus (HCMV) consisting of an amino acid sequence set forth in SEQ ID NO: 15 or the amino acid sequence in which one or more amino acid residues are deleted, substituted, or added.

[14] The fusion protein according to [12] or [13], wherein the gB protein is an ectodomain of a gB protein having 80% or more sequence identity with an ectodomain of the gB protein consisting of the amino acid sequence set forth in SEQ ID NO: 15.

[15] The fusion protein according to any one of [1] to [14], wherein the gB protein is a gB protein variant in which Domain IV is deleted.

[16] The fusion protein according to [15], wherein the gB protein is an ectodomain of a gB protein of human cytomegalovirus (HCMV) consisting of an amino acid sequence set forth in SEQ ID NO: 16 or the amino acid sequence in which one or more amino acid residues are deleted, substituted, or added.

[17] The fusion protein according to [15] or [16], wherein the gB protein is an ectodomain of a gB protein having 80% or more sequence identity with an ectodomain of a gB protein consisting of the amino acid sequence set forth in SEQ ID NO: 16.

[18] The fusion protein according to any one of [1] to [14], wherein the gB protein is a gB protein variant having introduced therein a modification for reducing formation of an aggregate and increasing a rate of a homotrimer structure as compared with a wild type gB protein.

[19] The fusion protein according to [18], wherein the gB protein is an ectodomain of a gB protein of human cytomegalovirus (HCMV) consisting of an amino acid sequence set forth in SEQ ID NO: 3 or the amino acid sequence in which one or more amino acid residues are deleted, substituted, or added.

[20] The fusion protein according to [18] or [19], wherein the gB protein is an ectodomain of a gB protein having 80% or more sequence identity with an ectodomain of a gB protein consisting of the amino acid sequence set forth in SEQ ID NO: 3.

[21] The fusion protein according to any one of [1] to [14], wherein the gB protein is a gB protein variant having introduced therein a modification for reducing immunogenicity of a head region as compared with a wild type gB protein.

[22] The fusion protein according to [21], wherein the gB protein is an ectodomain of a gB protein of human cytomegalovirus (HCMV) consisting of an amino acid sequence set forth in SEQ ID NO: 31 or the amino acid sequence in which one or more amino acid residues are deleted, substituted, or added.

[23] The fusion protein according to [21] or [22], wherein the gB protein is an ectodomain of a gB protein having 80% or more sequence identity with an ectodomain of the gB protein consisting of the amino acid sequence set forth in SEQ ID NO: 31.

[24] The fusion protein according to any one of [1] to [23], wherein the pentamer consists of gH, gL, UL128, UL130, and UL131 of human cytomegalovirus (HCMV).

[25] The fusion protein according to [24], wherein the gH is an ectodomain of gH protein.

[26] The fusion protein according to [24] or [25], wherein the pentamer is a pentamer protein of human cytomegalovirus (HCMV) comprising:

gH consisting of an amino acid sequence set forth in SEQ ID NO: 4 or the amino acid sequence in which one or more amino acid residues are deleted, substituted, or added;

gL consisting of an amino acid sequence set forth in SEQ ID NO: 5 or the amino acid sequence in which one or more amino acid residues are deleted, substituted, or added;

UL128 consisting of an amino acid sequence set forth in SEQ ID NO: 6 or the amino acid sequence in which one or more amino acid residues are deleted, substituted, or added;

UL130 consisting of an amino acid sequence set forth in SEQ ID NO: 7 or the amino acid sequence in which one or more amino acid residues are deleted, substituted, or added; and UL131 consisting of an amino acid sequence set forth in SEQ ID NO: 8 or the amino acid sequence in which one or more amino acid residues are deleted, substituted, or added.

[27] The fusion protein according to any one of [24] to [26], wherein the pentamer is a pentamer protein of HCMV comprising:

gH having 80% or more sequence identity with gH consisting of the amino acid sequence set forth in SEQ ID NO: 4;

gL having 80% or more sequence identity with gL consisting of the amino acid sequence set forth in SEQ ID NO: 5;

UL128 having 80% or more sequence identity with UL128 consisting of the amino acid sequence set forth in SEQ ID NO: 6;

UL130 having 80% or more sequence identity with UL130 consisting of the amino acid sequence set forth in SEQ ID NO: 7; and UL131 having 80% or more sequence identity with UL131 consisting of the amino acid sequence set forth in SEQ ID NO: 8.

[28] A nucleic acid fragment encoding the fusion protein according to any one of [1] to [27].

[29] A recombinant expression vector comprising the nucleic acid fragment according to [28].

[30] A transformant having introduced therein the nucleic acid fragment according to [28] or the recombinant expression vector according to [29].

[31] A vaccine for preventing or treating infection with CMV, comprising the fusion protein according to any one of [1] to [27].

[32] The vaccine according to [31], wherein the infection with CMV is congenital infection with CMV.

Advantageous Effects of Invention

According to the present invention, a vaccine having the effect of suppressing infection exceeding the effect of the single administration of gB or a pentamer using a fusion protein of gB and a pentamer as an antigen can be provided in the prevention of congenital infection with CMV. The practical use of the CMV vaccine can be expected thereby.

BRIEF DESCRIPTION OF DRAWINGS

FIG. 1 is a figure showing the results of subjecting purified products of gB-pentamer constituent protein fusion bodies of Example 1 to gel filtration chromatography.

FIG. 2 is a figure showing the results of subjecting purified products of gB-pentamer constituent protein fusion bodies of Example 1 to gel filtration chromatography.

FIG. 3 is a figure showing the results of subjecting purified products of gB-pentamer constituent protein fusion bodies of Example 1 to gel filtration chromatography.

FIG. 5 is a figure showing the results of subjecting purified products of the gB-pentamer constituent protein fusion bodies of Example 2 to gel filtration chromatography.

FIG. 8 is a figure showing the results of analyzing the reactivities of the gB-pentamer constituent protein fusion bodies of Example 3-1 using HCMV-gB immune serum and pentamer immune serum.

FIG. 10 is a figure showing the results of subjecting purified products of the gB-pentamer constituent protein fusion bodies of Example 3-1 to gel filtration chromatography.

FIG. 11 is a figure showing the results of subjecting purified products of the gB-pentamer constituent protein fusion bodies of Example 3-1 to gel filtration chromatography.

FIG. 12 is a figure showing the results of subjecting purified products of the gB-pentamer constituent protein fusion bodies of Example 3-1 to gel filtration chromatography.

FIG. 13 is a figure showing the results of subjecting purified products of the gB-pentamer constituent protein fusion bodies of Example 3-1 to gel filtration chromatography.

FIG. 14 is a figure showing the results of the antibody titer measurement of the gB-pentamer constituent protein fusion body immune sera of Example 3-1.

FIG. 15 is a figure showing the results of the neutralization activities of the gB-pentamer constituent protein fusion body immune sera of Example 3-1.

FIG. 16 is a figure showing the results of analyzing the reactivities of purified products of the gB-pentamer constituent protein fusion bodies of Example 3-2-1 using Δd4 immune serum.

FIG. 20 is a figure showing the results of subjecting purified products of the gB-pentamer constituent protein fusion bodies of Example 3-2-1 to gel filtration chromatography.

FIG. 21 is a figure showing the results of the particle size evaluation of purified products of the gB-pentamer constituent protein fusion bodies of Example 3-2-1.

FIG. 22 is a figure showing results of the particle size distribution of purified products of the gB-pentamer constituent protein fusion bodies of Example 4.

FIG. 23 is a figure showing the results of the particle size distribution of purified products of the gB-pentamer constituent protein fusion bodies of Example 4.

FIG. 25 is a figure showing the results of subjecting purified products of the gB-pentamer constituent protein fusion bodies of Example 6 to gel filtration chromatography.

FIG. 28 is a figure showing the results of subjecting purified products of the gB-pentamer constituent protein fusion bodies of Example 3-2-2 to gel filtration chromatography.

FIG. 29 is a figure showing the results of the particle size evaluation of purified products of the gB-pentamer constituent protein fusion bodies of Example 3-2-2.

FIG. 30 is a figure showing the results of the antibody titer measurement of gB-pentamer constituent protein fusion body immune sera of Example 3-2-3.

FIG. 31 is a figure showing the results of the neutralization activities of gB-pentamer constituent protein fusion body immune sera of Example 3-2-3.

DESCRIPTION OF EMBODIMENTS

Figure 4:
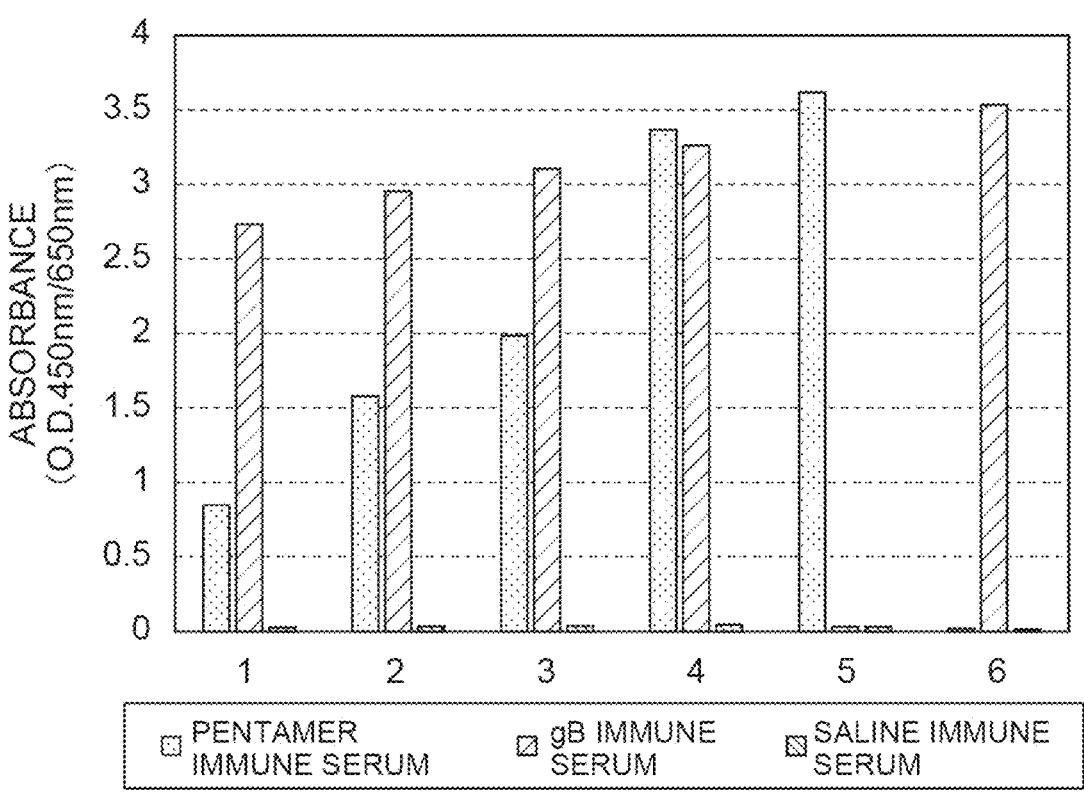
FIG. 4 is a figure showing the results of analyzing the reactivities of the gB-pentamer constituent protein fusion bodies of Example 2 using HCMV-gB immune serum and pentamer immune serum.
Figure 6:
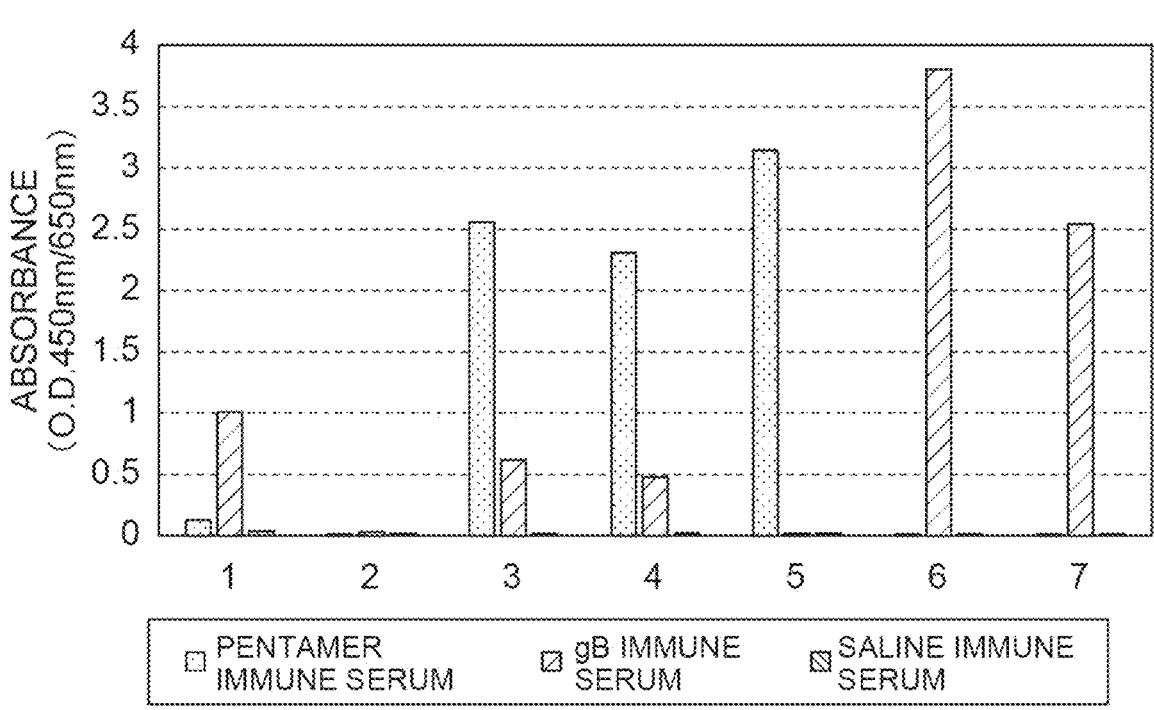
FIG. 6 is a figure showing the results of analyzing the reactivities of the gB-pentamer constituent protein fusion bodies of Example 3-1 using HCMV-gB immune serum and pentamer immune serum.
Figure 7:
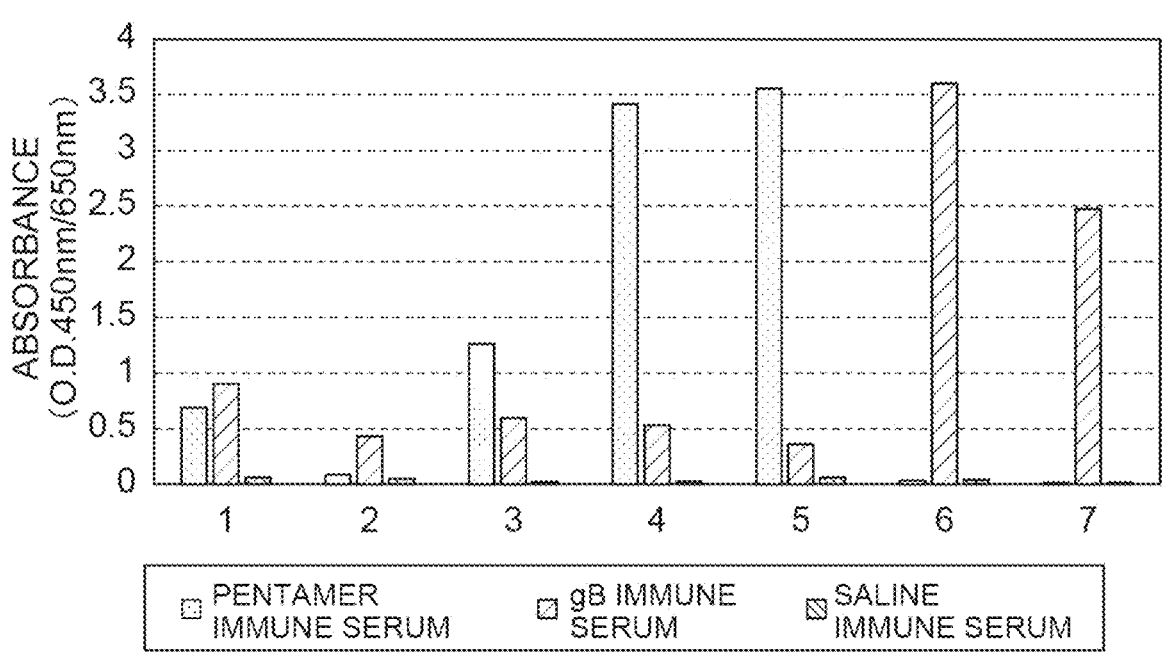
FIG. 7 is a figure showing the results of analyzing the reactivities of the gB-pentamer constituent protein fusion bodies of Example 3-1 using HCMV-gB immune serum and pentamer immune serum.
Figure 9:
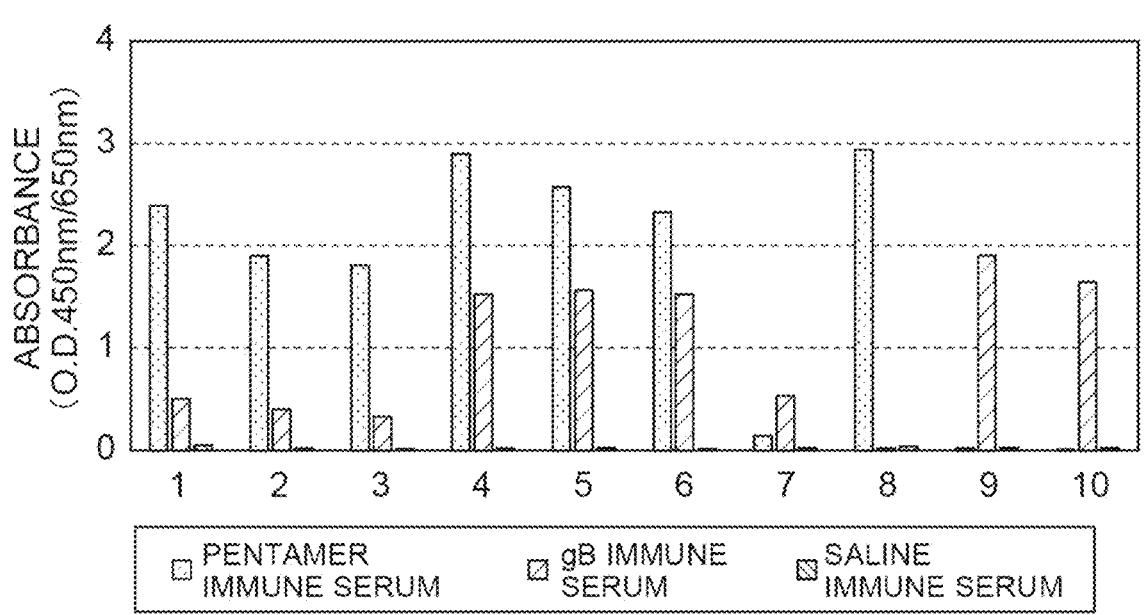
FIG. 9 is a figure showing the results of analyzing the reactivities of the gB-pentamer constituent protein fusion bodies of Example 3-1 using HCMV-gB immune serum and pentamer immune serum.
Figure 17:
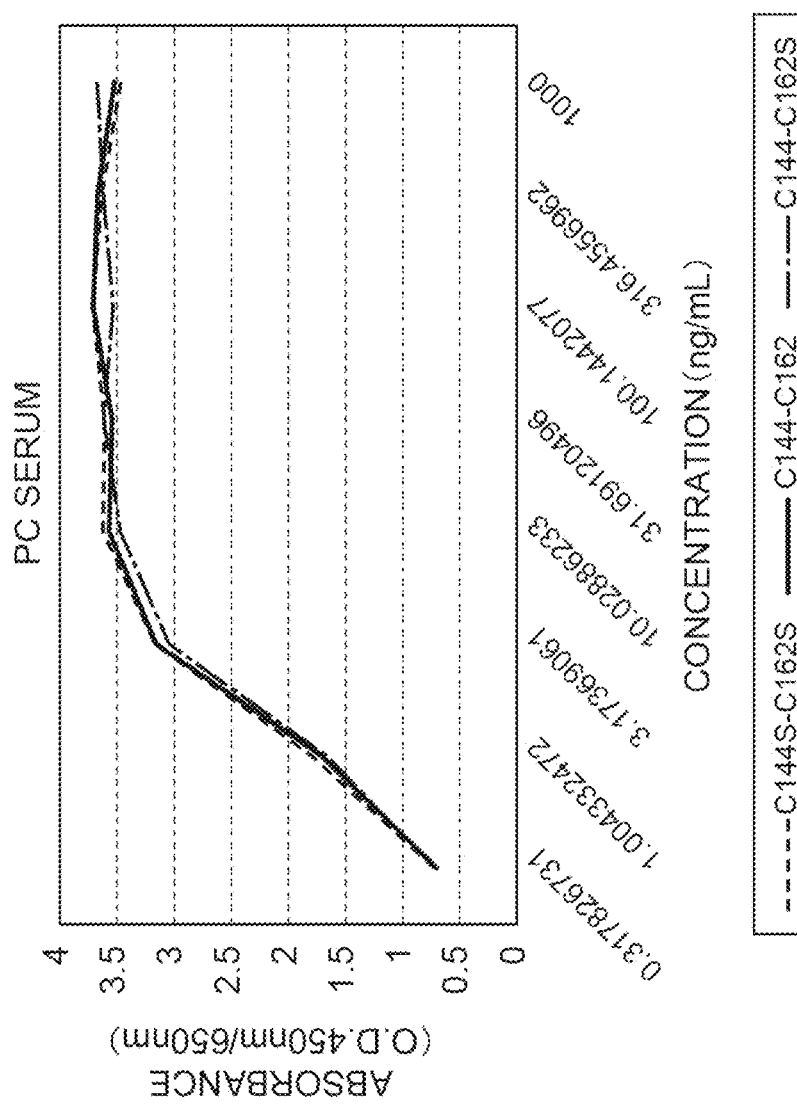
FIG. 17 is a figure showing the results of analyzing the reactivities purified products of the gB-pentamer constituent protein fusion bodies of Example 3-2-1 using pentamer (PC) immune serum.
Figure 18:
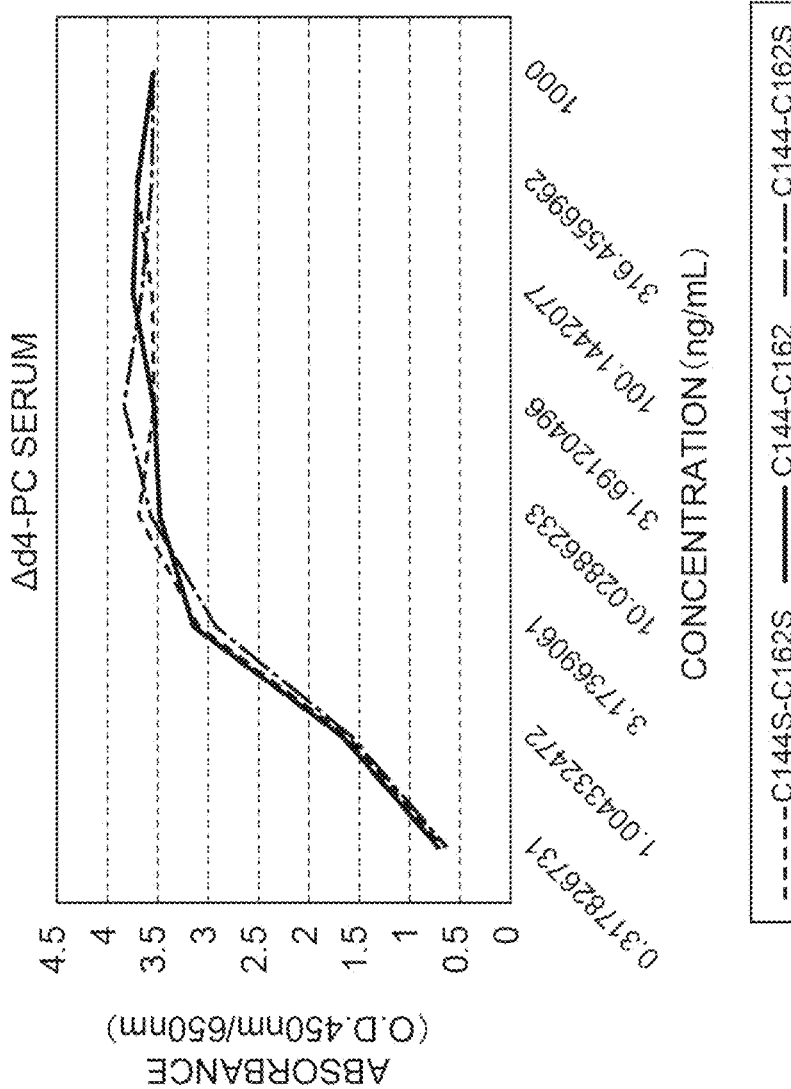
FIG. 18 is a figure showing the results of analyzing the reactivities of purified products of the gB-pentamer constituent protein fusion bodies of Example 3-2-1 using gH(His-)/gL-Δd4/UL128(C162S)-Δd4/UL130-Δd4/UL131 (Δd4/PC) immune serum.
Figure 19:
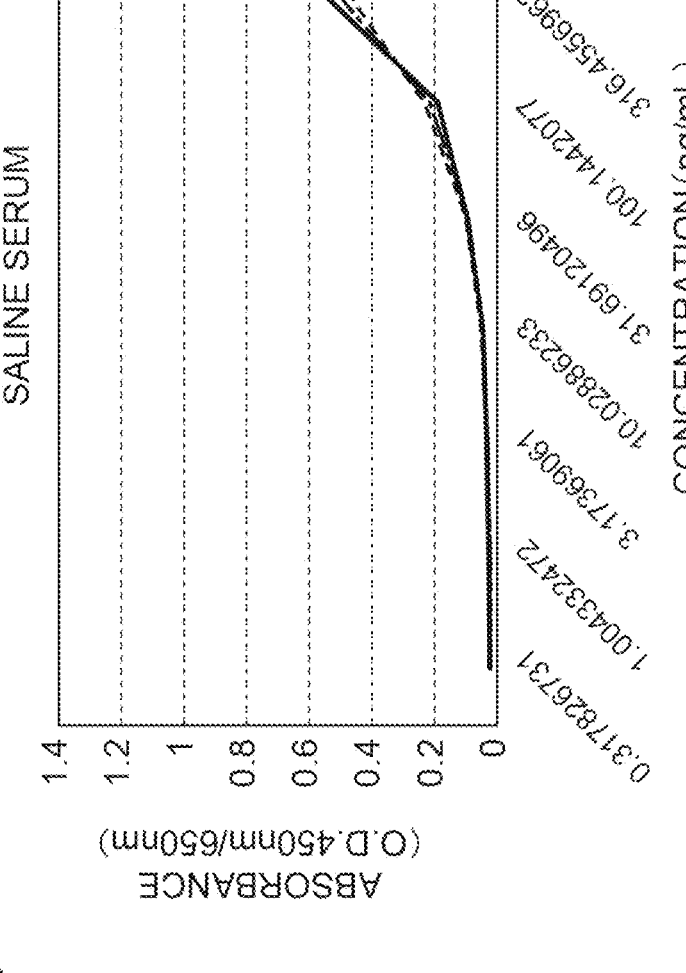
FIG. 19 is a figure showing the results of analyzing the reactivities of purified products of the gB-pentamer constituent protein fusion bodies of Example 3-2-1 using saline immune serum.

Embodiments of the present invention will be described in detail hereinafter. However, the present invention is not limited to the following embodiments.

11

[Fusion Protein]

A fusion protein of the present invention is a fusion protein of envelope glycoprotein B (gB protein) and a pentamer of cytomegalovirus (CMV). The fusion protein is a fusion protein wherein a homotrimer of a gB protein consisting of three gB protein constituent molecules and a heteropentamer of a pentamer consisting of five pentamer constituent molecules form a protein complex by fusion of at least one gB protein constituent molecule with at least one pentamer constituent molecule by genetic engineering. Here, the constituent molecule refers to a protein constituting the homotrimer of the gB protein or the heteropentamer of the pentamer, and also refers to a subunit. The fusion protein is used as an antigen for preparing a vaccine useful for preventing and treating CMV.

The fusion protein is preferably a protein complex wherein at least two gB protein constituent molecules are fused with at least two pentamer constituent molecules by genetic engineering to form the protein complex, and is more preferably a protein complex wherein the three gB protein constituent molecules are fused with any three pentamer constituent molecules of the five pentamer constituent molecules by genetic engineering to form the protein complex.

Cytomegalovirus (CMV) includes any CMV strain, and examples includes human cytomegalovirus (HCMV), guinea pig cytomegalovirus (GPCMV), mouse cytomegalovirus (MCMV), rat cytomegalovirus (RCMV), and rhesus monkey cytomegalovirus (RhCMV). It is preferable that the cytomegalovirus be HCMV.

The gB protein of CMV in this embodiment may be a wild type CMV gB protein or a modified type CMV gB protein.

The wild type CMV gB protein means a gB protein derived from any CMV strain, and examples include a gB protein having an amino acid sequence set forth in SEQ ID NO: 1 and derived from HCMV the strain AD169 (GenBank accession number: X17403.1) and a gB protein having an amino acid sequence set forth in SEQ ID NO: 2 and derived from GPCMV the strain 22122 (GenBank accession number: AB592928.1).

The modified type CMV gB protein (also referred to as a "gB protein variant", a "gB variant", or a "variant") refers to a protein in which at least one amino acid residue or continuous amino acid residue region is substituted, deleted, or added in the wild type CMV gB protein, and includes proteins such as proteins subjected to sugar chain introduction by amino acid residue substitution or removal subjected to protein modification absent from the wild type.

The gB variant may have the amino acid sequence of the wild type CMV gB protein, in which 1 or more, for example, 1-50, 1-40, 1-30, 1-20, 1-15, 1-10, 1-5, 1-3, amino acid residues are deleted, substituted, or added, and the substitution, deletion, or addition may occur at the same time. Here, amino acid addition includes both insertion into the original amino acid sequence and addition to a terminus of the original amino acid sequence. The amino acid residue used herein may be referred to as merely an amino acid when it is clear that the amino acid residue is an amino acid residue.

The gB variant may be a variant having modification that does not influence the three-dimensional structure and function of the original gB protein or a variant having improved properties. Examples of the gB variant having improved properties include a variant having introduced therein a modification for preventing or reducing aggregate formation and increasing the rate of the homotrimer structure or a variant having introduced therein a modification for improving the ability to induce an antibody or a neutralizing antibody, for example a modification for reducing the immunogenicity of the head region of the gB protein described in Patent Literature 4. The "neutralizing antibody inducing ability" refers to the ability to enable inducing neutralizing antibodies to an antigen protein, and can be evaluated with the neutralizing antibody titer in immune serum obtained by inoculating the antigen protein into a test animal. The "neutralizing antibody" refers to an antibody capable of eliminating the infectivity of virions, and the level of the neutralization activity of the antibody can be evaluated with the concentration of the antibody necessary to decrease, for example, 50% of the number of plaques of a test virus (NT50).

The gB protein of CMV in this embodiment may be the full-length CMV gB protein, or may be an antigenic fragment of the CMV gB protein.

Examples of the full-length gB protein include an HCMV gB protein consisting of an amino acid sequence set forth in the above-mentioned SEQ ID NO: 1 (GenBank accession number: X17403.1). In the amino acid sequences set forth in SEQ ID NO: 1, an amino acid sequence at positions 1-24 is however a signal sequence (SEQ ID NO: 19). Therefore, the full-length CMV gB protein may be a HCMV gB protein in which the above-mentioned signal sequence (SEQ ID NO: 19) is deleted from the amino acid sequence set forth in SEQ ID NO: 1.

Since the fusion protein of the present invention is used as an antigen for preparing a vaccine useful for preventing and treating CMV, an antigenic fragment of the gB protein may be a fragment that has antigenicity and can form homotrimers, and examples includes an extracellular domain (ectodomain) of the gB protein of CMV, or a fragment or a variant of the ectodomain. Examples of the ectodomain include a fragment of the HCMV gB protein consisting of an amino acid sequence at positions 25-706 in the amino acid sequence described in HCMV derived from HCMV the strain AD169 (SEQ ID NO: 1), and this fragment is defined as an ectodomain of the wild type HCMV gB protein (SEQ ID NO: 15). An ectodomain of another CMV gB protein is defined with corresponding positions based on the sequence alignment with the ectodomain of HCMV derived from the above-mentioned HCMV the strain AD169 (SEQ ID NO: 15). The ectodomain of the gB protein in this embodiment may be an ectodomain of the wild type CMV gB protein or an ectodomain of the modified type CMV gB protein (ectodomain variant of the gB protein).

The ectodomain of the gB protein or the variant thereof may be an ectodomain of the gB protein of HCMV consisting of the amino acid sequence set forth in SEQ ID NO: 15 or the amino acid sequence in which 1 or more, for example, 1-50, 1-40, 1-30, 1-20, 1-15, 1-10, 1-5, or 1-3, amino acid residues are deleted, substituted, or added.

The ectodomain of the gB protein or the variant thereof may be an ectodomain of the gB protein having 80% or more, for example, 85% or more, 90% or more, 93% or more, 95% or more or 98% or more, sequence identity with the ectodomain of the gB protein consisting of the amino acid sequence set forth in SEQ ID NO: 15. Here, the sequence identity refers to the percentage of (number of amino acid residues corresponding in sequences)/(full length of amino acid sequence) when a plurality of sequences are aligned. For example, target sequences are aligned with the genetic information processing software GENETYX, and % Identity Matrix generated by excluding a gap from calculation corresponds to sequence identity.

For example, the variant of the ectodomain of the gB protein may be a variant in which Domain IV is deleted. For example, the variant may be a variant in which amino acids at positions 97 to 468 and amino acids at positions 631 to 682 in the amino acid sequence set forth in SEQ ID NO: 15 are connected with each other directly or via a suitable peptide linker. The variant may be a variant in which the amino acid substitutions Y131A, I132A, Y133A, W216A, R432T, and R434Q are further introduced into the variant in which the Domain IV is deleted, and examples include a variant in which amino acids at positions 97 to 468 and amino acids at positions 631 to 682 in SEQ ID NO: 15 are connected with each other via nine amino acids of GGGSGSGGG (SEQ ID NO: 20), and the amino acid substitutions Y131A, I132A, Y133A, W216A, R432T, and R434Q are further introduced ("gBΔd4") (SEQ ID NO: 16).

The variant in which Domain IV is deleted may be an ectodomain of a gB protein of human cytomegalovirus (HCMV) consisting of the amino acid sequence set forth in SEQ ID NO: 16 in which 1 or more, for example, 1-50, 1-40, 1-30, 1-20, 1-15, 1-10, 1-5, or 1-3, amino acid residues are deleted, substituted, or added.

The variant in which Domain IV is deleted may be an ectodomain of the gB protein wherein the gB protein has 80% or more, for example, 85% or more, 90% or more, 93% or more, 95% or more, or 98% or more, sequence identity with an ectodomain of the gB protein consisting of an amino acid sequence set forth in SEQ ID NO: 16.

Examples of the gB protein variant having introduced therein a modification for reducing the formation of aggregates and increasing the rate of the homotrimer structure include an HCMV gB protein ectodomain variant (SEQ ID NO: 3) in which the amino acid residue at position 132 is substituted with a histidine residue (His), the amino acid residue at position 133 is substituted with an arginine residue (Arg), the amino acid residue at position 215 is substituted with a glutamic acid residue (Glu), the amino acid residue at position 216 is substituted with an alanine residue (Ala), the amino acid residue at position 432 is substituted with a threonine residue (Thr), and the amino acid residue at position 434 is substituted with a glutamine residue (Gln) based on the ectodomain of the HCMV gB protein consisting of an amino acid sequence set forth in SEQ ID NO: 15 with reference to Non Patent Literature 13.

The above-mentioned gB protein variant may be an ectodomain of the gB protein of human cytomegalovirus (HCMV) consisting of the amino acid sequence set forth in SEQ ID NO: 3 in which 1 or more, for example, 1-50, 1-40, 1-30, 1-20, 1-15, 1-10, 1-5, 1-3, amino acid residues are deleted, substituted, or added.

The above-mentioned gB protein variant may be an ectodomain of the gB protein having 80% or more, for example, 85% or more, 90% or more, 93% or more, 95% or more or 98% or more, sequence identity with an ectodomain of the gB protein consisting of the amino acid sequence set forth in SEQ ID NO: 3.

Examples of the gB protein variant having introduced therein a modification for improving the antibody inducing ability or the neutralizing antibody inducing ability include a gB protein variant having introduced therein a modification for reducing the immunogenicity of the head region of the gB protein, and examples include a gB protein variant (gBVC37, SEQ ID NO: 31) in which the same mutations as SEQ ID NO: 3 is introduced, S128-L138 is further deleted, R127 and G139 at the termini are connected by a glycine linker GGG, and W216-Y218 is deleted, and four N-sugar chains are introduced (D77N, I79T/E544N, P546T/L588N, P589G/K609N, R610T, M611T) in the amino acid sequence set forth in SEQ ID NO: 15 (Patent Literature 4).

The above-mentioned gB protein variant may be an ectodomain of a gB protein of human cytomegalovirus (HCMV) consisting of the amino acid sequence set forth in SEQ ID NO: 31 in which 1 or more, for example, 1-50, 1-40, 1-30, 1-20, 1-15, 1-10, 1-5, or 1-3, amino acid residues are deleted, substituted, or added.

The above-mentioned gB protein variant may be an ectodomain of the gB protein having 80% or more, for example, 85% or more, 90% or more, 93% or more, 95% or more, or 98% or more, sequence identity with an ectodomain of the gB protein consisting of the amino acid sequences set forth in SEQ ID NO: 31.

A gB protein antigen of CMV may be prepared by protein purification using CMV and can be prepared by a technique of genetic engineering. The preparation method is not particularly limited, and for example, the cDNA of the wild type gB protein is used as a template, primers are designed, a nucleic acid is obtained by PCR and functionally connected with an expression promoter, and a tag is also connected under certain circumstances, the nucleic acid can be introduced into a suitable expression vector and expressed to obtain the gB protein antigen of CMV. The prepared CMV gB protein antigen may be purified if needed. The purification method is not particularly limited, and examples include purification with affinity chromatography column or the like.

If the modified type gB protein antigen is a variant produced by mutation introduction, primers for introducing target mutations are designed, a nucleic acid into which the mutations are introduced is obtained by PCR and functionally connected with an expression promoter, and a tag is also connected under certain circumstances, the nucleic acid can be introduced into a suitable expression vector and expressed to obtain the modified type gB protein antigen.

If the modified type gB protein antigen is a variant produced by sugar chain introduction (sugar chain modification), the method may be a normal method and is not particularly limited, and for example, if an N-sugar chain is introduced, the cDNA of the wild type gB protein is used as a template, primers are designed so that the sequence of three continuous amino acids at a target site into which the N-sugar chain is introduced is N-X-S/T (X is any amino acid other than proline), and the mutation is introduced by PCR. The nucleic acid sequence of the target modified type gB protein or the nucleic acid sequence with which a tag such as 6×His is further connected if necessary can be cloned into a suitable vector and expressed to obtain the modified type CMV gB protein. The N-sugar chain is added to asparagine at the target site of the gB variant by a normal method.

The pentamer of CMV also refers to a pentamer complex consisting of five different constituent molecules (subunits), or a heteropentamer or merely a pentamer. The pentamer may be a wild type CMV pentamer or a modified type CMV pentamer.

The wild type CMV pentamer means a pentamer derived from any CMV strain, and examples include a pentamer of human cytomegalovirus (HCMV) consisting of gH, gL, UL128, UL130, and UL131 and a pentamer of guinea pig cytomegalovirus (GPCMV) consisting of GP75 (gH), GP115 (gL), GP129 (UL128), GP131 (UL130), and GP133 (UL131).

Examples of the HCMV pentamer include a pentamer protein consisting of amino acid sequences set forth in SEQ ID NO: 4 (gH), SEQ ID NO: 5 (gL), SEQ ID NO: 6 (UL128), SEQ ID NO: 7 (UL130), and SEQ ID NO: 8 (UL131) and derived from HCMV the Merlin strain (Gen- Bank accession number: AY446894.2) (however, since the sequence of UL128 includes a mutation, the sequence is corrected based on sequence information on CMV other strains).

Examples of the GPCMV pentamer include a pentamer protein consisting of amino acid sequences set forth in SEQ ID NO: 10 (GP75), SEQ ID NO: 11 (GP115), SEQ ID NO: 12 (GP129), SEQ ID NO: 13 (GP131), and SEQ ID NO: 14 (GP133) and derived from GPCMV the strain 22122 (Gen-Bank accession number: AB592928.1) (however, since the sequence of GP133 includes a mutation, the sequence is corrected based on the sequence information on CMV other strains).

The subunits (constituent molecules) of the modified type CMV pentamer may be variants having modification that does not influence the three-dimensional structures and functions of the original subunits or variants in which the properties are improved. Examples of the subunit variants in which the properties are improved include a variant having introduced therein a modification for preventing or reducing aggregate formation and increasing the content of the pentamer thereby, or a variant having introduced therein a modification for improving the ability to induce an antibody or a neutralizing antibody. The modified type CMV pentamer refers to a pentamer in which at least one of the five subunits constituting the wild type CMV pentamer is a modified protein (subunit variant). The subunit variant refers to a protein in which one or more amino acid residues or continuous amino acid residue regions are substituted, deleted, or added in the corresponding wild type subunit and includes proteins such as proteins into which sugar chains are introduced by amino acid residue substitution, deletion, or addition subjected to protein modifications absent from the wild type. Here, amino acid addition includes both insertion into the original amino acid sequence and addition to a terminus of the original amino acid sequence.

An HCMV pentamer of one embodiment may be a pentamer protein of HCMV comprising:

gH consisting of an amino acid sequence set forth in SEQ ID NO: 4 or the amino acid sequence in which one or more amino acid residues are deleted, substituted, or added;

gL consisting of an amino acid sequence set forth in SEQ ID NO: 5 or the amino acid sequence in which one or more amino acid residues are deleted, substituted, or added;

UL128 consisting of an amino acid sequence set forth in SEQ ID NO: 6 or the amino acid sequence in which one or more amino acid residues are deleted, substituted, or added;

UL130 consisting of an amino acid sequence set forth in SEQ ID NO: 7 or the amino acid sequence in which one or more amino acid residues are deleted, substituted, or added; and UL131 consisting of an amino acid sequence set forth in SEQ ID NO: 8 or the amino acid sequence in which one or more amino acid residues are deleted, substituted, or added. Here, the deletion, substitution, or addition of 1 or more amino acid residues may be the deletion, substitution, or addition of, for example, 1-50, 1-40, 1-30, 1-20, 1-15, 1-10, 1-5, or 1-3, amino acid residues.

A HCMV pentamer of one embodiment may be a pentamer protein of HCMV comprising:

gH having 80% or more sequence identity with gH consisting of the amino acid sequence set forth in SEQ ID NO: 4;

gL having 80% or more sequence identity with gL consisting of the amino acid sequence set forth in SEQ ID NO: 5;

UL128 having 80% or more sequence identity with UL128 consisting of the amino acid sequence set forth in SEQ ID NO: 6;

UL130 having 80% or more sequence identity with UL130 consisting of the amino acid sequence set forth in SEQ ID NO: 7; and UL131 having 80% or more sequence identity with UL131 consisting of the amino acid sequence set forth in SEQ ID NO: 8. Here, the 80% or more sequence identity may be, for example, 85% or more, 90% or more, 93% or more, 95% or more, or 98% or more sequence identity.

An GPCMV pentamer of one embodiment may be a pentamer protein of GPCMV comprising:

GP75 consisting of an amino acid sequence set forth in SEQ ID NO: 10 or the amino acid sequence in which one or more amino acid residues are deleted, substituted, or added;

GP115 consisting of an amino acid sequence set forth in SEQ ID NO: 11 or the amino acid sequence in which one or more amino acid residues are deleted, substituted, or added;

GP129 consisting of an amino acid sequence set forth in SEQ ID NO: 12 or the amino acid sequence in which one or more amino acid residues are deleted, substituted, or added;

GP131 consisting of an amino acid sequence set forth in SEQ ID NO: 13 or the amino acid sequence in which one or more amino acid residues are deleted, substituted, or added; and GP133 consisting of an amino acid sequence set forth in SEQ ID NO: 14 or the amino acid sequence in which one or more amino acid residues are deleted, substituted, or added. Here, the deletion, substitution, or addition of 1 or more amino acid residues may be the deletion, substitution, or addition of, for example, 1-50, 1-40, 1-30, 1-20, 1-15, 1-10, 1-5, or 1-3 amino acid residues.

A GPCMV pentamer of one embodiment may be a pentamer protein of GPCMV comprising:

GP75 having 80% or more sequence identity with GP75 consisting of the amino acid sequence set forth in SEQ ID NO: 10;

GP115 having 80% or more sequence identity with GP115 consisting of the amino acid sequence set forth in SEQ ID NO: 11;

GP129 having 80% or more sequence identity with GP129 consisting of the amino acid sequence set forth in SEQ ID NO: 12;

GP131 having 80% or more sequence identity with GP131 consisting of the amino acid sequence set forth in SEQ ID NO: 13; and GP133 having 80% or more sequence identity with GP133 consisting of the amino acid sequence set forth in SEQ ID NO: 14. Here, the 80% or more sequence identity may be, for example, 85% or more, 90% or more, 93% or more, 95% or more, or 98% or more sequence identity.

The subunits may have the full-length or, for example, only ectodomains. It is preferable that gH be an ectodomain of the gH protein.

The CMV pentamer antigen may be prepared by protein purification using CMV, and can be prepared by a technique of genetic engineering. The preparation method is not particularly limited, for example, the cDNAs of the five protein that constitutes the wild type CMV pentamer are used as templates, primers are designed, nucleic acids are obtained by PCR and functionally connected with an expression promoter, tags are also connected under certain circumstances, and the nucleic acids are introduced into suitable expression vectors and expressed, the obtained protein are folded to form a pentamer structure, and the CMV pentamer antigen can be obtained thereby. The CMV pentamer antigen can also be expressed as a secreted protein as needed. For example, gH is expressed not as full-length gH (SEQ ID NO: 9) but as a fragment of the ectodomain (SEQ ID NO: 4) to enable expression as a secreted protein. The prepared CMV pentamer antigen may be purified as needed. Although the purification method is not particularly limited, examples include purification with affinity chromatography columns or the like.

If the modified type CMV pentamer antigen is a variant produced by mutation introduction or a variant produced by sugar chain introduction (sugar chain modification), the modified type CMV pentamer antigen can be prepared as mentioned above.

The fusion protein of the present invention has both three-dimensional structures of gB and the pentamer partially. gB and one or more pentamer constituent molecules may be connected, and the combination thereof can also be suitably selected. Even when gB and the pentamer constituent molecules are expressed with gB and one or more pentamer constituent molecules connected and the other molecules not fused, these can form complexes with the connected molecules, and it can therefore be said that these are a gB-pentamer fusion protein. The gB-pentamer fusion protein may be connected in any combination.

In a fusion protein of one embodiment, a subunit of the pentamer to be fused with a gB protein constituent molecule by genetic engineering is not particularly limited, one gB protein constituent molecule may be fused with any one of the subunits of the pentamer by genetic engineering, the combination of subunits of pentamers to be fused with two or three gB protein constituent molecules by genetic engineering is not particularly limited, either, constituent subunits of the pentamer to be fused with the three gB protein constituent molecules of the homotrimer may be also gL, UL128, and UL130, and the constituent subunits of the pentamer to be fused with gB protein may be UL128, UL130 and UL131.

In a fusion protein of one embodiment, the fusion by genetic engineering may be a fusion in which a gB protein is bound to a pentamer from the N-terminus side sequentially (that is, a fusion in which the N-terminus of the constituent molecule of the pentamer is connected with the C-terminus of the gB protein constituent molecule), or may be a fusion in which the pentamer is bound to the gB protein from the N-terminus side sequentially. Since a fusion protein in which the pentamer binds to the gB protein from the N-terminus side sequentially, that is, a fusion protein in which the pentamer binds to the N-terminus side of the gB protein, tends to hardly form aggregates, the fusion protein is preferable. That is, it is preferable that at least one fusion of the fusions by genetic engineering is a fusion in which a pentamer constituent molecule is bound to the N-terminus side of the gB protein constituent molecule, and it is more preferable that at least two fusions of the fusions by genetic engineering are fusions in which pentamer constituent molecules are bound to the N-terminus side of gB protein constituent molecules, and it is particularly preferable that all the three fusions by genetic engineering are fusions in which pentamer constituent molecules are bound to the N-terminus side of the gB protein constituent molecules.

In the fusion protein, the gB protein may bind to the pentamer directly, but it is preferable that the gB protein bind to the pentamer preferably through a suitable linker and/or a tag. It is believed that when the fusion protein has a linker with a suitable length between the gB protein and the pentamer, both can form suitable structures without sterically hindering each other. When the fusion protein has a tag between the gB protein and the pentamer, the fusion protein can be purified by affinity purification. The fusion protein may have a linker and/or a tag not only between the gB protein and the pentamer but also on the N-terminus side or the C-terminus side of the fusion protein.

The linker is not particularly limited, and those skilled in the art can design the linker suitably. Examples include a linker of 5 amino acids having Gly-Gly-Gly-Gly-Ser (SEQ ID NO: 22) as a unit, and examples include a linker consisting of an amino acid sequence having one to three repeats of the amino acid sequence unit set forth in SEQ ID NO: 22.

The tag is not particularly limited, those skilled in the art can select the tag suitably. Examples include a His-tag in which a plurality of histidine residues lie in a line (for example, a His-tag having an amino acid sequence set forth in SEQ ID NO: 30).

As described in the Examples, the fusion protein of gB and the pentamer of CMV can furthermore be created by fusing the pentamer with the gB using genetic engineering. [Nucleic Acid Fragment, Recombinant Expression Vector, and Transformant]

The nucleic acid fragment of the present invention is a nucleic acid fragment encoding the fusion protein of gB and the pentamer of the CMV of the present invention, and the recombinant expression vector of the present invention is a recombinant expression vector containing the nucleic acid fragment of the present invention, and a transformant of the present invention is a transformant having introduced therein the nucleic acid fragment of the present invention or the recombinant expression vector of the present invention.

As long as the nucleic acid fragment encoding the fusion protein can finally be expressed as the fusion protein in which gB binds to the pentamer at the time of transcribing and expressing the nucleic acid fragment in a host, the nucleic acid fragment is not particularly limited. For example, the nucleic acid fragment encoding the gB protein and the nucleic acid fragments encoding each of subunits of the pentamer can be functionally connected to obtain the nucleic acid fragment. It is preferable that a codon such as a termination codon that stops transcription halfway be not contained between these nucleic acid fragments.

The nucleic acid fragment encoding the wild type gB protein can be acquired, for example, by southern hybridization to the DNAs of various CMVs using probe DNAs that can be designed based on a gene encoding wild type gB having an amino acid sequence set forth in SEQ ID NO: 1 or SEQ ID NO: 2 or by PCR with a primer set that can be designed based on the genes using the DNAs of various CMVs as templates.

The nucleic acid fragment encoding a variant of the gB protein can be acquired, for example, by error-prone PCR or the like using the DNA consisting of the sequence represented by SEQ ID NO: 1 as a template. Alternatively, the nucleic acid fragment can be obtained by site-specific mutation introduction.

The nucleic acid fragment encoding the gB protein can be obtained by the artificial synthesis of a nucleic acid fragment encoding an amino acid sequence and designed based on amino acid sequences such as SEQ ID NO: 1-3, 15, 16, and 31.

The nucleic acid fragments encoding the subunits of the wild type or modified type pentamer, for example, the subunits of SEQ ID NO: 4-8 or SEQ ID NO: 10-14, can be also similarly acquired.

The above-mentioned acquired nucleic acid fragments are subjected to nothing or cleaved with suitable restriction enzymes or the like, the nucleic acid fragments are incorporated into vectors by the usual method, the obtained recombinant expression vectors are introduced into host cells, followed by analysis using a nucleotide sequence analyzing device of a commonly used method for analyzing a nucleotide sequence, or the like to determine the sequences of the nucleic acid fragments.

Examples of the vectors that can be used for recombinant expression vectors can include, but are not limited to, a pCAGGS vector using a CAG promoter and a pCMV vector using a CMV promoter.

The above-mentioned nucleic acid fragment or recombinant expression vector can be introduced into host cells to obtain the transformant. The introduction may be conducted by the usual method. Examples of the host cells include, but are not particularly limited to, CHO cells, HEK293 cells, SP2/0 cells, BHK cells, and NSO cells.

The transformant is cultured in suitable culture medium and subjected to expression induction as needed to express the fusion protein of the present invention, and it can be collected and purified as needed to obtain the fusion protein of the present invention.

[Vaccine]

The vaccine of the present invention contains the fusion protein of the present invention. A vaccine of one embodiment is a vaccine for preventing or treating congenital infection with CMV containing a fusion protein of the envelope glycoprotein B (gB protein) and the pentamer of the cytomegalovirus (CMV) as an antigen. That is, the vaccine according to this embodiment is a subunit vaccine consisting of the fusion protein having both functions of two antigenic proteins.

The content of the protein antigen in the vaccine of this embodiment may be 0.1-1000 µg with respect to each of the gB protein antigen of CMV and the CMV pentamer antigen, and it is preferable that the content be 1-100 µg.

The dosage form of the vaccine of this embodiment may be, for example, a liquid form, a powdered form (freeze-dried powder, dry powder), a capsule form, a tablet form, or a frozen state.

The CMV vaccine of this embodiment may comprise a pharmaceutically acceptable carrier. As the above-described carrier, a carrier that is usually used for vaccine manufacture may be used without limitation, and specifically, examples include saline, buffered saline, dextrose, water, glycerol, aqueous isotonic buffer solutions, and combinations thereof. The vaccine may further contain an emulsifier, a preservative (for example, thimerosal), an isotonizing agent, a pH adjuster, an inactivating agent (for example, formalin), and the like suitably.

To further increase immunogenicity of the vaccine of this embodiment, an adjuvant may further be contained. Examples of the adjuvant include aluminum adjuvants or oil-in-water type emulsion adjuvants (AS03, MF59, and the like) containing squalene, ligands of Toll-like receptors such as CpG and 3-O-deacylated-4'-monophosphoryl lipid A (MPL), saponin-based adjuvants, polymer adjuvants such as poly-γ-glutamic acid, and polysaccharides such as chitosan and inulin.

The vaccine of this embodiment can be obtained by mixing the antigen that is a fusion protein of gB and the pentamer of CMV with the carrier, the adjuvant, and the like as needed. The adjuvant may be an adjuvant that is mixed at the time of use.

The administration route of the vaccine of this embodiment may be, for example, transdermal administration, sublingual administration, ophthalmic administration, intradermal administration, intramuscular administration, oral administration, enteral administration, transnasal administration, intravenous administration, subcutaneous administration, intraperitoneal administration, or inhalational administration from the mouth to the lung.

The mode of administration of the vaccine of this embodiment may be, for example, a mode of administration with a syringe, a transdermal patch, microneedles, an implantable sustained release device, a syringe with microneedles, a needle-free device, or a spray.

According to a vaccine of this embodiment, infection with CMV via the placenta can be prevented or treated. The prevention of infection via the placenta is to suppress vertical infection of a fetus with CMV or to suppress the development of various symptoms caused by congenital infection by administering the vaccine to a mother's body. These can be evaluated by inspection using nucleic acid amplification with the liquor *amnii* of a fetus or the body fluid of a neonate, neonatal head ultrasonography, head CT inspection, head MRI inspection, auditory screening, or the like. The treatment of infection via the placenta is to suppress the development and progress of various symptoms caused by congenital infection by administering the vaccine to a congenitally infected child. These can be evaluated by the hearing test, the eyesight test, the other physical tests, or the mental development test of the congenitally infected child. It is preferable to administer the vaccine of this embodiment to women or female children at baby-bearing ages. It is also considered that men and male children, or elderly persons are targeted from the viewpoint of herd immunity. The number of administrations is once to three times, and a plurality of inoculations at an interval of two months to several years is however desirable. The blood antibody titers are measured, and persons in whom the antibody is negative, or the blood antibody titers are low can also be targeted to inoculate.

EXAMPLES

Hereinafter, the present invention will be described more specifically based on the following Examples. However, the present invention is not limited to the following Examples.

Example 1

<Antigen Preparation>

A gene encoding an ectodomain of HCMV gB derived from the strain AD169 (SEQ ID NO: 15) was artificially synthesized and cloned into pCAGGS1-dhfr-neo (Patent Literature 3). The design was conducted so that a His-tag of 9 amino acids (SEQ ID NO: 30) was added to the C-terminus. A gene in which the amino acid substitutions of I132H, Y133R, T215E, W216A, R432T, and R434Q were performed based on this (SEQ ID NO: 3) was prepared as gB1-682-fim3Mv9 (hereinafter called "gBv9") (Patent Literature 4). When gBv9 was expressed, a signal sequence of HCMV-gB (MESRIWCLVVCVNLCIVCLGAAVS) (SEQ ID NO: 19) was inserted at the N-terminus.

The Expi293 expression system (Life Technologies Corporation) was used for the expression. Cells were transfected with the expression plasmid, and the culture supernatant was collected in 4 to 6 days. The culture supernatant containing gBv9 was purified using Ni NTA Agarose (QIAGEN), and the purified culture supernatant was dialyzed against PBS+ 0.5 M arginine to obtain a purified product of the ectodomain of the HCMV gB protein.

A protein in which the amino acids at positions 97 to 468 and amino acids at positions 631 to 682 of the gB ectodomain (SEQ ID NO: 15) were connected with each other via 9 amino acids of GGGSGSGGG (SEQ ID NO: 20) and into which the amino acid substitutions of Y131A, I132A, Y133A, W216A, R432T, and R434Q were further introduced was referred to as "gBΔd4" (SEQ ID NO: 16), a DNA fragment encoding gBΔd4 was prepared based on an artificial synthesized gene by polymerase chain reaction (PCR), and the DNA fragment was cloned into pCAGGS1-dhfr-neo (the same molecule as D1D2 in Patent Literature 4). When gBΔd4 was expressed, a signal sequence of HCMV-gB (MESRIWCLVVCVNLCIVCLGAAVS) (SEQ ID NO: 19) was inserted at the N-terminus, and a His-tag of 9 amino acids (SEQ ID NO: 30) was inserted at the C-terminus. The expression and the purification were performed by the same methods as gBv9.

A gene encoding UL128 (SEQ ID NO: 6), a gene encoding UL130 (SEQ ID NO: 7), and a gene encoding UL131 (SEQ ID NO: 8) were artificially synthesized separately and cloned into pCAGGS1-dhfr-neo.

Then, a DNA fragment encoding a fusion protein in which gBv9 was added to the C-terminus side of a "signal peptide-substituted UL128", in which a signal sequence (1 to 27 amino acids) of UL128 (SEQ ID NO: 6) was deleted, and a human immunoglobulin light chain signal peptide sequence (MRLPAQLLGLL-MLWVPGSSG) (SEQ ID NO: 21) was inserted at the same position, a "signal peptide-substituted UL130", in which a signal sequence (1 to 25 amino acids) of UL130 (SEQ ID NO: 7) was deleted, and the amino acid sequence MRL-PAQLLGLLMLWVPGSSG (SEQ ID NO: 21) was inserted at the same position, or a "signal peptide-substituted UL131", in which a signal sequence (1 to 18 amino acids) of UL131 (SEQ ID NO: 8) was deleted, and the amino acid sequence MRL-PAQLLGLLMLWVPGSSG (SEQ ID NO: 21) was inserted at the same position, through a linker of 5 amino acids (GGGGS) (SEQ ID NO: 22) was prepared by PCR and cloned into pCAGGS1-dhfr-neo. Among these, the fusion protein in which gBv9 was connected with the signal peptide-substituted UL128 was referred to as N-UL128-gB, the fusion protein in which gBv9 was connected with the signal peptide-substituted UL130 was referred to as N-UL130-gB, and the fusion protein in which gBv9 was connected with the signal peptide-substituted UL131 was referred to as N-UL131-gB.

A DNA fragment encoding a fusion protein in which the signal sequence (MESRIWCLVVCVNLCIVCLGAAVS) of HCMV-gB (SEQ ID NO: 19) was inserted at the N-terminus of gBv9, the His-tag (SEQ ID NO: 30) was deleted from the C-terminus side of gBv9, a signal-removed UL128, from which the signal sequence (1 to 27 amino acids) of UL128 (SEQ ID NO: 6) was removed, or a signal-removed UL130, from which the signal sequence (1 to 25 amino acids) of UL130 (SEQ ID NO: 7) was removed, or a signal-removed UL131, from which the signal sequence (1 to 18 amino acids) UL131 (SEQ ID NO: 8) was removed, was connected through a linker of 5 amino acids (GGGGS) (SEQ ID NO: 22), and a His-tag of 9 amino acids (SEQ ID NO: 30) was further added to the C-terminus side thereof was prepared by PCR and cloned into pCAGGS1-dhfr-neo. Among these, a fusion protein in which gBv9 was connected with signal-removed UL128 was referred to as C-UL128-gB, a fusion protein in which gBv9 was connected with signal-removed UL130 was referred to as C-UL130-gB, and a fusion protein in which gBv9 was connected with signal-removed UL131 was referred to as C-UL131-gB.

Then, a DNA fragment encoding a fusion protein in which 373aa-381aa of gBΔd4 (SEQ ID NO: 16) were removed, signal-removed UL128, or signal-removed UL130, or signal-removed UL131 was inserted at the same position was prepared by PCR and cloned into pCAGGS1-dhfr-neo. A signal sequence of HCMV-gB (MESRIWCLVVCVNL-CIVCLGAAVS) (SEQ ID NO: 19) was inserted at the N-terminus of any of the DNA fragments. Among these, the fusion protein into which signal-removed UL128 was inserted was referred to as Δd4-UL128-gB, the fusion protein into which signal-removed UL130 was inserted was referred to as Δd4-UL130-gB, and the fusion protein into which signal-removed UL131 was inserted was referred to as Δd4-UL131-gB.

The expression and the purification were performed by the same method as for the gB protein of HCMV to obtain purified products of a total of 12 sets of the fusion proteins of gB and pentamer constituent proteins in the cases where N-UL128-gB, N-UL130-gB, and N-UL131-gB were expressed alone and separately, the case where the three that were N-UL128-gB, N-UL130-gB and N-UL131-gB were coexpressed (N-UL128-gB/N-UL130-gB/N-UL131-gB), the case where C-UL128-gB, C-UL130-gB and C-UL131-gB were expressed alone and separately, the case where the three that were C-UL128-gB, C-UL130-gB and C-UL131-gB were coexpressed (C-UL128-gB/C-UL130-gB/C-UL131-gB), the cases where Δd4-UL128-gB, Δd4-UL130-gB and Δd4-UL131-gB were expressed alone and separately, and the case where the three that were Δd4-UL128-gB, Δd4-UL130-gB and Δd4-UL131-gB were coexpressed (Δd4-UL128-gB/Δd4-UL130-gB/Δd4-UL131-gB). Here, fusion proteins of gB or parts thereof and pentamer constituent proteins or parts thereof, monomers or polymers obtained by expressing these fusion proteins in cells, and genes encoding these fusion proteins or DNA fragments thereof may be generally referred to as "gB-pentamer constituent protein fusion bodies" herein as long as the above are not confused.

<Gel Filtration Chromatography of Protein Purified Products>

The properties of the acquired purified products were evaluated by gel filtration chromatography. Each purified product at a concentration of 100 μg/mL was applied using a Superdex200 Increase 5/150 GL (General Electric Company) as the column. The absorbance at a wavelength of 280 nm was measured at a flow rate of 0.4 mL/min using D-PBS (FUJIFILM Wako Pure Chemical Corporation) as the mobile phase.

<Results>

The results of the gel filtration chromatography are shown in FIGS. 1 to 3. Aggregates were confirmed in all the expressed products. However, when C-UL128-gB, C-UL130-gB, C-UL131-gB, and C-UL128-gB/C-UL130-gB/C-UL131-gB were expressed and when Δd4-UL128-gB, Δd4-UL130-gB, Δd4-UL131-gB, and Δd4-UL128-gB/Δd4-UL130-gB/Δd4-UL131-gB were expressed, it was confirmed that the aggregate content increased as compared with when N-UL128-gB, N-UL130-gB, N-UL131-gB, and N-UL128-gB/N-UL130-gB/N-UL131-gB were expressed. It was suggested from this that when UL128, UL130, or UL131 was fused with the HCMV gB protein, the fusion on the N-terminus side of the HCMV gB protein suppressed aggregate formation, and increased the contents of others than the aggregates.

Example 2

<Antigen Preparation>

When UL128, UL130, or UL131 was fused with the N-terminus side of gB, a decrease in the aggregate content was observed by the examination of Example 1, and gB-pentamer constituent protein fusion bodies in which UL128, UL130, or UL131 was fused with the N-terminus side of gB as follows were therefore designed.

A fusion protein in which the C162S amino acid substitution was added to UL128 (SEQ ID NO: 6), and gBv9 was further added to the C-terminus side through a linker of 5 amino acids (GGGGS) (SEQ ID NO: 22) was referred to as UL128(C162S)-gB.

A fusion protein in which the C162S amino acid substitution was added to UL128 (SEQ ID NO: 6), and gBΔd4 was further added to the C-terminus side through a linker of 15 amino acids (GGGGSGGGGSGGGGS) (SEQ ID NO: 23) was referred to as UL128(C162S)-Δd4.

gBΔd4 was added to the C-terminus side of UL128 (SEQ ID NO: 6), UL130 (SEQ ID NO: 7), or UL131 (SEQ ID NO: 8) gene through a linker of 15 amino acids (GGGGSGGGGSGGGGS) (SEQ ID NO: 23), and among these, a fusion protein in which the N-terminus side was UL128 was referred to as UL128-Δd4, a fusion protein in which the N-terminus side was UL130 was referred to as UL130-Δd4, and a fusion protein in which the N-terminus side was UL131 was referred to as UL131-Δd4.

A fusion protein in which S128aa-L138aa of gBv9 was removed, and R127 and G139 at termini were connected by the glycine linker GGG, and W216aa-Y218aa was removed, and N-sugar chains were introduced into four positions (D77N, I79T/E544N, P546T/L588N, P589G/K609N, R610T, M611T) was referred to as gBVC37 (SEQ ID NO: 31) (Patent Literature 4). When gBVC37 was expressed, a signal sequence (MESRIWCLVVCVNLCIVCLGAAVS) of HCMV-gB (SEQ ID NO: 19) was inserted at the N-terminus.

A fusion protein in which the C162S amino acid substitution was added to UL128 (SEQ ID NO: 6), and gBVC37 was added to the C-terminus side through a linker of 5 amino acids (GGGGS) (SEQ ID NO: 22) was referred to as UL128(C162S)-VC37.

gBVC37 was added to the C-terminus side of UL128 (SEQ ID NO: 6), UL130 (SEQ ID NO: 7), or a UL131 (SEQ ID NO: 8) gene through a linker of 5 amino acids (GGGGS) (SEQ ID NO: 22), and among these, a fusion protein in which the N-terminus side was UL128 was referred to as UL128-VC37, a fusion protein in which the N-terminus side was UL130 was referred to as UL130-VC37, and a fusion protein in which the N-terminus side was UL131 was referred to as UL131-VC37.

A DNA fragment encoding each gB-pentamer constituent protein fusion body was prepared by PCR and cloned into pCAGGS1-dhfr-neo to prepare a gB-pentamer constituent protein fusion body expression plasmid.

Among ectodomains of the pentamer derived from HCMV the Merlin strain, a gene encoding gH (1-715aa, SEQ ID NO: 4) and a gene encoding gL (1-278aa, SEQ ID NO: 5) were artificially synthesized separately and cloned into pCAGGS1-dhfr-neo. Here, design was performed so that a His-tag of 9 amino acids (SEQ ID NO: 30) was added to the C-terminus of gH (gH used hereinafter refers to the sequence in which this His-tag was added).

Various gB-pentamer constituent protein fusion body expression plasmids were combined for coexpression at the time of the expression. The combined expression plasmids were a total of seven sets that were N-UL128-gB/N-UL130-gB/N-UL131-gB,
UL128(C162S)-gB/N-UL130-gB/N-UL131-gB,
UL128(C162S)-VC37/UL130-VC37/UL131-VC37,
UL128(C162S)-Δd4/UL130-Δd4/UL131-Δd4,
UL128-Δd4/UL130-Δd4/UL131-Δd4, and
gH/gL/UL128/UL130/UL131 (pentamer),
gBv9.

gH/gL/UL128/UL130/UL131 corresponds to an ectodomain of the HCMV pentamer, and is referred to as the "pentamer" hereinafter. The expression was performed by the same method as for the HCMV gB protein to obtain culture supernatant of each gB-pentamer constituent protein fusion body. The pentamer was purified by the same method as for the HCMV gB protein.

<Immunization>

Guinea pigs (Hartley) were immunized using gBv9 and the pentamer as antigens. Each antigen was prepared with physiological saline (Otsuka Pharmaceutical Co., Ltd.) to 5 μg/animal, and 10 v/v % Alum (InvivoGen vac-alu250) and 50 μg/animal of CpG ODN1826 (Eurofins) were used as adjuvants. The prepared antigen solutions intramuscularly inoculated (100 μL/foot, administered to both feet) into guinea pigs (female, three animals/group) at two-week intervals three times, and the whole blood was collected by cardiac blood collection under isoflurane inhalation anesthesia 2 weeks after the final immunization. The obtained blood was separated into serum in a separation tube containing a coagulation accelerator. After the serum separation, the serum from three animals was pooled, and gBv9 immune serum and pentamer immune serum were obtained. The reactivities of the gB-pentamer constituent protein fusion bodies with the gBv9 immune serum and pentamer immune serum were evaluated using these.

<Reactivity Analysis Using Sera>

The reactivities of the culture supernatants of the acquired gB-pentamer constituent protein fusion bodies with the various immune sera (binding activities) were evaluated by ELISA. Rabbit anti 6 His Ab (Bethyl Laboratories, Inc. A190-114) was diluted with PBS (SIGMA) to 1 μg/mL, and 100 μL of the dilution was added to a MaxiSorp plate (Nunc) and immobilized by incubating at 4° C. overnight. After the immobilization, the plate was washed with PBS, 1% BSA/PBS solution was added in 300 μL/well, and the mixture was left to stand for 1 hour or more and blocked. After the blocking, the 1% BSA/PBS solution was discarded, and the acquired culture supernatant was diluted 10 times, and 100 μL of the dilution was added to a well of the plate for incubation at room temperature. After 1 hour, the mixture was washed with PBST, and 100 µL of each of the various immune sera was added to each well of the plate for incubation at room temperature. After 1 hour, the mixture was washed with PBST, and 100 µL of the detection antibody HRP-Rabbit anti Guinea Pig IgG (Invitrogen 614620) was added to the well of the plate for incubation at room temperature. After 1 hour, the mixture was washed with PBST, and 100 µL of TMB (SIGMA T-4444) was added to the well of the plate for color development. After 30 minutes, the reaction was stopped with 1 N sulfuric acid, and the color development value (O.D. 450 nm/650 nm) was measured with a microplate reader (Molecular Devices, LLC.).

<Gel Filtration Chromatography of Protein Purified Product>

The properties of the acquired purified products was evaluated by gel filtration chromatography. First, 50 µL of each purified product at a concentration of 100 µg/mL was applied using a Superdex 200 Increase 5/150 GL (GE Healthcare) as the column. The absorbance at a wavelength of 280 nm was measured at a flow rate of 0.4 mL/min using D-PBS (Wako) as the migration buffer.

<Results>

The results of the reactivity analysis using the HCMV-gB immune serum (gBv9 immune serum) and the pentamer immune serum are shown in FIG. 4. According to FIG. 4, the gB-pentamer constituent protein fusion bodies in all the combinations of UL128(C162S)-gB/N-UL130-gB/N-UL131-gB, UL128(C162S)-VC37/UL130-VC37/UL131-VC37, UL128(C162S)-Δd4/UL130-Δd4/UL131-Δd4, and N-UL128-gB/N-UL130-gB/N-UL131-gB also had reactivity with both HCMV-gB immune serum and pentamer immune serum. When the point mutation of C162S was introduced into UL128, Improvement in the reactivity with the pentamer immune serum was observed. Furthermore, the gB-pentamer constituent protein fusion bodies in which the gB portions of the gB-pentamer constituent protein fusion bodies were gBVC37 or gBΔd4 had high reactivities with the pentamer immune serum as compared with the gB-pentamer constituent protein fusion bodies in which the gB portions of the gB-pentamer constituent protein fusion bodies were gBv9.

The results of the evaluation of the purified products of UL128(C162S)-Δd4/UL130-Δd4/UL131-Δd4 and UL128-Δd4/UL130-Δd4/UL131-Δd4 by gel filtration chromatography are shown in FIG. 5. The main component of each peak estimated from the position of each peak was illustrated. According to FIG. 5, increase in the contents of the trimers in these purified products was observed. It was shown from this that the gB-pentamer constituent protein fusion body had reactivity with the HCMV-gB immune serum and the pentamer immune serum even though the HCMV gB protein and the pentamer had the wild type sequences, and the gB-pentamer constituent protein fusion body can be expressed with the original structure of especially the pentamer portion maintained by further introducing suitable mutations into the HCMV gB protein or the pentamer.

Example 3-1

<Antigen Preparation>

It was shown by the examination of Example 2 that three gB-pentamer constituent protein fusion body expression plasmids in which mutations were introduced into the regions corresponding to the HCMV gB proteins or the pentamers were able to be coexpressed in combination to express the gB-pentamer constituent protein fusion bodies with the structures as gB and the pentamer maintained. Therefore, the following gB-pentamer constituent protein fusion body expression plasmids were further designed for coexpressing three or more proteins among the HCMV gB proteins, or the constituent proteins of the pentamer, or the gB-pentamer constituent protein fusion bodies in combination.

gH (SEQ ID NO: 4) cloned into pCAGGS1-dhfr-neo was referred to as gH(His-). A DNA fragment encoding gL (SEQ ID NO: 5) to which the C144S amino acid substitution was added, cloned into pCAGGS1-dhfr-neo was referred to as gL(C144S).

gBVC37 or gBΔd4 was added to the C-terminus side of gL (SEQ ID NO: 5) through a linker of 15 amino acids (GGGGSGGGGSGGGGS) (SEQ ID NO: 23). Among these, a gB-pentamer constituent protein fusion body in which the C-terminus side was gBVC37 was referred to as gL-VC37-L15aa, a gB-pentamer constituent protein fusion body in which the C-terminus side was Δd4 was referred to as gL-Δd4, and DNA fragments encoding the gB-pentamer constituent protein fusion bodies were prepared by PCR and cloned into pCAGGS1-dhfr-neo.

gBVC37 was connected with the C-terminus side of UL128 (SEQ ID NO: 6), or UL130 (SEQ ID NO: 7) or UL131 (SEQ ID NO: 8) through a linker of 15 amino acids (GGGGSGGGGSGGGGS) (SEQ ID NO: 23). Among these, the gB-pentamer constituent protein fusion body in which the N-terminus side was UL128 was referred to as UL128-VC37-L15aa, the gB-pentamer constituent protein fusion body in which the N-terminus side was UL130 was referred to as UL130-VC37-L15aa, the gB-pentamer constituent protein fusion body in which the N-terminus side was UL131 was referred to as UL131-VC37-L15aa, and DNA fragments encoding the gB-pentamer constituent protein fusion bodies were cloned into pCAGGS1-dhfr-neo.

These various gB-pentamer constituent protein fusion body expression plasmids were coexpressed in combination. The combinations of the expression plasmids were a total of 31 sets shown in Table 1. The expression was performed by the same method as for the HCMV gB protein to obtain culture supernatants of gB-pentamer constituent protein fusion bodies. The purification was conducted by the same method as for the HCMV gB protein to obtain purified products of the gB-pentamer constituent protein fusion bodies.

TABLE 1

UL128(C162S)-VC37/UL130-VC37/UL131-VC37
UL128(C162S)-VC37/UL130/UL131
gH(His-)/gL(C144S)/UL128(C162S)-VC37/UL130-VC37/UL131-VC37
gH(His-)/gL/UL128/UL130-VC37/UL131
UL128(C162S)-Δd4/UL130-Δd4/UL131-Δd4
UL128(C162S)-Δd4/UL130/UL131
gH(His-)/gL(C144S)/UL128(C162S)-Δd4/UL130-Δd4/UL131-Δd4
gH(His-)/gL/UL128/UL130-Δd4/UL131
UL128(C162S)-Δd4/UL130/UL131/Δd4
UL128(C162S)/UL130-Δd4/UL131/Δd4
UL128(C162S)/UL130/UL131-Δd4/Δd4
gH(His-)/gL/UL128/UL130-VC37/UL131/VC37
gH(His-)/gL/UL128/UL130/UL131-VC37/VC37
gH(His-)/gL/UL128/UL130-VC37/UL131
gH(His-)/gL(C144S)/UL128(C162S)-Δd4/UL130/UL131/Δd4
gH(His-)/gL/UL128/UL130-Δd4/UL131/Δd4
gH(His-)/gL/UL128/UL130/UL131-Δd4/Δd4
gH(His-)/gL(C144S)/UL128(C162S)-Δd4/UL130/UL131
gH(His-)/gL/UL128/UL130-Δd4/UL131
gH(His-)/gL/UL128/UL130/UL131-Δd4
gH(His-)/gL-VC37-L15aa/UL128-VC37-L15aa/UL130-VC37-L15aa/UL131

TABLE 1-continued gH(His-)/gL-VC37-L15aa/UL128-VC37-L15aa/UL130/
UL131-VC37-L15aa
gH(His-)/gL-VC37-L15aa/UL128/UL130-VC37-L15aa/
UL131-VC37-L15aa
gH(His-)/gL-Δd4/UL128(C162S)-Δd4/UL130-Δd4/UL131
gH(His-)/gL-Δd4/UL128(C162S)-Δd4/UL130/UL131-Δd4
gH(His-)/gL-Δd4/UL128/UL130-Δd4/UL131-Δd4
UL128-VC37-L15aa/UL130-VC37-L15aa/UL131-VC37-L15aa
gBv9
pentamer
gBVC37
gBΔd4

<Reactivity Analysis Using Serum>

The reactivities of the culture supernatants or the purified products of the acquired gB-pentamer constituent protein fusion bodies with various immune sera (binding activities) were evaluated by the same method as in Example 2. However, this experiment is different from Example 2 in that the culture supernatants diluted 100 times are used, and if tests are performed using the purified products instead of the culture supernatants, the purified products are reacted with solid phase antibodies at 1 μg/mL.

The results of the evaluation are shown in FIGS. 6 to 9. First, it was confirmed from the results of FIGS. 6 to 9 that the reactivity with the pentamer immune serum was first improved in gH(His-)/gL(C144S)/UL128(C162S)-VC37/UL130-VC37/UL131-VC3 7 as compared with UL128(C162S)-VC37/UL130-VC37/UL131-VC37, and the reactivity with the pentamer immune serum was improved in gH(His-)/gL(C144S)/UL128(C162S)-Δd4/UL130-Δd4/UL131-Δd4 as compared with UL128(C162S)-Δd4/UL130-Δd4/UL131-Δd4. It is considered from this that the gB-pentamer constituent protein fusion body easily takes the original structure of the pentamer by incorporating gH and gL.

It was observed that the reactivity with the pentamer serum was low in UL128(C162S)-VC37/UL130/UL131 as compared with UL128(C162S)-VC37/UL130-VC37/UL131-VC37, the reactivity with the pentamer serum was low in UL128(C162S)-Δd4/UL130/UL131 as compared with UL128(C162S)-Δd4/UL130-Δd4/UL131-Δd4, and the reactivity with the pentamer serum was low in gH(His-)/gL(C144S)/UL128(C162S)-Δd4/UL130/UL131 as compared with gH(His-)/gL(C144S)/UL128(C162S)-Δd4/UL130-Δd4/UL131-Δd4. It was considered from this that at least three molecules of the pentamer constituent molecules should have been expressed as gB-pentamer constituent protein fusion bodies.

It was observed that the reactivity was low in UL128(C162S)-Δd4/UL130/UL131/Δd4, UL128(C162S)/UL130-Δd4/UL131/Δd4, and UL128(C162S)/UL130/UL131-Δd4/Δd4 as compared with UL128 (C162S)-Δd4/UL130-Δd4/UL131-Δd4. It is considered from this that it is not effective to coexpress gB not fused with a pentamer constituent protein for making the pentamer portion form a natural structure in the gB-pentamer constituent protein fusion body.

It was observed that gH(His-)/gL-Δd4/UL128(C162S)-Δd4/UL130-Δd4/UL131, gH(His-)/gL-Δd4/UL128(C162S)-Δd4/UL130/UL131-Δd4, and gH(His-)/gL-Δd4/UL128/UL130-Δd4/UL131-Δd4 had high reactivities with the gBv9 immune serum and the pentamer immune sera as compared with gH(His-)/gL-VC37-L15aa/UL128-VC37-L15aa/UL130-VC37-L15aa/U L131, gH(His-)/gL-VC37-L15aa/UL128-VC37-L15aa/UL130/UL131-VC37-L15aa, and gH(His-)/gL-VC37-L15aa/UL128/UL130-VC37-

L15aa/UL131-VC37-L15aa, and gH(His-)/gL-Δd4/UL128(C162S)-Δd4/UL130-Δd4/UL131 had high reactivity with the gBv9 immune serum and the pentamer immune serum as compared with gH(His-)/gL-Δd4/UL128(C162S)-Δd4/UL130/UL131-Δd4 and gH(His-)/gL-Δd4/UL128/UL130-Δd4/UL131-Δd4. It is considered from this that if gB-pentamer constituent protein fusion bodies were expressed using any of UL128, UL130, and UL131 as a molecule not fused with gB, gB and the pentamer were expressed as structures similar to the natural structures by changing the gB portion into the Δd4 type, and especially if UL131 was a molecule not fuse with gB, the tendency is remarkable with respect to the structure of the pentamer.

<Gel Filtration Chromatography of Protein Purified Product>

The properties of the acquired purified products were evaluated by gel filtration chromatography. First, 50 μL of each purified product at a concentration of 100 μg/mL was applied using a Superdex200 Increase 5/150 GL (General Electric Company) as the column. The absorbance at a wavelength of 280 nm was measured at a flow rate of 0.4 mL/min, using D-PBS (FUJIFILM Wako Pure Chemical Corporation) as the migration buffer.

The results of the evaluation are shown in FIGS. 10 to 13. It was confirmed that the content of substances except aggregates was high in a combination in which a gB-pentamer constituent protein fusion body in which one pentamer constituent molecule of the pentamer constituent proteins was fused with VC37 or Δd4 as gB, the other four pentamer constituent proteins, and VC37 or Δd4 not fused with a pentamer constituent protein were coexpressed (FIG. 10), but aggregates were the main peak in a combination in which a gB-pentamer constituent protein fusion body in which one pentamer constituent molecule of the pentamer constituent proteins was fused with VC37 or Δd4 as gB and the other four pentamer constituent proteins were coexpressed (VC37 or Δd4 not fused with a pentamer constituent protein was not coexpressed) (FIG. 11(*b*)). If three pentamer constituent molecules of the pentamer constituent proteins were fused with gB, it was observed that the content of substances except aggregates tended to be high (FIGS. 11 to 13), but in the case of gH(His-)/gL-Δd4/UL128/UL130-Δd4/UL131-Δd4 (FIG. 13(*b*)), aggregates were a main peak.

<Antibody Titer Measurement>

Immunization against the acquired gB-pentamer constituent protein fusion bodies was performed by the same method as in Example 2 to acquire immune sera. The biding antibody titer and the neutralizing antibody titer to the gB protein of HCMV and the pentamer were evaluated using these sera.

In order to evaluate the binding antibody titers, gBv9 or the pentamer was first diluted with PBS (FUJIFILM Wako Pure Chemical Corporation) to 1 μg/mL, and 100 μL of the dilution was poured into a MaxiSorp plate (Nunc) and left to stand at 4° C. overnight to immobilize an antigen. After the immobilization, the plate was washed with PBS, 1% BSA/PBS solution was added in 300 μL/well, and the mixture was left to stand for 1 hour or more for blocking. The 1% BSA/PBS solution was discarded after the blocking, and the serum serially diluted with 1% BSA/PBS solution was added in 100 gL/well, the mixture was left to stand at room temperature for 1 hour and washed with PBST. Next, 100 μL/well of HRP-Rabbit anti Guinea Pig IgG(H+L) (invitrogen: 614620) 5000 times diluted with 1% BSA/PBS solution was added thereto, the mixture was left to stand at room temperature for 1 hour and then washed with PBST. Subsequently, 100 μL/well of TMB (sigma: T4444) was added thereto, the mixture was left to stand room temperature for 30 minutes, 1 N sulfuric acid was then added to stop the reaction, and the color development value (O.D. 450 nm/650 nm) was measured with a microplate reader (Molecular Devices, LLC.).

The results are shown in FIG. 14. It was considered from the results of FIG. 14 that since a gB-binding antibody (FIG. 14(*a*)) and a pentamer-binding antibody (FIG. 14(*b*)) were confirmed in serum of guinea pigs immunized against gH(His-)/gL-VC37-L15aa/UL128-VC37-L15aa/UL130-VC37-L15aa/U L131 and gH(His-)/gL-Δd4/UL128(C162S)-Δd4/UL130-Δd4/UL131, both gB-pentamer constituent protein fusion bodies could induce the gB antibody and the pentamer antibody by immunization as vaccine antigens.

A fibroblast neutralization test was subsequently performed using MRC-5 cells, and an epithelial cells neutralization test was performed using ARPE-19 cells to evaluate the neutralizing antibody titer. In the fibroblast neutralization test, HCMV the strain AD-169 subcultured in MRC-5 cells was used as a virus for the test, and in the epithelial cell neutralization test, HCMV the strain AD-169 subcultured in ARPE-19 cells was used as a virus for the test.

The fibroblast neutralization test was performed in the following procedure using MRC-5. First, an MRC-5 suspension was provided, and $2 \times 10^4$ cells/well were seeded in a CellCarrier-96 (PerkinElmer Japan Co., Ltd.: 6055700) and cultured in a $CO_2$ incubator at a $CO_2$ concentration of 5% and 37° C. overnight. On the next day, the immune serum was diluted with culture medium for diluting viruses (MEM medium containing 10 mM HEPES, 0.21% BSA, and penicillin-streptomycin), and HCMV the strain AD-169 was added thereto so that the final concentration was 200 $TCID_{50}$/mL, and the mixture was left to stand at 37° C. for one hour to prepare virus-serum mixed liquid. At this time, virus liquid not containing immune serum was prepared as a positive control similarly. The cultured MRC-5 cells were washed with PBS, 30 μL/well of the virus-serum mixed liquid or the virus liquid was added, and the mixture was then centrifuged at room temperature and 400 g for 30 minutes. Then, the virus-serum mixed liquid or the virus liquid was removed, the residue was washed with MEM medium containing penicillin-streptomycin, 100 μL/well of the same culture medium was then added for culture in a $CO_2$ incubator at a $CO_2$ concentration of 5% and 37° C. overnight. The cells were washed with the same culture medium on the next day, and 100 μL/well of 50% acetone/PBS solution was added, and the mixture was left to stand at room temperature for 20 minutes. Then, the 50% acetone/PBS solution was removed, the residue was washed with 0.5% BSA/PBS solution, 100 μL/well of 0.1% Triton X-100/PBS solution was then further added, and the mixture was left to stand at room temperature for 10 minutes. The mixture was then washed with 0.5% BSA/PBS solution again, and 100 μL/well of a CMV pp72/86 antibody (Santa Cruz Biotechnology, Inc.: sc-69748) 100 times diluted with 0.5% BSA/PBS solution was added, and the mixture was left to stand at 37° C. for 1 hour. This was washed with 0.5% BSA/PBS solution, 100 μL/well of stain solution in which Goat Anti-Mouse IgG H & L (Alexa Fluor488) (Abcam plc.: abl50113) was diluted to a final concentration of 1000 times, and Hoechst 33342 (DOJINDO LABORATORIES: 346-07951) was diluted to a final concentration of 500 times with 0.5% BSA/PBS solution was added, and the mixture was left to stand at room temperature for 1 hour. This was washed with 0.5% BSA/PBS solution to prepare a measurement sample. The measurement was conducted in Image Express Micro (Molecular Devices, LLC.), the total cell count was counted by Hoechst staining, the HCMV-infected cell count was counted by Alexa Fluor staining, the infection rate was calculated by (HCMV-infected cell count)/(total cell count). Furthermore, the infection inhibition rate (%) was calculated by defining the infection inhibition rate as 1−(infection rate of test well)/(infection rate of positive control). These results are shown in FIG. 15(*a*). It was shown from these results that the neutralizing antibody in response to the invasion of fibroblasts by HCMV was able to be induced by administering the gB-pentamer constituent protein fusion body.

The epithelial cell neutralization test was performed in almost the same procedure as the fibroblast neutralization test using ARPE-19. However, the epithelial cell neutralization test is different from the fibroblast neutralization test in that HCMV the strain AD-169 subcultured and conditioned in ARPE-19 cells was used as a virus, and virus serum mixed liquid or virus liquid containing this at a final concentration of $7\text{-}8 \times 10^4$ $TCID_{50}$/mL was used. The results are shown in FIG. 15(*b*). It was shown that the neutralizing antibody in response to the invasion of epithelial cells by HCMV was able to be induced by administering the gB-pentamer constituent protein fusion body.

Example 3-2-1

<Antigen Preparation>

Since it was shown by the examination of Example 3-1 that even though five of the various gB-pentamer constituent protein fusion body expression plasmids were coexpressed in combination, each of the gB-pentamer constituent protein fusion bodies maintained structures as the gB and the pentamers, the following gB-pentamer constituent protein fusion body expression plasmids were designed to further investigate the influence of the point mutations of C144 of gL and C162 of UL128 carefully. A DNA fragment encoding a fusion protein in which the C144S amino acid substitution was added to gL (SEQ ID NO: 5), a linker of 15 amino acids (GGGGSGGGGSGGGGS) (SEQ ID NO: 23) and Δd4 were added to the C-terminus side was prepared by PCR, and the DNA fragment cloned into pCAGGS1-dhfr-neo was referred to as gL(C144S)-Δd4. Various gB-pentamer constituent protein fusion body expression plasmids was coexpressed in combination at the time of expression. The combined expression plasmids were a total of three sets that were gH(His-)/gL-Δd4/UL128-Δd4/UL130-Δd4/UL131, gH(His-)/gL(C144S)-Δd4/UL128(C162S)-Δd4/UL130-Δd4/UL131, and gH(His-)/gL-Δd4/UL128(C162S)-Δd4/UL130-Δd4/UL131. The purification was conducted by the same method as for the HCMV gB protein to obtain purified products of gB-pentamer constituent protein fusion bodies.

<Immunization>

Guinea pigs (Hartley) were immunized against gBΔd4, or the pentamer, or gH(His-)/gL-Δd4/UL128(C162S)-Δd4/UL130-Δd4/UL131, or saline by the same method as in Example 2 to obtain gBΔd4 immune serum, and pentamer immune serum, and gH(His-)/gL-Δd4/UL128(C162S)-Δd4/UL130-Δd4/UL131 immune serum, and saline immune serum.

<Reactivity Analysis Using Serum>

The reactivities of the acquired gB-pentamer constituent protein fusion bodies with gBΔd4, pentamer (PC), gH(His-)/gL-Δd4/UL128(C162S)-Δd4/UL130-Δd4/UL131(Δd4/PC), and saline immune sera (binding activities) were evaluated by the same method as in Example 2. These are shown in FIGS. 16 to 19. It was suggested from these results that the point mutations of C144 of gL and C162 of UL128 did not influence the reactivity with the sera.

<Gel Filtration Chromatography of Protein Purified Products>

The properties of the purified products of the acquired gH(His-)/gL-Δd4/UL128-Δd4/UL130-Δd4/UL131 and gH(His-)/gL(C144S)-Δd4/UL128(C162S)-Δd4/UL130-Δd4/UL131 were evaluated by gel filtration chromatography. Then, 50 μL of each purified product at a concentration of 100 μg/mL was applied using a Superdex200 Increase 5/150 GL (General Electric Company) as the column. The absorbance at a wavelength of 280 nm was detected at a flow rate of 0.4 mL/min, using D-PBS (FUJIFILM Wako Pure Chemical Corporation) as the migration buffer. The results are shown in FIG. 20. It was shown from these results and FIG. 12 (d) that the point mutation introduction into C144 of gL and C162 of UL128 did not change the separation pattern by gel filtration chromatography.

<Particle Size Evaluation of Protein Purified Products>

The particle size distributions of the acquired gH(His-)/gL-Δd4/UL128-Δd4/UL130-Δd4/UL131, gH(His-)/gL(C144S)-Δd4/UL128(C162S)-Δd4/UL130-Δd4/UL131, gH(His-)/gL-Δd4/UL128(C162S)-Δd4/UL130-Δd4/UL131 fusion proteins were evaluated by dynamic light scattering. Each recombinant protein was diluted with PBS (SIGMA) to 0.2 or 0.3 mg/mL, and particle size analysis was performed by a Zetasizer Nano ZS (Malvern Panalytical Ltd.). A quartz cell was used for measurement, and the measurement condition was a temperature of 25.0° C. These are shown in FIG. 21. The peaks of FIGS. 21(a), (b), and (c) show three results, and the numbers shown in the tables are the average values of three measurements. It was shown from these results that the point mutation introduction into C144 of gL and C162 of UL128 did not influence the particle size distributions.

Example 3-2-2

<Antigen Preparation>

Various gB-pentamer constituent protein fusion body expression plasmids were coexpressed in combination. The combined expression plasmids were a total of two sets that were gH(His-)/gL/UL128(C162S)-Δd4/UL130-Δd4/UL131-Δd4 and gH(His-)/gL/UL128-Δd4/UL130-Δd4/UL131-Δd4. The purification was conducted by completely the same method as for the gB protein of HCMV to obtain protein purified products.

<Gel Filtration Chromatography of Protein Purified Products>

The properties of the acquired purified products were evaluated by gel filtration chromatography. Then, 50 μL of each purified product at a concentration of 100 μg/mL was applied using a Superdex200 Increase 5/150 GL (General Electric Company) as the column. The absorbance at a wavelength of 280 nm was detected at a flow rate of 0.4 mL/min, using D-PBS (FUJIFILM Wako Pure Chemical Corporation) as the migration buffer. The results are shown in FIG. 28. It was shown from these results that the point mutation introduction into C162 of UL128 did not change the elution positions of the peaks by gel filtration chromatography.

<Particle Size Evaluation of Protein Purified Products>

The particle size distributions of the acquired gH(His-)/gL/UL128(C162S)-Δd4/UL130-Δd4/UL131-Δd4 and gH(His-)/gL/UL128-Δd4/UL130-Δd4/UL131-Δd4 fusion proteins were evaluated by dynamic light scattering. Each recombinant protein was diluted with PBS (SIGMA) to 0.2 or 0.3 mg/mL, and particle size analysis was performed by a Zetasizer Nano ZS (Malvern Panalytical Ltd.). A quartz cell was used for measurement, and the measurement condition was a temperature of 25.0° C. These is shown in FIG. 29. The peaks of FIG. 29 show three results, and the numbers shown in the tables are the average values of three measurements. It was shown from these results that the point mutation introduction into C162 of UL128 did not influence the particle size distribution.

Example 3-2-3

<Antigen Preparation>

Various gB-pentamer constituent protein fusion body expression plasmids were coexpressed in combination. The combined expression plasmids were a total of four sets that were gBv9, the pentamer, gH(His-)/gL-Δd4/UL128-Δd4/UL130-Δd4/UL131, and gH(His-)/gL/UL128-Δd4/UL130-Δd4/UL131-Δd4. The purification was conducted by completely the same method as for the gB protein of HCMV to obtain protein purified products.

<Immunization>

Guinea pigs (Hartley) were immunized against gBv9, the pentamer, gH(His-)/gL-Δd4/UL128-Δd4/UL130-Δd4/UL131, gH(His-)/gL/UL128-Δd4/UL130-Δd4/UL131-Δd4, or saline by the same method as in Example 2 to obtain gBv9 immune serum, pentamer immune serum, gH(His-)/gL-Δd4/UL128(C162S)-Δd4/UL130-Δd4/UL131 immune serum, gH(His-)/gL-Δd4/UL128-Δd4/UL130-Δd4/UL131 immune serum, gH(His-)/gL/UL128-Δd4/UL130-Δd4/UL131-Δd4 immune serum, and saline immune serum.

<Binding Antibody Titer Measurement Using Sera>

The reactivities of the acquired gB-pentamer constituent protein fusion bodies with the gBv9 immune serum, the pentamer immune serum, the gH(His-)/gL-Δd4/UL128-Δd4/UL130-Δd4/UL131 immune serum, the gH(His-)/gL/UL128-Δd4/UL130-Δd4/UL131-Δd4 immune serum, and the saline immune serum (binding activities) were evaluated by the method as in Example 2. The evaluation results of the binding antibody titers are shown in FIG. 30. It was considered from these results that the gB antibody and the pentamer antibody were able to be induced by administering a gB-pentamer constituent protein fusion body.

<Neutralizing Antibody Titer Measurement Using Sera>

The neutralizing antibody titer was evaluated using the acquired gBv9 immune serum, pentamer immune serum, gH(His-)/gL-Δd4/UL128-Δd4/UL130-Δd4/UL131 immune serum, gH(His-)/gL/UL128-Δd4/UL130-Δd4/UL131-Δd4 immune serum, and saline immune serum by the same method as in Example 3-1. However, this experiment was different from Example 3-1 in that HCMV the strain AD-169 subcultured and conditioned in ARPE-19 cells was used as the virus for both fibroblast neutralization test using MRC-5 cells and epithelial cell neutralization test using ARPE-19 cells. The evaluation results of the neutralizing antibody titer are shown in FIG. 31.

Since the gB-binding antibody (FIG. 30(a)) and the pentamer-binding antibody (FIG. 30(b)) were confirmed in gH(His-)/gL-Δd4/UL128-Δd4/UL130-Δd4/UL131 immune serum and gH(His-)/gL/UL128-Δd4/UL130-Δd4/UL131-Δd4 immune serum from FIG. 30, it was considered that both gB-pentamer constituent protein fusion bodies was able to induce the anti-gB antibody and the anti-pentamer antibody by immunization against the fusion bodies as the vaccine antigens. It was shown from FIG. 31 that gH(His-)/gL-Δd4/UL128-Δd4/UL130-Δd4/UL131 and gH(His-)/gL/UL128-Δd4/UL130-Δd4/UL131-Δd4 were able to induce the neutralizing antibody in response to the invasion of the fibroblasts and the epithelial cells by HCMV by administering gH(His-)/gL-Δd4/UL128-Δd4/UL130-Δd4/UL131 and gH (His-)/gL/UL128-Δd4/UL130-Δd4/UL131-Δd4 that were gB-pentamer constituent protein fusion bodies.

Example 4

<Stability Evaluation of gB-Pentamer Fusion Proteins>

Various gB-pentamer constituent protein fusion body expression plasmids were coexpressed in combination. The combined expression plasmids were a total of six sets that were gBv9, the pentamer, gH(His-)/gL-Δd4/UL128 (C162S)-Δd4/UL130-Δd4/UL131, gH(His-)/gL/UL128 (C162S)-Δd4/UL130-Δd4/UL131-Δd4, gH(His-)/gL/ UL128-Δd4/UL130-Δd4/UL131-Δd4, and gH(His-)/gL- Δd4/UL128-Δd4/UL130-Δd4/UL131. The purification was conducted by completely the same method as for the gB protein of HCMV to obtain protein purified products.

The stabilities of the acquired recombinant gB, recombinant pentamer, mixture of equal amounts of the recombinant gB and the recombinant pentamer, and the recombinant gB-pentamer constituent protein fusion bodies were evaluated by dynamic light scattering. Each recombinant protein was diluted with PBS (SIGMA) to 0.2 mg/mL, and an accelerated test was performed by leaving the protein to stand at 37° C. for 0 days, 1 day, 3 days, and 7 days. At this time, a protease inhibitor (FUJIFILM Wako Pure Chemical Corporation, 165-26021) was added to the protein to be left to stand for 1 day or more in $\frac{1}{100}$ times the amount thereof, and each protein after the test was analyzed for the particle size with a Zetasizer Nano ZS (Malvern Panalytical Ltd.). A quartz cell was used for measurement, and the measurement condition was a temperature of 25.0° C. In the obtained particle size distribution, particles having particle sizes (<100 nm) and considered to be targets were defined as "single particles", particles that were larger than the targets and had particle sizes of less than 1,000 nm were defined as "aggregation (small)", and particles having particle sizes of more than 1,000 nm were defined as "aggregation (large)".

Figure 32:
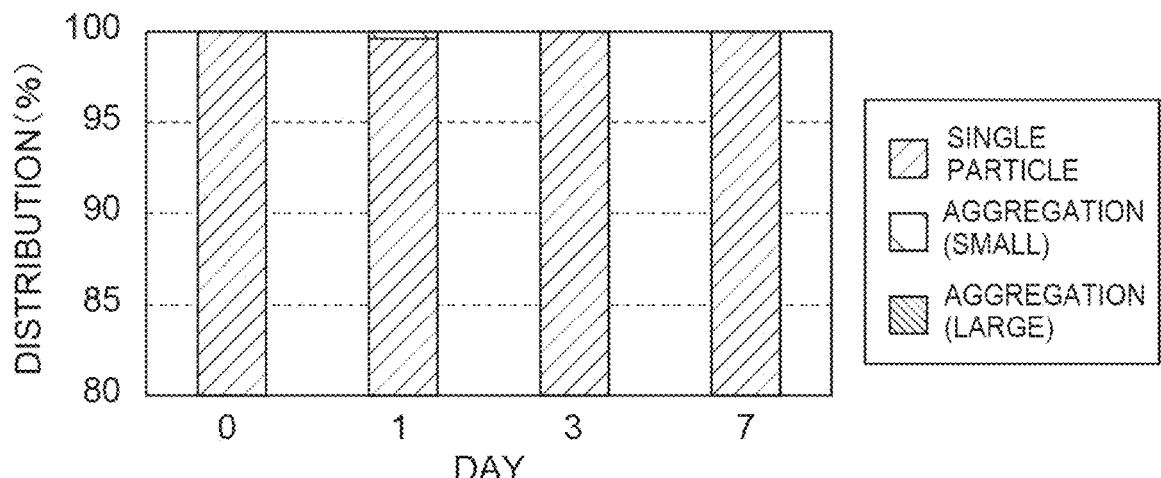
FIG. 32 is a figure showing the results of the particle size distribution of purified products of gH(His-)/gL-Δd4/UL128-Δd4/UL130-Δd4/UL131 of Example 4.

Figures that indicate the distribution of the particles are shown in FIGS. 22, 23, and 32. Although it is observed from these results that the pentamer increased in the content of the aggregation (large) over time, most of gH(His-)/gL-Δd4/ UL128(C162S)-Δd4/UL130-Δd4/UL131, gH(His-)/gL/ UL128(C162S)-Δd4/UL130-Δd4/UL131-Δd4, gH(His-)/ gL/UL128-Δd4/UL130-Δd4/UL131-Δd4, and gH(His-)/gL- Δd4/UL128-Δd4/UL130-Δd4/UL131 remained monomers. It was made clear from this that, in gH(His-)/gL-Δd4/UL128 (C162S)-Δd4/UL130-Δd4/UL131, gH(His-)/gL/UL128 (C162S)-Δd4/UL130-Δd4/UL131-Δd4, gH(His-)/gL/ UL128-Δd4/UL130-Δd4/UL131-Δd4, and gH(His-)/gL- Δd4/UL128-Δd4/UL130-Δd4/UL131, the stabilities were improved as compared with the pentamer.

Example 5

<Antigen Preparation>

As stimulating antigens, gBv9, the pentamer, gH(His-)/ gL-Δd4/UL128(C162S)-Δd4/UL130-Δd4/UL131, gH(His-)/gL-Δd4/UL128-Δd4/UL130-Δd4/UL131, and gH(His-)/gL/UL128-Δd4/UL130-Δd4/UL131-Δd4 were expressed and purified in the same procedure as in Example 4.

<Cellular Immunity Evaluation>

The cellular immunity evaluation using human PBMCs was performed by an ELISpot assay using Human IFN-γ

ELISpot$^{PLUS}$ (Mabtech AB, 3420-4HST-2). Human PBMCs of 23 donors in whom IFNγ induction was observed in response to HCMV antigen-stimulation among products produced by CTL INC. were selected.

CTL Anti-Aggregate Wash (20×) (CTL INC.) was warmed in a water bath set at 37° C. for 10 min and thawed, and diluted with RPMI-1640 to prepare CTL Anti-Aggregate Wash (1×), and the CTL Anti-Aggregate Wash (1×) was left to stand in a $CO_2$ incubator at 37° C. for 20 min or more until use. L-Glutamine (100×) was added to CTL-Test medium at 1% by volume, and the CTL-Test medium was left to stand in a $CO_2$ incubator at 37° C. for 20 min or more. A vial containing the PBMCs was warmed in a water bath at 37° C. for 8 min, and after the thawing, the CTL Anti-Aggregate Wash (1×) was gently added to prepare a cell solution. The cell solution was centrifuged (330 g, 10 min, RT) for the removal of the supernatant, 10 mL of CTL Anti-Aggregate Wash (1×) was then added, the cell solution was centrifuged (330 g, 10 min, RT) again for the removal of the supernatant, and the residue was then diluted with CTL-Test medium left to stand in the $CO_2$ incubator at 37° C. and used for an ELISPOT assay.

A necessary number of the strip of Human IFN-γ ELISpot$^{PLUS}$ was washed with 200 μL/well of PBS four times, and 200 μL/well of the CTL-Test medium was added, and the mixture was left to stand at room temperature for 30 min or more. The CTL-Test medium was removed from the plate, 100 μL/well of the cell suspension was added, 100 μL/well of an antigen solution diluted to 2 μg/mL was then added, and the mixture was suspended. The plate was shaded from light, and static culture was performed in a $CO_2$ incubator at 37° C. and a $CO_2$ concentration of 5% for 12-48 hr. After the culture, the cells were removed with the culture medium, and the residue was washed with 200 μL/well of PBS five times. A detection antibody solution (7-6-1-biotin) attached to Human IFN-γ ELISpot$^{PLUS}$ was diluted with PBS-0.5% FBS to 1 μg/mL, and 100 μL/well of the dilution was added, and the mixture was left to stand at room temperature for 2 hr. After the reaction, the mixture was washed with 200 μL/well of PBS five times, and a labeled antibody solution (Streptavidin-HRP) attached to Human IFN-γ ELISpot$^{PLUS}$ was 1,000 times diluted with PBS-0.5% FBS, and 100 μL/well of the dilution was added, and the mixture was left to stand at room temperature for 1 hr. After the reaction, the mixture was washed with 200 μL/well of PBS five times, a TMB solution attached to Human IFN-γ ELISpot$^{PLUS}$ was passed through a 0.22 m filter in a necessary amount, and 100 μL/well of the filtered solution was added, the mixture was left to stand at room temperature until spots were observed clearly (about 5-30 min). The plate was washed with 200 μL/well of DW three times and then dried, and the number of the spots was counted with an ELISPOT counter.

Figure 24:
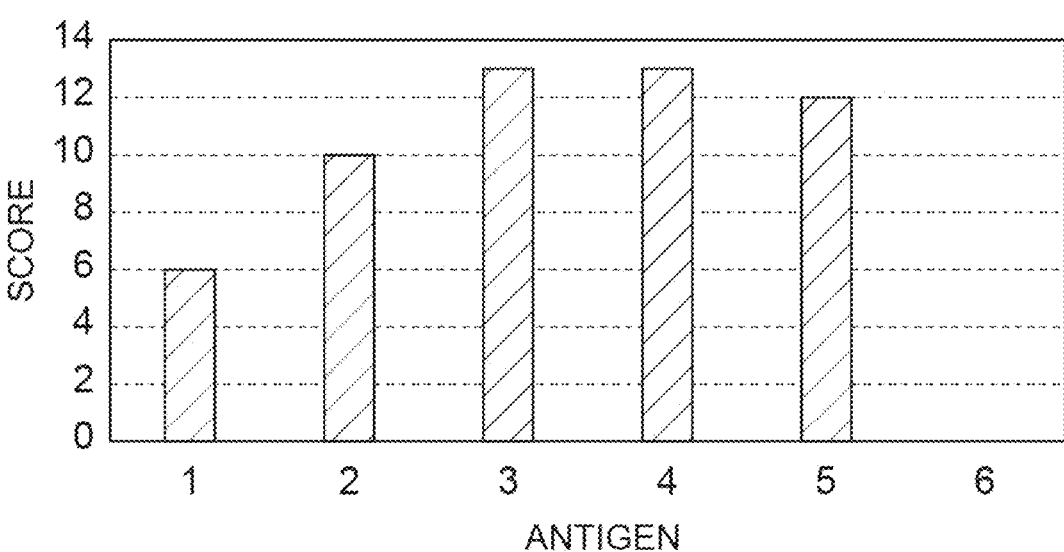
FIG. 24 is a figure showing the scores of purified products of the gB-pentamer constituent protein fusion bodies of Example 5.

The average value of the spot numbers of 2 wells was defined as the measurement result. As to only a negative control, the average value of the spot numbers of 4 wells was defined as the measurement result. If the average value of the spot numbers was more than 0 and less than 5, "0" was scored, if the average value was 5 or more and less than 50, "1" was scored, if the average value was 50 or more and less than 100, "2" was scored, if the average value was 100 or more, "3" was scored, and the scores of all the donors were totaled with respect to each antibody. The graph of this is shown in FIG. 24. It was considered from these results that IFNγ was produced more highly in gH(His-)/gL-Δd4/UL128 (C162S)-Δd4/UL130-Δd4/UL131, gH(His-)/gL-Δd4/

UL128-Δd4/UL130-Δd4/UL131, and gH(His-)/gL/UL128-Δd4/UL130-Δd4/UL131-Δd4 than in gBv9 and the pentamer.

Example 6

<Gpcmv-Gb Preparation>

Guinea pig cytomegalovirus (GPCMV), exhibiting infectiousness with respect to guinea pigs, was used for evaluation using a model system of the infection of guinea pigs via the placenta. Since the recombinant GPCMV gB protein may have contained aggregates, a modified GPCMV gB protein that did not contain aggregates and in which the properties were improved was prepared.

A gene encoding gB in which a signal sequence was added to an ectodomain (1-656aa) of gB derived from GPCMV the strain 22122, and amino acid mutation introduction was further performed for property improvement (SEQ ID NO: 17, 1-692aa; a GPCMV-gB ectodomain variant) was artificially synthesized and cloned into pCAGGS1-dhfr-neo. The gene was designed so that a His-tag of 9 amino acids (SEQ ID NO: 30) was added to the C-terminus of the gB. A Expi293 expression system (Life Technologies Corporation) was used for expression. Cells were transfected with the expression plasmid, and the culture supernatant was collected in 4 to 6 days. The GPCMV-gB ectodomain variant was purified from the culture supernatant containing the GPCMV gB using Ni NTA Agarose (QIAGEN) and dialyzed against PBS+0.5 M arginine to obtain a purified product of the ectodomain of the modified GPCMV gB protein (referred to as "GPCMV-gB") (International Application PCT/JP2019/047966).

<GPCMV Pentamer Preparation>

Then, an ectodomain of a pentamer derived from GPCMV the strain 22122 was prepared. Since there was no reported example with respect to the solubility expression of the ectodomain of the GPCMV pentamer, the design was performed with reference to a reported example of the solubility expression of the ectodomain of the HCMV pentamer (Non Patent Literature 14) as described below to construct an expression plasmid.

A gene encoding 1-698aa (SEQ ID NO: 18), which was an ectodomain in GP75 (SEQ ID NO: 10) of GPCMV, which was an orthologue of gH of HCMV, were artificially synthesized and cloned into pCAGGS1-dhfr-neo. The design was performed so that a His-tag of 9 amino acids (SEQ ID NO: 30) was added to the C-terminus of GP75. Furthermore, a gene encoding GP115 of GPCMV (1-258aa, SEQ ID NO: 11), which was an orthologue of gL of HCMV, a gene encoding GP129 of GPCMV (1-179aa, SEQ ID NO: 12), which was an ortholog of UL128 of HCMV, a gene encoding GP131 of GPCMV (1-192aa, SEQ ID NO: 13), which was an orthologue of UL130 of HCMV, and a gene encoding GP133 of GPCMV (1-127aa, SEQ ID NO: 14), which was an orthologue of UL131 of HCMV, were artificially synthesized separately and cloned into pCAGGS1-dhfr-neo. The above-mentioned five proteins were coexpressed. The expression and purification were conducted by the same method as for GPCMV-gB to obtain a purified product of an ectodomain of the GPCMV pentamer (hereinafter referred to as a "GPCMV pentamer") (International Application PCT/JP2019/047966).

<Preparation and Property Analysis of GPCMV-gB-Pentamer Fusion Proteins>

Then, a protein in which 111-475aa and 641-692aa of a GPCMV-gB ectodomain variant (SEQ ID NO: 17) were connected with each other via 9 amino acids that were GGGSGSGGG (SEQ ID NO: 20), and a His-tag sequence (SEQ ID NO: 30) was further added to the C-terminus thereof was referred to as GPCMV-Δd4 (SEQ ID NO: 32), and a DNA fragment encoding GPCMV-Δd4 was prepared by PCR, and the DNA fragment was cloned into pCAGGS1-dhfr-neo. A protein in which the His-tag was not added to the C-terminus of the gene encoding the ectodomain of GP75 was designed, a DNA fragment encoding the protein was prepared by PCR, and a vector in which the DNA fragment was cloned into pCAGGS1-dhfr-neo was referred to as GP75(His-).

Then, DNA fragments encoding fusion proteins in which GPCMV-Δd4 was connected with the C-terminus side of GP115, GP129, GP131, and GP133 via a linker of 15 amino acids (GGGGSGGGGSGGGGS) (SEQ ID NO: 23) were prepared based on the above-mentioned genes by PCR, respectively, and vectors in which the DNA fragments were cloned into pCAGGS1-dhfr-neo were referred to as GP115-Δd4, GP129-Δd4, GP131-Δd4, and GP133-Δd4, respectively. Various gB-pentamer constituent protein fusion body expression plasmids were coexpressed in combination at the time of expression. The combined expression plasmids were GP75 (His-)/GP115-Δd4/GP129-Δd4/GP131-Δd4/GP133 and GP75(His-)/GP115/GP129-Δd4/GP131-Δd4/GP133-Δd4. The expression and purification were performed by the same method as for GPCMV-gB.

When analysis was performed by the gel filtration chromatography (FIGS. 25(a) and (b)), peaks in GP75(His-)/GP115-Δd4/GP129-Δd4/GP131-Δd4/GP133 were confirmed at the same positions as peaks in gH(His-)/gL-Δd4/UL128-Δd4/UL130-Δd4/UL131 of HCMV (Example 3-2-1, FIG. 20(a)), and peaks in GP75(His-)/GP115/GP129-Δd4/GP131-Δd4/GP133-Δd4 were confirmed at the same positions as peaks in gH(His-)/gL/UL128-Δd4/UL130-Δd4/UL131-Δd4 of HCMV (Example 3-2-2, FIG. 28(b)).

<Preparation and Property Analysis of GPCMV-Δd4-ULs>

Then, a DNA fragment encoding a fusion protein in which GPCMV-Δd4 was connected with the C-terminus side of GP133 via a linker of 15 amino acids (GGGGSGGGGSGGGGS) (SEQ ID NO: 23) was prepared based on the above-mentioned gene by PCR, and a vector in which the DNA fragment was cloned into pCAGGS1-dhfr-neo was referred to as GP133-Δd4. A vector in which the C167S modification, considered to dissociate disulfide-binding sites of GP115 and GP129, was added based on GP129-Δd4 was referred to as GP129(C167S)-Δd4. Various gB-pentamer constituent protein fusion body expression plasmids were coexpressed in combination at the time of expression. The combined expression plasmids were GP129 (C167S)-Δd4/GP131-Δd4/GP133-Δd4. The expression and purification were conducted by the same method as for GPCMV-gB to obtain a purified product of GP129(C167S)-Δd4/GP131-Δd4/GP133-Δd4 (GPCMV-Δd4-ULs).

When analysis by gel filtration chromatography (FIG. 25(c)) was performed, peaks in GP129(C167S)-Δd4/GP131-Δd4/GP133-Δd4 were observed at the same position as peaks in UL128(C162S)-Δd4/UL130-Δd4/UL131-Δd4 of HCMV (Example 3-1, FIG. 11(c)).

<Test of Placenta Infection Prevention>

Hartley guinea pigs (female, 5 weeks old) were immunized against GPCMV-gB, the GPCMV pentamer, GP75 (His-)/GP115-Δd4/GP129-Δd4/GP131-Δd4/GP133, and GP129(C167S)-Δd4/GP131-Δd4/GP133-Δd4 (GPCMV-Δd4-ULs). Each antigen was prepared with physiological saline (Otsuka Pharmaceutical Co., Ltd.) to 0.0016 μg/animal, and 10 v/v % Alum (InvivoGen vac-alu250) and 50 μg/animal CpG ODN1826 were used as adjuvants. The prepared antigen solution was intramuscularly inoculated into each guinea pig (100 μL/foot, administered to both hind legs) twice at two-week interval, and the guinea pig was mated with a Hartley guinea pig (male, 9 weeks old or older) from two weeks after the two immunizations to produce a pregnant guinea pig. At this time, a PBS-administered group was also mated similarly. Then, 1×10⁶ pfu/animal of wild type GPCMV was subcutaneously administered to both immunized group and PBS group (saline group) at 4 weeks after pregnancy, and the placenta was collected after euthanasia with sodium pentobarbital 3 weeks after. The collected placenta was crushed with a gentleMACS (Miltenyi Biotec), and DNA was extracted with a *MagNA* Pure 96 (Roche Diagnostics K.K.). The GPCMV gp83 gene and the β-actin gene derived from the cells of the obtained DNA were quantitated with probes and primer sets shown in Table 2 (International Application PCT/JP2019/047966) using a 7500 Fast real-time PCR system (Thermo Fisher Scientific K.K.).

TABLE 2

Table 2 Primers and probes

|  | For detecting GPCMV GP83 | For detecting guinea pig β-actin |
|---|---|---|
| Forward primer | 5'-CGACGACGAC GATGACGAAAAC-3' (SEQ ID NO: 24) | 5'-TGGATCGGCGGCT CATC-3' (SEQ ID NO: 27) |
| Reverse primer | 5'-TCCTCGGTCTC AACGAAGGGTC-3' (SEQ ID NO: 25) | 5'-CATCGTACTCCTGC TTGCTGAT-3' (SEQ ID NO: 28) |
| FAM probe | 5'-FAM-ATCCGAG TTAGGCAGCG-MGB-3' (SEQ ID NO: 26) | 5'-FAM-CACTCTCCA CCTTCC-MGB-3' (SEQ ID NO: 29) |

Figure 26:
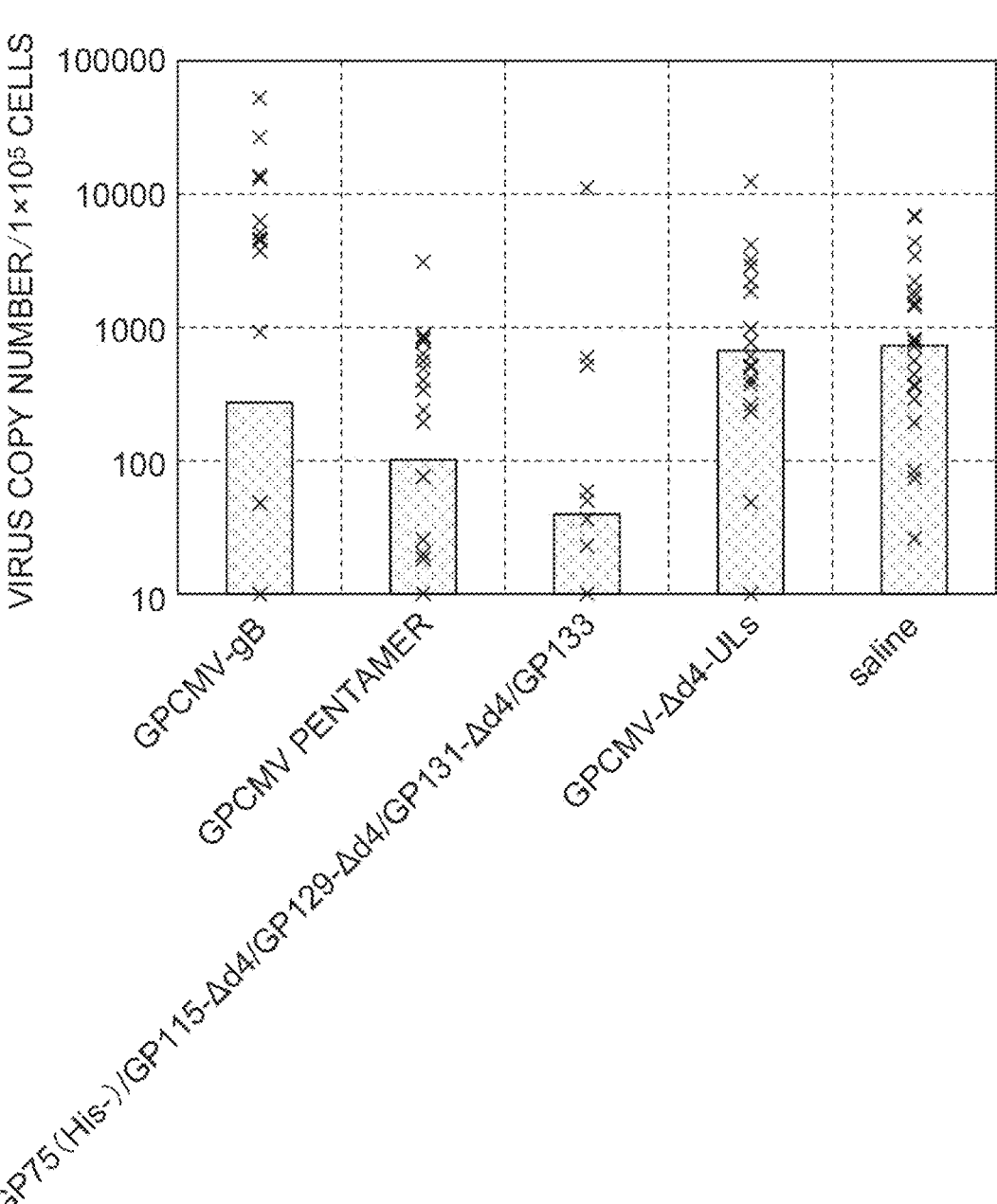
FIG. 26 is a figure showing the results of tests on the prevention of infection via the placenta with purified products of the gB-pentamer constituent protein fusion bodies of Example 6.

The numbers of gp83 genes per 10⁵ cells, namely the virus copy numbers, are shown in FIG. 26. At this time, the lower limit of detection was defined as 10 copies per 10⁵ cells. It was shown from the results of FIG. 26 that GP75(His-)/GP115-Δd4/GP129-Δd4/GP131-Δd4/GP133 had a higher ability to prevent infection than GPCMV-gB, the GPCMV pentamer, and GPCMV-Δd4-ULs.

Example 7

<Test of Prevention of Infection Via Placenta>
GPCMV-gB, the GPCMV pentamer, GP75(His-)/GP115-Δd4/GP129-Δd4/GP131-Δd4/GP133, and GP75(His-)/

GP115/GP129-Δd4/GP131-Δd4/GP133-Δd4 were expressed and prepared by the same method as in Example 6.

Hartley guinea pigs (female, 5 weeks old) were immunized against GPCMV-gB, the GPCMV pentamer, the mixing of GPCMV-gB and the GPCMV pentamer, GP75(His-)/GP115-Δd4/GP129-Δd4/GP131-Δd4/GP133, and GP75(His-)/GP115/GP129-Δd4/GP131-Δd4/GP133-Δd4 in a dose of 0.2 μg/animal and mated by the same method as in Example 6. As to the mixing of GPCMV-gB and the GPCMV pentamer, 0.1 μg of GPCMV-gB and 0.1 μg of the GPCMV pentamer were mixed to 0.2 μg/animal. At this time, a PBS-treated group was also mated similarly. Then, 1×10⁷ pfu/animal of the wild type GPCMV was subcutaneously administered to both immunized group and the PBS group (saline group) at 4 weeks after pregnancy for challenge. Three weeks after the challenge, the guinea pigs were euthanized with sodium pentobarbital, the mothers' bodies and the fetuses were then dissected, salivary glands and the placentae were collected from the mothers' bodies, and the pancreases were collected from the fetuses. The salivary glands and the placentae of the mothers' bodies were crushed with appropriate amounts of PBS using a gentleMACS (Miltenyi Biotec) separately. The pancreases of the fetuses were crushed with appropriate amounts of PBS with a FastPrep 24 (MP BIOMEDICALS.). DNAs were extracted from each of the homogenate liquids of the salivary glands and the placentae of the mothers' bodies, and the pancreases of the fetuses with a MagNA Pure 96 (Roche Diagnostics K.K.). The virus copy numbers per 10⁵ cells were quantitated from the obtained DNAs by the same method as in Example 6. At this time, the lower limit of detection was defined as 1 copy per 10⁵ cells.

Figure 27:
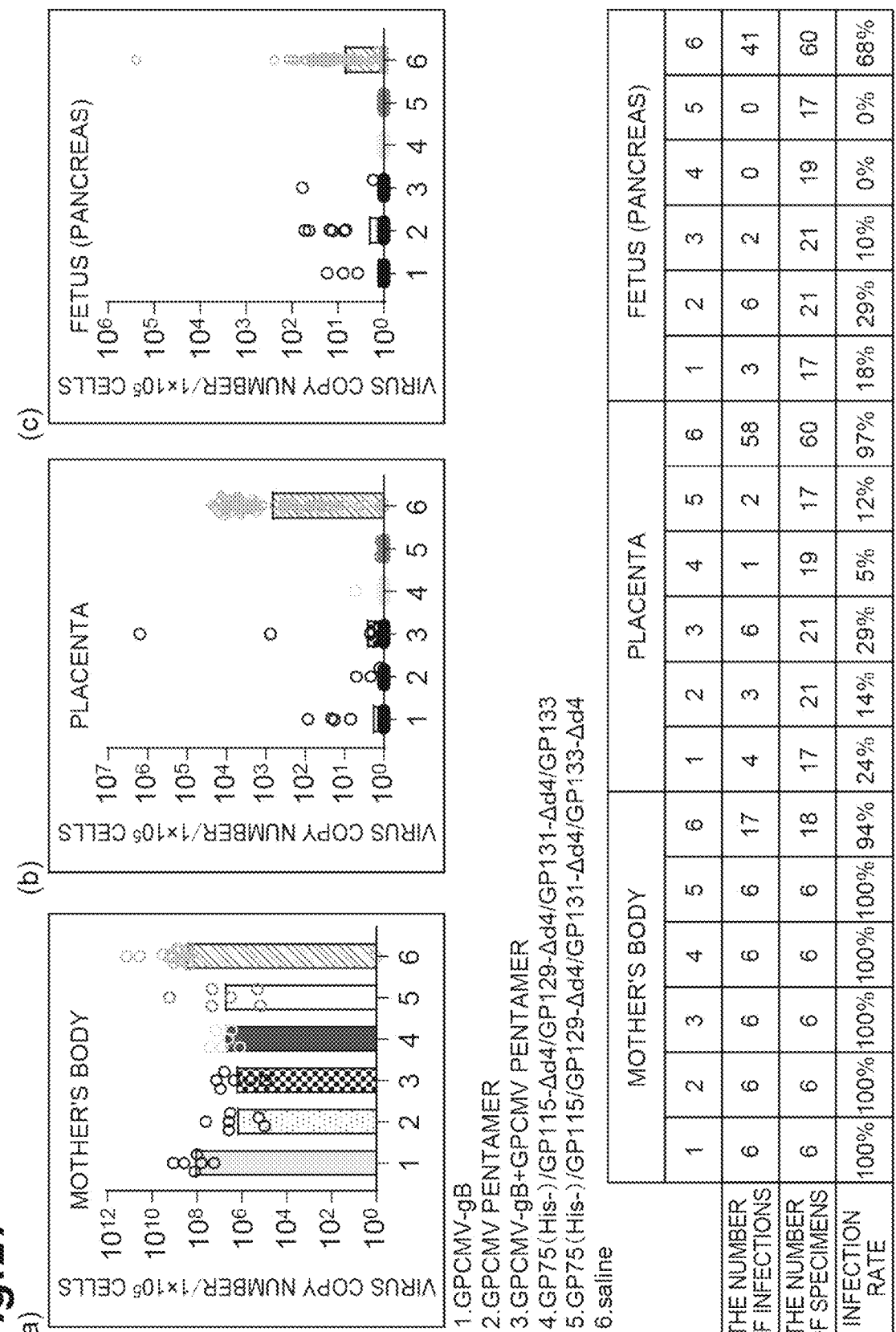
FIG. 27 is a figure showing the results of tests on the prevention of infection via the placenta with purified products of the gB-pentamer constituent protein fusion bodies of Example 7.

These results are shown in FIG. 27. In the immunized groups of GP75(His-)/GP115-Δd4/GP129-Δd4/GP131-Δd4/GP133 and GP75(His-)/GP115/GP129-Δd4/GP131-Δd4/GP133-Δd4, perfect infection prevention was confirmed in the fetuses. In the mothers' bodies and the placentae, a definite infection suppression effect was also seen. Since GP75(His-)/GP115-Δd4/GP129-Δd4/GP131-Δd4/GP133 and GP75(His-)/GP115/GP129-Δd4/GP131-Δd4/GP133-Δd4 exhibited effect on both mothers' bodies and fetuses, it was strongly suggested that the vaccine antigen of the present invention was useful for congenital infection prevention and also additionally effective in the prevention of cytomegalovirus infections in healthy persons, and transplant patients, AIDS patients, and the like.

The invention claimed is:
1. A fusion protein complex comprising:
three envelope glycoprotein B (gB proteins), and
a pentamer of cytomegalovirus (CMV) proteins,
wherein the fusion protein complex comprises three gB protein-CMV protein fusion proteins in which each of the three gB proteins is fused to a different CMV protein of the pentamer,
wherein the gB protein is an ectodomain of a gB protein having 90% or more sequence identity with an ectodomain of the gB protein consisting of the amino acid sequence set forth in SEQ ID NO: 15, SEQ ID NO: 16, SEQ ID NO: 3, or SEQ ID NO: 31, and
wherein the pentamer consists of the following CMV proteins:
a gH protein comprising a sequence having 90% or more sequence identity with SEQ ID NO: 4;
a gL protein comprising a sequence having 90% or more sequence identity with SEQ ID NO: 5;
a UL128 protein comprising a sequence having 90% or more sequence identity with SEQ ID NO: 6;
a UL130 protein comprising a sequence having 90% or more sequence identity with SEQ ID NO: 7; and
a UL131 protein comprising a sequence having 90% or more sequence identity with SEQ ID NO: 8.
2. The fusion protein complex according to claim 1, wherein the three gB proteins are fused to the gL protein, the UL128 protein, and the UL130 protein of the pentamer, separately.

3. The fusion protein complex according to claim 1, wherein at least one fusion of fusions by genetic engineering is a fusion in which one of the CMV proteins of the pentamer is bound to an N-terminus side of the gB protein, optionally wherein the fusion protein has a linker and/or a tag between the gB protein and the CMV protein, optionally wherein the linker is a linker consisting of an amino acid sequence having one to three repeats of an amino acid sequence unit set forth in SEQ ID NO: 22.
4. The fusion protein complex according to claim 1, wherein at least two fusions of fusions by genetic engineering are fusions in which the CMV proteins of the pentamer are bound to an N-terminus side of the gB proteins, or, wherein all three fusions by genetic engineering are fusions in which the CMV proteins of the pentamer are bound to an N-terminus side of the gB proteins.
5. The fusion protein complex according to claim 1, wherein the gB protein is an ectodomain of the CMV gB protein.
6. The fusion protein complex according to claim 5, wherein the gB protein is an ectodomain of a gB protein of human cytomegalovirus (HCMV) consisting of an amino acid sequence set forth in SEQ ID NO: 15 or the amino acid sequence in which one or more amino acid residues are deleted, substituted, or added, or, wherein the gB protein is an ectodomain of a gB protein having 90% or more sequence identity with an ectodomain of the gB protein consisting of the amino acid sequence set forth in SEQ ID NO: 15.

7. The fusion protein complex according to claim 1, wherein the gB protein is a gB protein variant in which Domain IV is deleted.

8. The fusion protein complex according to claim 7, wherein the gB protein is an ectodomain of a gB protein of human cytomegalovirus (HCMV) consisting of an amino acid sequence set forth in SEQ ID NO: 16 or the amino acid sequence in which one or more amino acid residues are deleted, substituted, or added, or wherein the gB protein is an ectodomain of a gB protein having 90% or more sequence identity with an ectodomain of a gB protein consisting of the amino acid sequence set forth in SEQ ID NO: 16.

9. The fusion protein complex according to claim 1, wherein the gB protein is a gB protein variant having introduced therein a modification for reducing formation of an aggregate as compared with a wild type gB protein.

10. The fusion protein complex according to claim 9, wherein the gB protein is an ectodomain of a gB protein of human cytomegalovirus (HCMV) consisting of an amino acid sequence set forth in SEQ ID NO: 3 or the amino acid sequence in which one or more amino acid residues are deleted, substituted, or added, or wherein the gB protein is an ectodomain of a gB protein having 90% or more sequence identity with an ectodomain of a gB protein consisting of the amino acid sequence set forth in SEQ ID NO: 3.

11. The fusion protein complex according to claim 1, wherein the gB protein is a gB protein variant having introduced therein a modification for reducing immunogenicity of a head region as compared with a wild type gB protein.

12. The fusion protein complex according to claim 11, wherein the gB protein is an ectodomain of a gB protein of human cytomegalovirus (HCMV) consisting of an amino acid sequence set forth in SEQ ID NO: 31 or the amino acid sequence in which one or more amino acid residues are deleted, substituted, or added, or wherein the gB protein is an ectodomain of a gB protein having 90% or more sequence identity with an ectodomain of the gB protein consisting of the amino acid sequence set forth in SEQ ID NO: 31.

13. The fusion protein complex according to claim 1, wherein
the gH protein comprises human gH protein or an ectodomain of the human gH protein, and
the gL protein, the UL128 protein, the UL130 protein, and the UL131 protein comprise human gL protein, human UL128 protein, human UL130 protein, and human UL131 protein, respectively.

14. The fusion protein complex according to claim 13, wherein
the pentamer is a pentamer protein of human cytomegalovirus (HCMV) comprising:

gH protein consisting of an amino acid sequence set forth in SEQ ID NO: 4 or the amino acid sequence;
gL protein consisting of an amino acid sequence set forth in SEQ ID NO: 5 or the amino acid sequence;
UL128 protein consisting of an amino acid sequence set forth in SEQ ID NO: 6 or the amino acid sequence;
UL130 protein consisting of an amino acid sequence set forth in SEQ ID NO: 7 or the amino acid sequence; and
UL131 protein consisting of an amino acid sequence set forth in SEQ ID NO: 8 or the amino acid sequence.

15. The fusion protein complex according to claim 13, wherein
the pentamer consists of:
gH protein having 90% or more sequence identity with gH consisting of the amino acid sequence set forth in SEQ ID NO: 4;
gL protein having 90% or more sequence identity with gL consisting of the amino acid sequence set forth in SEQ ID NO: 5;
UL128 protein having 90% or more sequence identity with UL128 consisting of the amino acid sequence set forth in SEQ ID NO: 6;
UL130 protein having 90% or more sequence identity with UL130 consisting of the amino acid sequence set forth in SEQ ID NO: 7; and
UL131 protein having 90% or more sequence identity with UL131 consisting of the amino acid sequence set forth in SEQ ID NO: 8.

16. A nucleic acid fragment encoding the fusion protein complex according to claim 1.

17. A recombinant expression vector comprising the nucleic acid fragment according to claim 16.

18. A transformant having introduced therein the nucleic acid fragment according to claim 16.

19. A vaccine for treating infection with CMV, comprising the fusion protein according to claim 1, optionally wherein the infection with CMV is congenital infection with CMV.

20. The fusion protein complex according to claim 1, wherein the three gB proteins are fused to the UL128 protein, the UL130 protein, and the UL131 protein of the pentamer, separately.

21. The fusion protein complex according to claim 1, wherein one of the three gB protein is fused to any one selected from the group consisting of gL, UL128, UL130, and UL131.

22. The fusion protein complex according to claim 1, wherein the three gB proteins are fused to the gL protein, the UL128 protein, and the UL131 protein of the pentamer, separately.

23. The fusion protein complex according to claim 1, wherein the three gB proteins are fused to the gL protein, the UL130 protein, and the UL131 protein of the pentamer, separately.

* * * * *

SEQUENCE LISTING

<160> NUMBER OF SEQ ID NOS: 32

<210> SEQ ID NO 1
<211> LENGTH: 906
<212> TYPE: PRT
<213> ORGANISM: Human cytomegalovirus
<220> FEATURE:
<221> NAME/KEY: MISC_FEATURE
<222> LOCATION: (1)..(439)
<223> OTHER INFORMATION: HCMV AD169 gB

<400> SEQUENCE: 1

Met Glu Ser Arg Ile Trp Cys Leu Val Val Cys Val Asn Leu Cys Ile
1               5                   10                  15

-continued

```
Val Cys Leu Gly Ala Ala Val Ser Ser Ser Ser Thr Ser His Ala Thr
             20              25              30

Ser Ser Thr His Asn Gly Ser His Thr Ser Arg Thr Thr Ser Ala Gln
         35              40              45

Thr Arg Ser Val Tyr Ser Gln His Val Thr Ser Ser Glu Ala Val Ser
     50              55              60

His Arg Ala Asn Glu Thr Ile Tyr Asn Thr Thr Leu Lys Tyr Gly Asp
65              70              75              80

Val Val Gly Val Asn Thr Thr Lys Tyr Pro Tyr Arg Val Cys Ser Met
             85              90              95

Ala Gln Gly Thr Asp Leu Ile Arg Phe Glu Arg Asn Ile Ile Cys Thr
         100             105             110

Ser Met Lys Pro Ile Asn Glu Asp Leu Asp Glu Gly Ile Met Val Val
         115             120             125

Tyr Lys Arg Asn Ile Val Ala His Thr Phe Lys Val Arg Val Tyr Gln
     130             135             140

Lys Val Leu Thr Phe Arg Arg Ser Tyr Ala Tyr Ile Tyr Thr Thr Tyr
145             150             155             160

Leu Leu Gly Ser Asn Thr Glu Tyr Val Ala Pro Pro Met Trp Glu Ile
             165             170             175

His His Ile Asn Lys Phe Ala Gln Cys Tyr Ser Ser Tyr Ser Arg Val
             180             185             190

Ile Gly Gly Thr Val Phe Val Ala Tyr His Arg Asp Ser Tyr Glu Asn
         195             200             205

Lys Thr Met Gln Leu Ile Pro Asp Asp Tyr Ser Asn Thr His Ser Thr
     210             215             220

Arg Tyr Val Thr Val Lys Asp Gln Trp His Ser Arg Gly Ser Thr Trp
225             230             235             240

Leu Tyr Arg Glu Thr Cys Asn Leu Asn Cys Met Leu Thr Ile Thr Thr
             245             250             255

Ala Arg Ser Lys Tyr Pro Tyr His Phe Phe Ala Thr Ser Thr Gly Asp
         260             265             270

Val Val Tyr Ile Ser Pro Phe Tyr Asn Gly Thr Asn Arg Asn Ala Ser
         275             280             285

Tyr Phe Gly Glu Asn Ala Asp Lys Phe Phe Ile Phe Pro Asn Tyr Thr
     290             295             300

Ile Val Ser Asp Phe Gly Arg Pro Asn Ala Ala Pro Glu Thr His Arg
305             310             315             320

Leu Val Ala Phe Leu Glu Arg Ala Asp Ser Val Ile Ser Trp Asp Ile
             325             330             335

Gln Asp Glu Lys Asn Val Thr Cys Gln Leu Thr Phe Trp Glu Ala Ser
         340             345             350

Glu Arg Thr Ile Arg Ser Glu Ala Glu Asp Ser Tyr His Phe Ser Ser
         355             360             365

Ala Lys Met Thr Ala Thr Phe Leu Ser Lys Lys Gln Glu Val Asn Met
     370             375             380

Ser Asp Ser Ala Leu Asp Cys Val Arg Asp Glu Ala Ile Asn Lys Leu
385             390             395             400

Gln Gln Ile Phe Asn Thr Ser Tyr Asn Gln Thr Tyr Glu Lys Tyr Gly
             405             410             415

Asn Val Ser Val Phe Glu Thr Ser Gly Gly Leu Val Val Phe Trp Gln
             420             425             430

Gly Ile Lys Gln Lys Ser Leu Val Glu Leu Glu Arg Leu Ala Asn Arg
```

```
              435                    440                    445
Ser Ser Leu Asn Ile Thr His Arg Thr Arg Arg Ser Thr Ser Asp Asn
    450                    455                    460
Asn Thr Thr His Leu Ser Ser Met Glu Ser Val His Asn Leu Val Tyr
465                    470                    475                    480
Ala Gln Leu Gln Phe Thr Tyr Asp Thr Leu Arg Gly Tyr Ile Asn Arg
                485                    490                    495
Ala Leu Ala Gln Ile Ala Glu Ala Trp Cys Val Asp Gln Arg Arg Thr
                500                    505                    510
Leu Glu Val Phe Lys Glu Leu Ser Lys Ile Asn Pro Ser Ala Ile Leu
                515                    520                    525
Ser Ala Ile Tyr Asn Lys Pro Ile Ala Ala Arg Phe Met Gly Asp Val
    530                    535                    540
Leu Gly Leu Ala Ser Cys Val Thr Ile Asn Gln Thr Ser Val Lys Val
545                    550                    555                    560
Leu Arg Asp Met Asn Val Lys Glu Ser Pro Gly Arg Cys Tyr Ser Arg
                565                    570                    575
Pro Val Val Ile Phe Asn Phe Ala Asn Ser Ser Tyr Val Gln Tyr Gly
                580                    585                    590
Gln Leu Gly Glu Asp Asn Glu Ile Leu Leu Gly Asn His Arg Thr Glu
                595                    600                    605
Glu Cys Gln Leu Pro Ser Leu Lys Ile Phe Ile Ala Gly Asn Ser Ala
    610                    615                    620
Tyr Glu Tyr Val Asp Tyr Leu Phe Lys Arg Met Ile Asp Leu Ser Ser
625                    630                    635                    640
Ile Ser Thr Val Asp Ser Met Ile Ala Leu Asp Ile Asp Pro Leu Glu
                645                    650                    655
Asn Thr Asp Phe Arg Val Leu Glu Leu Tyr Ser Gln Lys Glu Leu Arg
                660                    665                    670
Ser Ser Asn Val Phe Asp Leu Glu Glu Ile Met Arg Glu Phe Asn Ser
                675                    680                    685
Tyr Lys Gln Arg Val Lys Tyr Val Glu Asp Lys Val Val Asp Pro Leu
    690                    695                    700
Pro Pro Tyr Leu Lys Gly Leu Asp Asp Leu Met Ser Gly Leu Gly Ala
705                    710                    715                    720
Ala Gly Lys Ala Val Gly Val Ala Ile Gly Ala Val Gly Gly Ala Val
                725                    730                    735
Ala Ser Val Val Glu Gly Val Ala Thr Phe Leu Lys Asn Pro Phe Gly
                740                    745                    750
Ala Phe Thr Ile Ile Leu Val Ala Ile Ala Val Val Ile Ile Thr Tyr
                755                    760                    765
Leu Ile Tyr Thr Arg Gln Arg Arg Leu Cys Thr Gln Pro Leu Gln Asn
    770                    775                    780
Leu Phe Pro Tyr Leu Val Ser Ala Asp Gly Thr Thr Val Thr Ser Gly
785                    790                    795                    800
Ser Thr Lys Asp Thr Ser Leu Gln Ala Pro Pro Ser Tyr Glu Glu Ser
                805                    810                    815
Val Tyr Asn Ser Gly Arg Lys Gly Pro Gly Pro Pro Ser Ser Asp Ala
                820                    825                    830
Ser Thr Ala Ala Pro Pro Tyr Thr Asn Glu Gln Ala Tyr Gln Met Leu
                835                    840                    845
Leu Ala Leu Ala Arg Leu Asp Ala Glu Gln Arg Ala Gln Gln Asn Gly
    850                    855                    860
```

```
Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905

<210> SEQ ID NO 2
<211> LENGTH: 900
<212> TYPE: PRT
<213> ORGANISM: Guinea pig cytomegalovirus
<220> FEATURE:
<221> NAME/KEY: MISC_FEATURE
<222> LOCATION: (1)..(900)
<223> OTHER INFORMATION: GPCMV 22122 gB

<400> SEQUENCE: 2

Met Arg Pro Val Arg Gly Ile Ala Arg Ser Arg Ile Leu Ser Cys Ser
1               5                   10                  15

Trp Arg Gly Thr Trp Thr Ser Ala Leu Thr Ile Leu Tyr Leu Gly Val
                20                  25                  30

Tyr Cys Glu Ser Thr Thr Val Thr Pro Thr Thr Val Glu Asp Thr Thr
            35                  40                  45

Val Ser Asn Gly Asn His Ser Asp Ala Ser Arg Asn Asn Thr Val Ile
        50                  55                  60

Arg Asn Leu Thr Ala Ser Val Asp Phe Ser Gln Arg Lys Leu Tyr Pro
65                  70                  75                  80

Tyr Arg Ile Cys Ser Met Ser Met Gly Thr Asp Leu Val Arg Phe Ala
                85                  90                  95

Arg Thr Ile Gln Cys Val Pro Phe Asn Pro Arg Val Asn Ser Glu Glu
                100                 105                 110

Gly Ile Met Leu Ile Tyr Lys Arg Asn Ile Leu Pro Tyr Val Phe Thr
            115                 120                 125

Ala Tyr Thr Tyr Gln Lys Glu Leu Leu Phe Gln Arg Ser Tyr Lys Tyr
        130                 135                 140

Val Thr Tyr Asp Tyr Leu Leu Gly Tyr Ser Arg Glu Phe Val Ala Leu
145                 150                 155                 160

Pro Met Trp Glu Ile Phe Leu Val Asn Ser Arg Gly Gln Cys Tyr Thr
                165                 170                 175

Ser His Gln Arg Val Ile Gly Ala Asp Arg Tyr Ile Ala Tyr His Asn
                180                 185                 190

Asp Asn Glu Val Asn Glu Thr Met Trp Leu Met Arg Asp Asp Met Gly
            195                 200                 205

Asn Asp Asp Thr Tyr Arg Tyr Ile Thr Val Lys Glu His Ala Arg Thr
        210                 215                 220

Pro Gly Ser Val Trp Leu Tyr Lys Glu Thr Cys Ser Met Asn Cys Ile
225                 230                 235                 240

Val Thr Lys Thr Lys Gly Lys Ser Lys Phe Pro Tyr Asp Met Phe Val
                245                 250                 255

Leu Pro Ser Gly Val Ile Val Asn Ile Ser Pro Phe Tyr Asn Gly Ser
            260                 265                 270

Asn Gly Lys Thr Phe Arg Glu Gln Arg Glu Lys Phe His Ile Trp Ser
        275                 280                 285

Asn Tyr Ser Ile Leu Lys Asp Phe Gly Ser Arg Ala Leu Glu Ala Arg
        290                 295                 300
```

```
Ile Val Pro Lys Met Ala Phe Tyr Glu Arg Glu Asp Val Val Ile Gly
305             310             315             320

Trp Glu Val Asn Asp Gln Ser Asn Val Thr Cys Glu Met Ile Leu Trp
                325             330             335

Glu Thr Val Asp Arg Ala Ile Arg Thr Glu Tyr Glu Asn Ala Phe His
            340             345             350

Tyr Val Ala Arg Thr Leu Thr Ser Thr Phe Val Glu Asn Lys Tyr Ser
        355             360             365

Pro Asp Asn Asn Leu Thr Glu Asp Asp Ile Lys Cys Phe Lys Asn Asp
    370             375             380

Ala Gln Lys Lys Ile Glu Glu Val Phe Leu Arg Asp Tyr Asn Glu Thr
385             390             395             400

Tyr Asp Met Asp Gly Asn Ala Thr Tyr His Val Thr Thr Gly Gly Leu
            405             410             415

Val Ile Val Trp Gln Gly Leu Lys Gln Lys Ser Leu Lys Ala Leu Glu
            420             425             430

Ile Ala Ala Asn Glu Ser Ala Val Ser Ala Thr Gly Ser Asn Ser Arg
        435             440             445

Arg Lys Arg Ser Leu Pro Asp Glu Ser Thr Gly Asp Ile Ser Tyr Ala
    450             455             460

Gln Leu Gln Phe Ala Tyr Asp Thr Leu Arg Thr Tyr Ile Asn Gln Ala
465             470             475             480

Leu Gly His Ile Ala Glu Ala Trp Cys Leu Asp Gln Lys Arg Thr Ala
            485             490             495

Glu Val Leu His Glu Leu Ser Lys Ile Asn Pro Ser Asn Ile Leu Ser
            500             505             510

Ala Ile Phe Gly Val Pro Val Ala Ala Arg Val Val Gly Asp Val Ile
        515             520             525

Ser Leu Ala Lys Cys Ile Glu Val Asn Gln Ser Thr Val Leu Ile Lys
    530             535             540

Gly Asp Met Arg Lys Phe Ser Asp Asp Gly Lys Leu Glu Gly Cys Tyr
545             550             555             560

Ser Arg Pro Val Val Trp Phe Ser Met Lys Asn Ser Thr Glu Val Arg
            565             570             575

Leu Gly Gln Leu Gly Glu Asp Asn Glu Ile Leu Leu Gly Thr His Arg
            580             585             590

Met Glu Thr Cys Gln Thr Gln Asp Tyr Arg Ile Phe Val Ala Gly Asp
        595             600             605

Ile Gly Tyr Glu Phe Gln Gln Tyr Val Phe Thr Lys Lys Ile Asn Leu
    610             615             620

Ser Glu Ile Asp Ile Ile Asp Thr Met Ile Ala Leu Lys Thr Glu Pro
625             630             635             640

Leu Glu Asn Ile Asp Phe Lys Val Leu Glu Leu Tyr Ser Arg Asp Glu
            645             650             655

Leu Ala Gln Ala Asn Val Phe Asp Leu Glu Ser Ile Met Arg Glu Tyr
        660             665             670

Asn Tyr Gln Lys Lys Arg Leu Asp Phe Val Val Glu Arg Val Ile Asn
        675             680             685

Pro Ile Pro Pro Ala Leu Lys Gly Leu Asp Glu Met Met Asn Gly Met
    690             695             700

Gly Ala Ile Gly Lys Gly Ile Gly Glu Ala Val Gly Ala Val Gly Gly
705             710             715             720

Ala Ile Gly Ser Phe Ile Gly Ala Leu Val Thr Phe Val Thr Asn Pro
```

-continued

```
                    725              730              735
Phe Gly Ala Phe Val Val Phe Leu Phe Cys Val Gly Cys Ile Thr Leu
            740              745              750

Val Ile Thr Val Tyr Arg Arg Gln Arg Arg Ala Met Gln Arg Pro Phe
            755              760              765

Asp Tyr Phe Phe Pro Tyr Ala Ser Gln Thr Ile Thr Ser Ser Val Ala
    770              775              780

Asp Ser Ser Ile Ala Val Ala Tyr Pro Gly Pro Glu Gly Thr Ser Gly
785              790              795              800

Asp Ala Pro Pro Pro Tyr Pro Gly Glu Ala Pro Tyr Gly Tyr Lys Asp
            805              810              815

Leu Ser Val Asp Ala Asp Thr Arg Val Ser Ser Ser Ala Gly Ala
            820              825              830

Gly Ala Asp Phe Asn Glu Glu Asp Ala Val Arg Met Leu Arg Ala Ile
            835              840              845

Lys Arg Leu Asp Asp Lys Lys Arg Gln Glu Ile Glu Lys Ser Ser Lys
    850              855              860

Asp Ser Ala Ser Asn Lys Asn Ser Glu Thr Arg Arg Arg Pro Gly Ile
865              870              875              880

Met Asp Arg Leu Arg Arg Arg Gly Gly Tyr Gln Lys Leu Asn Thr Glu
            885              890              895

Asp Asp Val His
            900
```

```
<210> SEQ ID NO 3
<211> LENGTH: 682
<212> TYPE: PRT
<213> ORGANISM: Human cytomegalovirus
<220> FEATURE:
<221> NAME/KEY: MISC_FEATURE
<222> LOCATION: (1)..(682)
<223> OTHER INFORMATION: gB1-682-fm3Mv9

<400> SEQUENCE: 3

Ser Ser Ser Thr Ser His Ala Thr Ser Ser Thr His Asn Gly Ser His
1               5               10              15

Thr Ser Arg Thr Thr Ser Ala Gln Thr Arg Ser Val Tyr Ser Gln His
            20              25              30

Val Thr Ser Ser Glu Ala Val Ser His Arg Ala Asn Glu Thr Ile Tyr
            35              40              45

Asn Thr Thr Leu Lys Tyr Gly Asp Val Val Gly Val Asn Thr Thr Lys
    50              55              60

Tyr Pro Tyr Arg Val Cys Ser Met Ala Gln Gly Thr Asp Leu Ile Arg
65              70              75              80

Phe Glu Arg Asn Ile Ile Cys Thr Ser Met Lys Pro Ile Asn Glu Asp
            85              90              95

Leu Asp Glu Gly Ile Met Val Val Tyr Lys Arg Asn Ile Val Ala His
            100             105             110

Thr Phe Lys Val Arg Val Tyr Gln Lys Val Leu Thr Phe Arg Arg Ser
            115             120             125

Tyr Ala Tyr His Arg Thr Thr Tyr Leu Leu Gly Ser Asn Thr Glu Tyr
            130             135             140

Val Ala Pro Pro Met Trp Glu Ile His His Ile Asn Lys Phe Ala Gln
145             150             155             160

Cys Tyr Ser Ser Tyr Ser Arg Val Ile Gly Gly Thr Val Phe Val Ala
            165             170             175
```

-continued

```
Tyr His Arg Asp Ser Tyr Glu Asn Lys Thr Met Gln Leu Ile Pro Asp
        180                 185                 190

Asp Tyr Ser Asn Thr His Ser Thr Arg Tyr Val Thr Val Lys Asp Gln
        195                 200                 205

Trp His Ser Arg Gly Ser Glu Ala Leu Tyr Arg Glu Thr Cys Asn Leu
        210                 215                 220

Asn Cys Met Leu Thr Ile Thr Thr Ala Arg Ser Lys Tyr Pro Tyr His
225                 230                 235                 240

Phe Phe Ala Thr Ser Thr Gly Asp Val Val Tyr Ile Ser Pro Phe Tyr
                245                 250                 255

Asn Gly Thr Asn Arg Asn Ala Ser Tyr Phe Gly Glu Asn Ala Asp Lys
                260                 265                 270

Phe Phe Ile Phe Pro Asn Tyr Thr Ile Val Ser Asp Phe Gly Arg Pro
                275                 280                 285

Asn Ala Ala Pro Glu Thr His Arg Leu Val Ala Phe Leu Glu Arg Ala
        290                 295                 300

Asp Ser Val Ile Ser Trp Asp Ile Gln Asp Glu Lys Asn Val Thr Cys
305                 310                 315                 320

Gln Leu Thr Phe Trp Glu Ala Ser Glu Arg Thr Ile Arg Ser Glu Ala
                325                 330                 335

Glu Asp Ser Tyr His Phe Ser Ser Ala Lys Met Thr Ala Thr Phe Leu
                340                 345                 350

Ser Lys Lys Gln Glu Val Asn Met Ser Asp Ser Ala Leu Asp Cys Val
                355                 360                 365

Arg Asp Glu Ala Ile Asn Lys Leu Gln Gln Ile Phe Asn Thr Ser Tyr
        370                 375                 380

Asn Gln Thr Tyr Glu Lys Tyr Gly Asn Val Ser Val Phe Glu Thr Ser
385                 390                 395                 400

Gly Gly Leu Val Val Phe Trp Gln Gly Ile Lys Gln Lys Ser Leu Val
                405                 410                 415

Glu Leu Glu Arg Leu Ala Asn Arg Ser Ser Leu Asn Ile Thr His Thr
                420                 425                 430

Thr Gln Arg Ser Thr Ser Asp Asn Asn Thr Thr His Leu Ser Ser Met
        435                 440                 445

Glu Ser Val His Asn Leu Val Tyr Ala Gln Leu Gln Phe Thr Tyr Asp
        450                 455                 460

Thr Leu Arg Gly Tyr Ile Asn Arg Ala Leu Ala Gln Ile Ala Glu Ala
465                 470                 475                 480

Trp Cys Val Asp Gln Arg Arg Thr Leu Glu Val Phe Lys Glu Leu Ser
                485                 490                 495

Lys Ile Asn Pro Ser Ala Ile Leu Ser Ala Ile Tyr Asn Lys Pro Ile
                500                 505                 510

Ala Ala Arg Phe Met Gly Asp Val Leu Gly Leu Ala Ser Cys Val Thr
                515                 520                 525

Ile Asn Gln Thr Ser Val Lys Val Leu Arg Asp Met Asn Val Lys Glu
        530                 535                 540

Ser Pro Gly Arg Cys Tyr Ser Arg Pro Val Val Ile Phe Asn Phe Ala
545                 550                 555                 560

Asn Ser Ser Tyr Val Gln Tyr Gly Gln Leu Gly Glu Asp Asn Glu Ile
                565                 570                 575

Leu Leu Gly Asn His Arg Thr Glu Glu Cys Gln Leu Pro Ser Leu Lys
                580                 585                 590
```

```
Ile Phe Ile Ala Gly Asn Ser Ala Tyr Glu Tyr Val Asp Tyr Leu Phe
        595                 600                 605

Lys Arg Met Ile Asp Leu Ser Ser Ile Ser Thr Val Asp Ser Met Ile
        610                 615                 620

Ala Leu Asp Ile Asp Pro Leu Glu Asn Thr Asp Phe Arg Val Leu Glu
625                 630                 635                 640

Leu Tyr Ser Gln Lys Glu Leu Arg Ser Ser Asn Val Phe Asp Leu Glu
                645                 650                 655

Glu Ile Met Arg Glu Phe Asn Ser Tyr Lys Gln Arg Val Lys Tyr Val
                660                 665                 670

Glu Asp Lys Val Val Asp Pro Leu Pro Pro
        675                 680

<210> SEQ ID NO 4
<211> LENGTH: 715
<212> TYPE: PRT
<213> ORGANISM: Human cytomegalovirus
<220> FEATURE:
<221> NAME/KEY: MISC_FEATURE
<222> LOCATION: (1)..(715)
<223> OTHER INFORMATION: gH ectodomain

<400> SEQUENCE: 4

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
                20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
                100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
        130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
                180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
        210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
```

```
                260                 265                 270
Glu Lys His Glu Leu Leu Val Leu Val Lys Lys Asp Gln Leu Asn Arg
            275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
            355                 360                 365

Arg Gln Ala Ala Leu Leu Gln Ile Gln Glu Phe Met Ile Thr Cys Leu
        370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685
```

-continued

```
Ser Pro Arg Thr His Tyr Leu Met Leu Leu Lys Asn Gly Thr Val Leu
    690               695           700

Glu Val Thr Asp Val Val Val Asp Ala Thr Asp
705           710           715
```

<210> SEQ ID NO 5
<211> LENGTH: 278
<212> TYPE: PRT
<213> ORGANISM: Human cytomegalovirus
<220> FEATURE:
<221> NAME/KEY: MISC_FEATURE
<222> LOCATION: (1)..(278)
<223> OTHER INFORMATION: gL

<400> SEQUENCE: 5

```
Met Cys Arg Arg Pro Asp Cys Gly Phe Ser Phe Ser Pro Gly Pro Val
1               5               10              15

Ile Leu Leu Trp Cys Cys Leu Leu Leu Pro Ile Val Ser Ser Ala Ala
            20              25              30

Val Ser Val Ala Pro Thr Ala Ala Glu Lys Val Pro Ala Glu Cys Pro
        35              40              45

Glu Leu Thr Arg Arg Cys Leu Leu Gly Glu Val Phe Glu Gly Asp Lys
    50              55              60

Tyr Glu Ser Trp Leu Arg Pro Leu Val Asn Val Thr Gly Arg Asp Gly
65              70              75              80

Pro Leu Ser Gln Leu Ile Arg Tyr Arg Pro Val Thr Pro Glu Ala Ala
            85              90              95

Asn Ser Val Leu Leu Asp Glu Ala Phe Leu Asp Thr Leu Ala Leu Leu
            100             105             110

Tyr Asn Asn Pro Asp Gln Leu Arg Ala Leu Leu Thr Leu Leu Ser Ser
            115             120             125

Asp Thr Ala Pro Arg Trp Met Thr Val Met Arg Gly Tyr Ser Glu Cys
    130             135             140

Gly Asp Gly Ser Pro Ala Val Tyr Thr Cys Val Asp Asp Leu Cys Arg
145             150             155             160

Gly Tyr Asp Leu Thr Arg Leu Ser Tyr Gly Arg Ser Ile Phe Thr Glu
            165             170             175

His Val Leu Gly Phe Glu Leu Val Pro Pro Ser Leu Phe Asn Val Val
            180             185             190

Val Ala Ile Arg Asn Glu Ala Thr Arg Thr Asn Arg Ala Val Arg Leu
            195             200             205

Pro Val Ser Thr Ala Ala Ala Pro Glu Gly Ile Thr Leu Phe Tyr Gly
    210             215             220

Leu Tyr Asn Ala Val Lys Glu Phe Cys Leu Arg His Gln Leu Asp Pro
225             230             235             240

Pro Leu Leu Arg His Leu Asp Lys Tyr Tyr Ala Gly Leu Pro Pro Glu
            245             250             255

Leu Lys Gln Thr Arg Val Asn Leu Pro Ala His Ser Arg Tyr Gly Pro
            260             265             270

Gln Ala Val Asp Ala Arg
        275
```

<210> SEQ ID NO 6
<211> LENGTH: 171
<212> TYPE: PRT
<213> ORGANISM: Human cytomegalovirus
<220> FEATURE:

```
<221> NAME/KEY: MISC_FEATURE
<222> LOCATION: (1)..(171)
<223> OTHER INFORMATION: UL128

<400> SEQUENCE: 6

Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
                20                  25                  30

Phe Ile Asn Val Asn His Pro Pro Glu Arg Cys Tyr Asp Phe Lys Met
            35                  40                  45

Cys Asn Arg Phe Thr Val Ala Leu Arg Cys Pro Asp Gly Glu Val Cys
        50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
        130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170

<210> SEQ ID NO 7
<211> LENGTH: 214
<212> TYPE: PRT
<213> ORGANISM: Human cytomegalovirus
<220> FEATURE:
<221> NAME/KEY: MISC_FEATURE
<222> LOCATION: (1)..(214)
<223> OTHER INFORMATION: UL130

<400> SEQUENCE: 7

Met Leu Arg Leu Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
            35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Arg Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Arg Thr
        115                 120                 125

Ala Ser Lys Pro Ser Asp Gly Asn Val Gln Ile Ser Val Glu Asp Ala
        130                 135                 140

Lys Ile Phe Gly Ala His Met Val Pro Lys Gln Thr Lys Leu Leu Arg
```

-continued

```
          145                 150                 155                 160

Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
                180                 185                 190

Arg Leu Thr Phe Thr Glu Ala Asn Asn Gln Thr Tyr Thr Phe Cys Thr
            195                 200                 205

His Pro Asn Leu Ile Val
        210

<210> SEQ ID NO 8
<211> LENGTH: 129
<212> TYPE: PRT
<213> ORGANISM: Human cytomegalovirus
<220> FEATURE:
<221> NAME/KEY: MISC_FEATURE
<222> LOCATION: (1)..(129)
<223> OTHER INFORMATION: UL131

<400> SEQUENCE: 8

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
                20                  25                  30

Val Pro His Tyr Trp Asp Ala Cys Ser Arg Ala Leu Pro Asp Gln Thr
            35                  40                  45

Arg Tyr Lys Tyr Val Glu Gln Leu Val Asp Leu Thr Leu Asn Tyr His
        50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
                100                 105                 110

Leu Ala Pro His Ala Arg Ser Leu Glu Phe Ser Val Arg Leu Phe Ala
        115                 120                 125

Asn

<210> SEQ ID NO 9
<211> LENGTH: 742
<212> TYPE: PRT
<213> ORGANISM: Human cytomegalovirus
<220> FEATURE:
<221> NAME/KEY: MISC_FEATURE
<222> LOCATION: (1)..(742)
<223> OTHER INFORMATION: gH

<400> SEQUENCE: 9

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80
```

-continued

```
Phe Gln Ser Tyr Asn Gln Tyr Tyr Val Phe His Met Pro Arg Cys Leu
                85              90              95

Phe Ala Gly Pro Leu Ala Glu Gln Phe Leu Asn Gln Val Asp Leu Thr
            100             105             110

Glu Thr Leu Glu Arg Tyr Gln Gln Arg Leu Asn Thr Tyr Ala Leu Val
        115             120             125

Ser Lys Asp Leu Ala Ser Tyr Arg Ser Phe Ser Gln Gln Leu Lys Ala
    130             135             140

Gln Asp Ser Leu Gly Glu Gln Pro Thr Thr Val Pro Pro Pro Ile Asp
145             150             155             160

Leu Ser Ile Pro His Val Trp Met Pro Pro Gln Thr Thr Pro His Gly
            165             170             175

Trp Thr Glu Ser His Thr Thr Ser Gly Leu His Arg Pro His Phe Asn
            180             185             190

Gln Thr Cys Ile Leu Phe Asp Gly His Asp Leu Leu Phe Ser Thr Val
        195             200             205

Thr Pro Cys Leu His Gln Gly Phe Tyr Leu Ile Asp Glu Leu Arg Tyr
    210             215             220

Val Lys Ile Thr Leu Thr Glu Asp Phe Phe Val Val Thr Val Ser Ile
225             230             235             240

Asp Asp Asp Thr Pro Met Leu Leu Ile Phe Gly His Leu Pro Arg Val
            245             250             255

Leu Phe Lys Ala Pro Tyr Gln Arg Asp Asn Phe Ile Leu Arg Gln Thr
            260             265             270

Glu Lys His Glu Leu Leu Val Leu Val Lys Lys Asp Gln Leu Asn Arg
        275             280             285

His Ser Tyr Leu Lys Asp Pro Asp Phe Leu Asp Ala Ala Leu Asp Phe
    290             295             300

Asn Tyr Leu Asp Leu Ser Ala Leu Leu Arg Asn Ser Phe His Arg Tyr
305             310             315             320

Ala Val Asp Val Leu Lys Ser Gly Arg Cys Gln Met Leu Asp Arg Arg
            325             330             335

Thr Val Glu Met Ala Phe Ala Tyr Ala Leu Ala Leu Phe Ala Ala Ala
            340             345             350

Arg Gln Glu Glu Ala Gly Ala Gln Val Ser Val Pro Arg Ala Leu Asp
        355             360             365

Arg Gln Ala Ala Leu Leu Gln Ile Gln Glu Phe Met Ile Thr Cys Leu
    370             375             380

Ser Gln Thr Pro Pro Arg Thr Thr Leu Leu Leu Tyr Pro Thr Ala Val
385             390             395             400

Asp Leu Ala Lys Arg Ala Leu Trp Thr Pro Asn Gln Ile Thr Asp Ile
            405             410             415

Thr Ser Leu Val Arg Leu Val Tyr Ile Leu Ser Lys Gln Asn Gln Gln
            420             425             430

His Leu Ile Pro Gln Trp Ala Leu Arg Gln Ile Ala Asp Phe Ala Leu
        435             440             445

Lys Leu His Lys Thr His Leu Ala Ser Phe Leu Ser Ala Phe Ala Arg
    450             455             460

Gln Glu Leu Tyr Leu Met Gly Ser Leu Val His Ser Met Leu Val His
465             470             475             480

Thr Thr Glu Arg Arg Glu Ile Phe Ile Val Glu Thr Gly Leu Cys Ser
            485             490             495

Leu Ala Glu Leu Ser His Phe Thr Gln Leu Leu Ala His Pro His His
```

```
                  500                    505                    510
Glu Tyr Leu Ser Asp Leu Tyr Thr Pro Cys Ser Ser Ser Gly Arg Arg
              515                    520                    525

Asp His Ser Leu Glu Arg Leu Thr Arg Leu Phe Pro Asp Ala Thr Val
          530                    535                    540

Pro Ala Thr Val Pro Ala Ala Leu Ser Ile Leu Ser Thr Met Gln Pro
545                    550                    555                    560

Ser Thr Leu Glu Thr Phe Pro Asp Leu Phe Cys Leu Pro Leu Gly Glu
              565                    570                    575

Ser Phe Ser Ala Leu Thr Val Ser Glu His Val Ser Tyr Ile Val Thr
              580                    585                    590

Asn Gln Tyr Leu Ile Lys Gly Ile Ser Tyr Pro Val Ser Thr Thr Val
          595                    600                    605

Val Gly Gln Ser Leu Ile Ile Thr Gln Thr Asp Ser Gln Thr Lys Cys
          610                    615                    620

Glu Leu Thr Arg Asn Met His Thr Thr His Ser Ile Thr Val Ala Leu
625                    630                    635                    640

Asn Ile Ser Leu Glu Asn Cys Ala Phe Cys Gln Ser Ala Leu Leu Glu
              645                    650                    655

Tyr Asp Asp Thr Gln Gly Val Ile Asn Ile Met Tyr Met His Asp Ser
              660                    665                    670

Asp Asp Val Leu Phe Ala Leu Asp Pro Tyr Asn Glu Val Val Val Ser
              675                    680                    685

Ser Pro Arg Thr His Tyr Leu Met Leu Leu Lys Asn Gly Thr Val Leu
          690                    695                    700

Glu Val Thr Asp Val Val Val Asp Ala Thr Asp Ser Arg Leu Leu Met
705                    710                    715                    720

Met Ser Val Tyr Ala Leu Ser Ala Ile Ile Gly Ile Tyr Leu Leu Tyr
              725                    730                    735

Arg Met Leu Lys Thr Cys
              740
```

<210> SEQ ID NO 10
<211> LENGTH: 723
<212> TYPE: PRT
<213> ORGANISM: Guinea pig cytomegalovirus
<220> FEATURE:
<221> NAME/KEY: MISC_FEATURE
<222> LOCATION: (1)..(723)
<223> OTHER INFORMATION: GP75

<400> SEQUENCE: 10

```
Met Ser Pro Ala Thr Arg Phe Thr Val Ile Ser Cys Leu Val Val Ser
1               5                    10                    15

Leu Ile Thr Pro Ser Glu Thr Ser Ser Trp Phe Asp Pro Phe Ile Glu
              20                    25                    30

Trp Ala Arg Ser Ser Pro Asn Met Thr Cys Val Asn Asn Arg Thr Gly
          35                    40                    45

Thr Arg Ser Leu Ala Thr Glu Gly Leu Ile Ser Phe Asn Phe Tyr Glu
      50                    55                    60

Ala Ser Arg Thr Val Arg Thr Tyr Gln Val Pro Lys Cys Ile Phe Met
65                    70                    75                    80

Ser Ser Val Ser Lys Thr Ile Met Gln Gly Val Asp Leu Phe Glu Ser
              85                    90                    95

Leu Glu Ser Tyr Arg Arg Arg Tyr Tyr Ser Tyr Ile Ile Val Pro Val
              100                   105                   110
```

-continued

```
His Ala Ser Phe Gln Ile Phe Ile His Asp Leu Arg Thr Asp Leu Ser
        115                 120                 125

Ser Pro Thr Glu Glu Leu Thr Ser Pro Val Asp Lys Thr Leu Pro Asn
        130                 135                 140

Val Thr Ile Trp His Thr Pro Ser Gly Tyr Val Ile Arg Leu Leu Asp
145                 150                 155                 160

Val Val Thr Pro Arg Phe Glu Glu Cys Thr Leu Phe Pro Asn His Thr
                165                 170                 175

Val Ile Phe Asp Met Thr Val Pro Cys Ser Gln Glu Val Tyr Leu Arg
                180                 185                 190

Gln Thr Gly Lys His Gln Phe Ala Ile Val Leu Thr Phe Thr Pro Ser
        195                 200                 205

Phe Phe Val Leu Asn Ile Gln Thr Ala Gln His Gln His Val Thr Glu
        210                 215                 220

Asn Asp Glu Asp Val Ile Leu Ile Phe Gly Asp Val Arg Ser Ile Asp
225                 230                 235                 240

Val Lys Ala Pro Tyr Ser Lys Pro Val Leu Thr Leu Arg Gln Ser Tyr
                245                 250                 255

Arg Asp Asp Leu Leu Ile Val Ala Lys Thr Ser Ile Val Asn Ala Thr
                260                 265                 270

Tyr Pro Phe Ile Lys Thr Gln Asp Phe Leu Lys Gly Thr Leu Ser Gly
        275                 280                 285

Asn Tyr Leu Asp Phe Asn His Val Tyr Thr Glu Phe Asn Arg Leu Val
        290                 295                 300

Ile His Asn Leu Val Glu Gly Leu Cys Asp Ala Pro Pro Asp Asp Arg
305                 310                 315                 320

Thr Val Ser Met Val Phe Ser Tyr Ala Val Leu Ala Arg Thr Leu Tyr
                325                 330                 335

His Thr Ser Asn Val Thr Ala Arg Leu Glu Asp Val Ala Leu Arg Tyr
                340                 345                 350

Val Arg Leu Thr Leu Ala Arg Thr Phe Leu Gln Gln Cys Phe Asp Val
        355                 360                 365

Gly Pro Arg Tyr Met Arg Phe Pro Thr Ile Asp Gly Ala Leu Ser Val
        370                 375                 380

Leu Leu Lys Leu Ile Arg Asn Ser Arg Asp Val Asp Gly Gly Leu Lys
385                 390                 395                 400

Leu Ser Leu Thr Phe Ala Leu Ile Phe Gly Asn Asn Thr Asp Met Thr
                405                 410                 415

Lys Glu Arg Asp Leu Glu Asn Ala Leu Tyr Glu Met Lys Ser Ile His
                420                 425                 430

Arg Ala Gly Leu Val Ser Pro Leu Ser Pro Arg Gln Arg Ser Leu Leu
        435                 440                 445

Tyr Met Met Ala Tyr Val Thr His His Thr Thr Ala Phe Pro Asp Ile
        450                 455                 460

Arg Arg Glu Met Leu Ala Met Gln Thr Ser Leu Cys Ser Pro Gln Glu
465                 470                 475                 480

Leu Tyr Asn Trp Ala Pro His Val Ser Ser Ala Gly Leu Thr Met Gln
                485                 490                 495

Glu Met Phe Thr Pro Cys Ser Gly Ser Gly Arg Arg Asp Tyr Ser Glu
                500                 505                 510

Ala Arg Ile Ala Glu Ile Val Gln Leu Asn Pro Leu Thr Thr Lys Thr
        515                 520                 525
```

Pro Ala Asp Leu Tyr Arg Ile Leu Ala His Phe Asp Arg Ser Asn Leu
    530                 535                 540

Thr Asn Phe Pro Ala Leu Ser Cys Ile Ser His Leu Ser Gly Tyr Val
545                 550                 555                 560

Ala Val Thr Leu Arg Asp Val Thr Tyr Val Val Ser Ser Asn Val Met
                565                 570                 575

Leu Lys Gly Thr Ser Tyr Pro Val Thr Asn Leu Ala Val Asp Lys Thr
                580                 585                 590

Met Ile Val Thr Val Ser Pro Ala Gln His Pro Cys Glu Lys Thr Glu
            595                 600                 605

Val Ala His Ala Thr Arg Ser Ile Pro Ile Val Lys Asn Ile Thr Ile
    610                 615                 620

Gly Asn Asp Cys Glu Tyr Cys Lys Ser Ala Ile Met Glu Tyr Asp Glu
625                 630                 635                 640

Val Asn Gly Leu Ser Asn Ile Val Tyr Leu Ala Asp Thr Ala Asp Leu
                645                 650                 655

Val Leu Val Thr Asn Leu Asp Asn Arg Ile Leu Ala Ser Ser Pro Arg
                660                 665                 670

Thr Arg Tyr Ile Met Met Thr Ala Asn Gly Thr Leu Met Glu Ile Thr
                675                 680                 685

Ser Val Ile Ile Asp Ile Arg Gln Thr Ser Ile Phe Met Ile Met Leu
    690                 695                 700

Tyr Cys Ser Leu Gly Val Leu Leu Leu Tyr Gly Leu Tyr Arg Leu Leu
705                 710                 715                 720

His Met Ile

<210> SEQ ID NO 11
<211> LENGTH: 258
<212> TYPE: PRT
<213> ORGANISM: Guinea pig cytomegalovirus
<220> FEATURE:
<221> NAME/KEY: MISC_FEATURE
<222> LOCATION: (1)..(258)
<223> OTHER INFORMATION: GP115

<400> SEQUENCE: 11

Met Tyr Glu Cys Met Phe Phe Ser His Arg Leu Thr Ile Gly Phe Tyr
1               5                   10                  15

Ile Pro Leu Ile Val Leu Thr Thr Met Ser Ser Leu Ser Glu Ser Leu
                20                  25                  30

Gly Glu Arg Gln Lys Thr Ala Cys Thr Val Ala Ala Ile Ser Cys Ala
            35                  40                  45

Asn Ser Asp Thr Tyr Asn Arg Thr Thr Val Ser Asn His Thr Phe Phe
    50                  55                  60

Tyr Ile Ser Asp Arg Trp Lys Tyr Ser Glu Leu Ile Arg Tyr Glu Lys
65                  70                  75                  80

Pro Thr Gly Asp Leu Arg His Asp Lys Leu Ile His Val Asp Arg Glu
                85                  90                  95

Phe Leu Asp Ile Val Ser Leu Leu His Asn Asn Glu Asn Gln Leu Arg
                100                 105                 110

Thr Leu Leu Thr Ile Phe Arg Ser Asp Ser Ala Pro Pro Trp Val Lys
            115                 120                 125

Phe Met Arg Gly Tyr Ser Gln Cys Leu Asp His Pro Ile Ile Tyr Thr
    130                 135                 140

Cys Val Glu Glu Lys Cys Gln Gln Tyr Asn Leu Glu Glu Leu Pro Tyr
145                 150                 155                 160

-continued

```
Gly Lys Asp Ile Phe Leu Glu Asn Val Val Gly Phe Asp Leu Gly Ala
            165                 170                 175

Pro Pro His Asn Met Ser Val Leu Ile Ala Val Ser Asn Thr Lys Pro
            180                 185                 190

Lys Ile Thr Lys Val Leu Arg Ile Thr Ser Thr Ser Leu Thr Leu Phe
            195                 200                 205

Asp Ala Leu Tyr Asn Thr Val Leu Thr Phe Phe Arg Ser Ile Gly Ala
        210                 215                 220

Arg Asn Val Asp Val Val Arg Arg Leu Ile Leu Tyr Gln Ala Ser Leu
225                 230                 235                 240

Ser Gly Pro His Arg Asp Ala Pro Ile His Asn Tyr Leu Asn Arg Asp
            245                 250                 255

Leu Ser
```

```
<210> SEQ ID NO 12
<211> LENGTH: 179
<212> TYPE: PRT
<213> ORGANISM: Guinea pig cytomegalovirus
<220> FEATURE:
<221> NAME/KEY: MISC_FEATURE
<222> LOCATION: (1)..(179)
<223> OTHER INFORMATION: GP129
```

```
<400> SEQUENCE: 12
```

```
Met Arg Val Ile Val Leu Leu Val Met Phe Tyr Tyr Thr Arg Pro Gly
1               5                   10                  15

Ile Phe Asp Asp Pro Cys Cys Ile Tyr Ser Ser Lys Asp Arg Arg Val
            20                  25                  30

Gln His Ser Thr Thr Ser Asn Asp Thr Trp Arg Leu Val Arg Cys Gly
        35                  40                  45

Asn Thr Leu Met Val Ala Lys Arg Tyr Thr Asp Ser Phe Cys Glu Phe
    50                  55                  60

Ser Leu Glu Glu Asn Leu Phe Glu Ser Leu Ala Leu Asn Val Ser Arg
65                  70                  75                  80

Gln Glu Leu His Val Leu Ala Pro Glu Cys Lys Phe Gly Pro Val Glu
            85                  90                  95

Val Gly Ile Asn Lys Gln Val Arg Cys Ile Arg Tyr Pro Arg Met Pro
            100                 105                 110

Ser Val Gln Ser Lys Pro Glu Lys Pro Ser Ile Leu Gly Val Thr Tyr
            115                 120                 125

Arg Val Asp Tyr Thr Val Met Ile Pro Thr Pro His Phe Pro Arg Asp
        130                 135                 140

Phe Asn Gly Leu Leu Cys Thr Phe Leu Glu Lys Asn Asp Thr Phe Tyr
145                 150                 155                 160

Asn Thr Thr Val Asp Val Cys Gly Ser Glu Phe Tyr Ser Val Asp Gly
            165                 170                 175

Asn Gly Lys
```

```
<210> SEQ ID NO 13
<211> LENGTH: 192
<212> TYPE: PRT
<213> ORGANISM: Guinea pig cytomegalovirus
<220> FEATURE:
<221> NAME/KEY: MISC_FEATURE
<222> LOCATION: (1)..(192)
<223> OTHER INFORMATION: GP131
```

```
<400> SEQUENCE: 13
```

```
Met Met Lys Arg Tyr Leu Val Leu Leu Pro Trp Ile Met Phe Tyr Ala
1               5                   10                  15

Ser Phe Gly Arg Ala Gly Arg Cys Tyr Tyr Pro Ser Thr Pro Ile Pro
            20                  25                  30

Lys Ser Phe Val Lys His Val Asp Thr Thr Arg Ser Leu Pro Glu Cys
        35                  40                  45

Glu Asn Asp Thr Val Ala Val Leu Thr Leu Thr Asn Gly Ala Lys Leu
    50                  55                  60

Tyr Val Asn Met Leu Asn Thr Trp Ile Asp Gly Tyr Ile Thr Thr Leu
65                  70                  75                  80

Gln Tyr Ala Ile Pro Pro Thr Leu Ser Asp Ile Phe Ala Phe Ile Lys
                85                  90                  95

Arg Arg Ile Asp Tyr Gly Ser Thr Gly Thr Ala Ala Ser Thr Leu Pro
            100                 105                 110

Ser Leu Thr Ser Leu Arg Thr Tyr Phe Gly Asp Arg Asp Ser Ser Phe
            115                 120                 125

Leu Trp His Tyr Thr Ile Arg Met Lys Asp Gly Ala Lys Thr Leu Asp
        130                 135                 140

Cys Asp Val Tyr Val Thr Ser Arg Val His Phe Val Leu Asn Ser Tyr
145                 150                 155                 160

Glu Ala Val Gln Thr Val Leu Phe Glu Gly Gly Val Val Ile Ser Arg
                165                 170                 175

His Pro Ala Asp Ser Ile Ala Cys Leu Leu Ile Asn Trp Asn Trp Thr
            180                 185                 190
```

```
<210> SEQ ID NO 14
<211> LENGTH: 127
<212> TYPE: PRT
<213> ORGANISM: Guinea pig cytomegalovirus
<220> FEATURE:
<221> NAME/KEY: MISC_FEATURE
<222> LOCATION: (1)..(127)
<223> OTHER INFORMATION: GP133

<400> SEQUENCE: 14
```

```
Met Phe Trp Arg Leu Val Tyr Val Tyr Leu Val Ser Leu Leu Leu Ser
1               5                   10                  15

Ile Gly Ala Glu Asp Glu Gly Ile Asp Thr Trp Trp Leu Gly Gly Val
            20                  25                  30

Thr Asp Asn Thr Arg Val Lys Lys Glu Asn Gln Leu Ala His Tyr Ile
        35                  40                  45

Leu Lys Thr Ile Val Leu Thr His His Arg Arg Leu Arg Thr Gly Asp
    50                  55                  60

Glu Cys Thr Glu Gln Leu Ser Asn Asp Leu Asp Ile His Ser Val His
65                  70                  75                  80

Thr Leu Ala Asp Ser Ile Arg Arg Leu Arg Gly Arg Tyr Arg Lys Gly
                85                  90                  95

Leu Val Ser Ile Asp Gly Ile Arg Ile Ser Ile Gln Gln Ser Thr Arg
            100                 105                 110

Thr Gln Gln Lys Gly Leu Trp Ile Ser Ala Arg Ile Asp Arg Ala
        115                 120                 125
```

```
<210> SEQ ID NO 15
<211> LENGTH: 682
<212> TYPE: PRT
<213> ORGANISM: Human cytomegalovirus
<220> FEATURE:
```

<221> NAME/KEY: MISC_FEATURE
<222> LOCATION: (1)..(682)
<223> OTHER INFORMATION: gB1-682

<400> SEQUENCE: 15

```
Ser Ser Ser Thr Ser His Ala Thr Ser Ser Thr His Asn Gly Ser His
1               5                   10                  15

Thr Ser Arg Thr Thr Ser Ala Gln Thr Arg Ser Val Tyr Ser Gln His
            20                  25                  30

Val Thr Ser Ser Glu Ala Val Ser His Arg Ala Asn Glu Thr Ile Tyr
            35                  40                  45

Asn Thr Thr Leu Lys Tyr Gly Asp Val Val Gly Val Asn Thr Thr Lys
        50                  55                  60

Tyr Pro Tyr Arg Val Cys Ser Met Ala Gln Gly Thr Asp Leu Ile Arg
65                  70                  75                  80

Phe Glu Arg Asn Ile Ile Cys Thr Ser Met Lys Pro Ile Asn Glu Asp
                85                  90                  95

Leu Asp Glu Gly Ile Met Val Val Tyr Lys Arg Asn Ile Val Ala His
            100                 105                 110

Thr Phe Lys Val Arg Val Tyr Gln Lys Val Leu Thr Phe Arg Arg Ser
            115                 120                 125

Tyr Ala Tyr Ile Tyr Thr Thr Tyr Leu Leu Gly Ser Asn Thr Glu Tyr
        130                 135                 140

Val Ala Pro Pro Met Trp Glu Ile His His Ile Asn Lys Phe Ala Gln
145                 150                 155                 160

Cys Tyr Ser Ser Tyr Ser Arg Val Ile Gly Gly Thr Val Phe Val Ala
                165                 170                 175

Tyr His Arg Asp Ser Tyr Glu Asn Lys Thr Met Gln Leu Ile Pro Asp
            180                 185                 190

Asp Tyr Ser Asn Thr His Ser Thr Arg Tyr Val Thr Val Lys Asp Gln
            195                 200                 205

Trp His Ser Arg Gly Ser Thr Trp Leu Tyr Arg Glu Thr Cys Asn Leu
        210                 215                 220

Asn Cys Met Leu Thr Ile Thr Thr Ala Arg Ser Lys Tyr Pro Tyr His
225                 230                 235                 240

Phe Phe Ala Thr Ser Thr Gly Asp Val Val Tyr Ile Ser Pro Phe Tyr
                245                 250                 255

Asn Gly Thr Asn Arg Asn Ala Ser Tyr Phe Gly Glu Asn Ala Asp Lys
            260                 265                 270

Phe Phe Ile Phe Pro Asn Tyr Thr Ile Val Ser Asp Phe Gly Arg Pro
            275                 280                 285

Asn Ala Ala Pro Glu Thr His Arg Leu Val Ala Phe Leu Glu Arg Ala
        290                 295                 300

Asp Ser Val Ile Ser Trp Asp Ile Gln Asp Glu Lys Asn Val Thr Cys
305                 310                 315                 320

Gln Leu Thr Phe Trp Glu Ala Ser Glu Arg Thr Ile Arg Ser Glu Ala
                325                 330                 335

Glu Asp Ser Tyr His Phe Ser Ser Ala Lys Met Thr Ala Thr Phe Leu
            340                 345                 350

Ser Lys Lys Gln Glu Val Asn Met Ser Asp Ser Ala Leu Asp Cys Val
            355                 360                 365

Arg Asp Glu Ala Ile Asn Lys Leu Gln Gln Ile Phe Asn Thr Ser Tyr
        370                 375                 380

Asn Gln Thr Tyr Glu Lys Tyr Gly Asn Val Ser Val Phe Glu Thr Ser
```

-continued

```
385               390               395               400

Gly Gly Leu Val Val Phe Trp Gln Gly Ile Lys Gln Lys Ser Leu Val
                405               410               415

Glu Leu Glu Arg Leu Ala Asn Arg Ser Ser Leu Asn Ile Thr His Arg
                420               425               430

Thr Arg Arg Ser Thr Ser Asp Asn Asn Thr Thr His Leu Ser Ser Met
                435               440               445

Glu Ser Val His Asn Leu Val Tyr Ala Gln Leu Gln Phe Thr Tyr Asp
        450               455               460

Thr Leu Arg Gly Tyr Ile Asn Arg Ala Leu Ala Gln Ile Ala Glu Ala
465               470               475               480

Trp Cys Val Asp Gln Arg Arg Thr Leu Glu Val Phe Lys Glu Leu Ser
                485               490               495

Lys Ile Asn Pro Ser Ala Ile Leu Ser Ala Ile Tyr Asn Lys Pro Ile
                500               505               510

Ala Ala Arg Phe Met Gly Asp Val Leu Gly Leu Ala Ser Cys Val Thr
                515               520               525

Ile Asn Gln Thr Ser Val Lys Val Leu Arg Asp Met Asn Val Lys Glu
        530               535               540

Ser Pro Gly Arg Cys Tyr Ser Arg Pro Val Val Ile Phe Asn Phe Ala
545               550               555               560

Asn Ser Ser Tyr Val Gln Tyr Gly Gln Leu Gly Glu Asp Asn Glu Ile
                565               570               575

Leu Leu Gly Asn His Arg Thr Glu Glu Cys Gln Leu Pro Ser Leu Lys
                580               585               590

Ile Phe Ile Ala Gly Asn Ser Ala Tyr Glu Tyr Val Asp Tyr Leu Phe
                595               600               605

Lys Arg Met Ile Asp Leu Ser Ser Ile Ser Thr Val Asp Ser Met Ile
                610               615               620

Ala Leu Asp Ile Asp Pro Leu Glu Asn Thr Asp Phe Arg Val Leu Glu
625               630               635               640

Leu Tyr Ser Gln Lys Glu Leu Arg Ser Ser Asn Val Phe Asp Leu Glu
                645               650               655

Glu Ile Met Arg Glu Phe Asn Ser Tyr Lys Gln Arg Val Lys Tyr Val
                660               665               670

Glu Asp Lys Val Val Asp Pro Leu Pro Pro
        675               680
```

```
<210> SEQ ID NO 16
<211> LENGTH: 433
<212> TYPE: PRT
<213> ORGANISM: Human cytomegalovirus
<220> FEATURE:
<221> NAME/KEY: MISC_FEATURE
<222> LOCATION: (1)..(433)
<223> OTHER INFORMATION: gB delta d4

<400> SEQUENCE: 16

Leu Asp Glu Gly Ile Met Val Val Tyr Lys Arg Asn Ile Val Ala His
1               5               10               15

Thr Phe Lys Val Arg Val Tyr Gln Lys Val Leu Thr Phe Arg Arg Ser
                20               25               30

Tyr Ala Ala Ala Ala Thr Thr Tyr Leu Leu Gly Ser Asn Thr Glu Tyr
        35               40               45

Val Ala Pro Pro Met Trp Glu Ile His His Ile Asn Lys Phe Ala Gln
        50               55               60
```

-continued

```
Cys Tyr Ser Ser Tyr Ser Arg Val Ile Gly Gly Thr Val Phe Val Ala
65              70                  75                  80

Tyr His Arg Asp Ser Tyr Glu Asn Lys Thr Met Gln Leu Ile Pro Asp
                85                  90                  95

Asp Tyr Ser Asn Thr His Ser Thr Arg Tyr Val Thr Val Lys Asp Gln
            100                 105                 110

Trp His Ser Arg Gly Ser Thr Ala Leu Tyr Arg Glu Thr Cys Asn Leu
            115                 120                 125

Asn Cys Met Leu Thr Ile Thr Thr Ala Arg Ser Lys Tyr Pro Tyr His
    130                 135                 140

Phe Phe Ala Thr Ser Thr Gly Asp Val Val Tyr Ile Ser Pro Phe Tyr
145                 150                 155                 160

Asn Gly Thr Asn Arg Asn Ala Ser Tyr Phe Gly Glu Asn Ala Asp Lys
                165                 170                 175

Phe Phe Ile Phe Pro Asn Tyr Thr Ile Val Ser Asp Phe Gly Arg Pro
            180                 185                 190

Asn Ala Ala Pro Glu Thr His Arg Leu Val Ala Phe Leu Glu Arg Ala
            195                 200                 205

Asp Ser Val Ile Ser Trp Asp Ile Gln Asp Glu Lys Asn Val Thr Cys
    210                 215                 220

Gln Leu Thr Phe Trp Glu Ala Ser Glu Arg Thr Ile Arg Ser Glu Ala
225                 230                 235                 240

Glu Asp Ser Tyr His Phe Ser Ser Ala Lys Met Thr Ala Thr Phe Leu
                245                 250                 255

Ser Lys Lys Gln Glu Val Asn Met Ser Asp Ser Ala Leu Asp Cys Val
            260                 265                 270

Arg Asp Glu Ala Ile Asn Lys Leu Gln Gln Ile Phe Asn Thr Ser Tyr
            275                 280                 285

Asn Gln Thr Tyr Glu Lys Tyr Gly Asn Val Ser Val Phe Glu Thr Ser
    290                 295                 300

Gly Gly Leu Val Val Phe Trp Gln Gly Ile Lys Gln Lys Ser Leu Val
305                 310                 315                 320

Glu Leu Glu Arg Leu Ala Asn Arg Ser Ser Leu Asn Ile Thr His Thr
                325                 330                 335

Thr Gln Arg Ser Thr Ser Asp Asn Asn Thr Thr His Leu Ser Ser Met
            340                 345                 350

Glu Ser Val His Asn Leu Val Tyr Ala Gln Leu Gln Phe Thr Tyr Asp
            355                 360                 365

Thr Leu Arg Gly Gly Gly Gly Ser Gly Ser Gly Gly Gly Leu Glu Asn
    370                 375                 380

Thr Asp Phe Arg Val Leu Glu Leu Tyr Ser Gln Lys Glu Leu Arg Ser
385                 390                 395                 400

Ser Asn Val Phe Asp Leu Glu Glu Ile Met Arg Glu Phe Asn Ser Tyr
                405                 410                 415

Lys Gln Arg Val Lys Tyr Val Glu Asp Lys Val Val Asp Pro Leu Pro
            420                 425                 430

Pro
```

```
<210> SEQ ID NO 17
<211> LENGTH: 692
<212> TYPE: PRT
<213> ORGANISM: Guinea pig cytomegalovirus
<220> FEATURE:
<221> NAME/KEY: MISC_FEATURE
```

```
<222> LOCATION: (1)..(692)
<223> OTHER INFORMATION: GPCMV gB ectodomain

<400> SEQUENCE: 17

Met Arg Pro Val Arg Gly Ile Ala Arg Ser Arg Ile Leu Ser Cys Ser
1               5                   10                  15

Trp Arg Gly Thr Trp Thr Ser Ala Leu Thr Ile Leu Tyr Leu Gly Val
            20                  25                  30

Tyr Cys Glu Ser Thr Thr Val Thr Pro Thr Thr Val Glu Asp Thr Thr
        35                  40                  45

Val Ser Asn Gly Asn His Ser Asp Ala Ser Arg Asn Asn Thr Val Ile
    50                  55                  60

Arg Asn Leu Thr Ala Ser Val Asp Phe Ser Gln Arg Lys Leu Tyr Pro
65                  70                  75                  80

Tyr Arg Ile Cys Ser Met Ser Met Gly Thr Asp Leu Val Arg Phe Ala
                85                  90                  95

Arg Thr Ile Gln Cys Val Pro Phe Asn Pro Arg Val Asn Ser Glu Glu
            100                 105                 110

Gly Ile Met Leu Ile Tyr Lys Arg Asn Ile Leu Pro Tyr Val Phe Thr
        115                 120                 125

Ala Tyr Thr Tyr Gln Lys Glu Leu Leu Phe Gln Arg Ser Tyr Lys Gly
    130                 135                 140

His Arg Tyr Asp Tyr Leu Leu Gly Tyr Ser Arg Glu Phe Val Ala Leu
145                 150                 155                 160

Pro Met Trp Glu Ile Phe Leu Val Asn Ser Arg Gly Gln Cys Tyr Thr
                165                 170                 175

Ser His Gln Arg Val Ile Gly Ala Asp Arg Tyr Ile Ala Tyr His Asn
                180                 185                 190

Asp Asn Glu Val Asn Glu Thr Met Trp Leu Met Arg Asp Asp Met Gly
            195                 200                 205

Asn Asp Asp Thr Tyr Arg Tyr Ile Thr Val Lys Glu His Ala Arg Thr
        210                 215                 220

Pro Gly Ser Val Ala Phe His Lys Glu Thr Cys Ser Met Asn Cys Ile
225                 230                 235                 240

Val Thr Lys Thr Lys Gly Lys Ser Lys Phe Pro Tyr Asp Met Phe Val
                245                 250                 255

Leu Pro Ser Gly Val Ile Val Asn Ile Ser Pro Phe Tyr Asn Gly Ser
            260                 265                 270

Asn Gly Lys Thr Phe Arg Glu Gln Arg Glu Lys Phe His Ile Trp Ser
        275                 280                 285

Asn Tyr Ser Ile Leu Lys Asp Phe Gly Ser Arg Ala Leu Glu Ala Arg
    290                 295                 300

Ile Val Pro Lys Met Ala Phe Tyr Glu Arg Glu Asp Val Val Ile Gly
305                 310                 315                 320

Trp Glu Val Asn Asp Gln Ser Asn Val Thr Cys Glu Met Ile Leu Trp
                325                 330                 335

Glu Thr Val Asp Arg Ala Ile Arg Thr Glu Tyr Glu Asn Ala Phe His
            340                 345                 350

Tyr Val Ala Arg Thr Leu Thr Ser Thr Phe Val Glu Asn Lys Tyr Ser
        355                 360                 365

Pro Asp Asn Asn Leu Thr Glu Asp Asp Ile Lys Cys Phe Lys Asn Asp
    370                 375                 380

Ala Gln Lys Lys Ile Glu Glu Val Phe Leu Arg Asp Tyr Asn Glu Thr
385                 390                 395                 400
```

-continued

```
Tyr Asp Met Asp Gly Asn Ala Thr Tyr His Val Thr Thr Gly Gly Leu
            405                 410                 415

Val Ile Val Trp Gln Gly Leu Lys Gln Lys Ser Leu Lys Ala Leu Glu
            420                 425                 430

Ile Ala Ala Asn Glu Ser Ala Val Ser Ala Thr Gly Ser Asn Ser Arg
            435                 440                 445

Arg Lys Arg Ser Leu Pro Asp Glu Ser Thr Gly Asp Ile Ser Tyr Ala
        450                 455                 460

Gln Leu Gln Phe Ala Tyr Asp Thr Leu Arg Thr Tyr Ile Asn Gln Ala
465                 470                 475                 480

Leu Gly His Ile Ala Glu Ala Trp Cys Leu Asp Gln Lys Arg Thr Ala
                485                 490                 495

Glu Val Leu His Glu Leu Ser Lys Ile Asn Pro Ser Asn Ile Leu Ser
            500                 505                 510

Ala Ile Phe Gly Val Pro Val Ala Ala Arg Val Val Gly Asp Val Ile
            515                 520                 525

Ser Leu Ala Lys Cys Ile Glu Val Asn Gln Ser Thr Val Leu Ile Lys
        530                 535                 540

Gly Asp Met Arg Lys Phe Ser Asp Asp Gly Lys Leu Glu Gly Cys Tyr
545                 550                 555                 560

Ser Arg Pro Val Val Trp Phe Ser Met Lys Asn Ser Thr Glu Val Arg
                565                 570                 575

Leu Gly Gln Leu Gly Glu Asp Asn Glu Ile Leu Leu Gly Thr His Arg
            580                 585                 590

Met Glu Thr Cys Gln Thr Gln Asp Tyr Arg Ile Phe Val Ala Gly Asp
            595                 600                 605

Ile Gly Tyr Glu Phe Gln Gln Tyr Val Phe Thr Lys Lys Ile Asn Leu
            610                 615                 620

Ser Glu Ile Asp Ile Ile Asp Thr Met Ile Ala Leu Lys Thr Glu Pro
625                 630                 635                 640

Leu Glu Asn Ile Asp Phe Lys Val Leu Glu Leu Tyr Ser Arg Asp Glu
                645                 650                 655

Leu Ala Gln Ala Asn Val Phe Asp Leu Glu Ser Ile Met Arg Glu Tyr
            660                 665                 670

Asn Tyr Gln Lys Lys Arg Leu Asp Phe Val Val Glu Arg Val Ile Asn
            675                 680                 685

Pro Ile Pro Pro
        690

<210> SEQ ID NO 18
<211> LENGTH: 698
<212> TYPE: PRT
<213> ORGANISM: Guinea pig cytomegalovirus
<220> FEATURE:
<221> NAME/KEY: MISC_FEATURE
<222> LOCATION: (1)..(698)
<223> OTHER INFORMATION: GP75 ectodomain

<400> SEQUENCE: 18

Met Ser Pro Ala Thr Arg Phe Thr Val Ile Ser Cys Leu Val Val Ser
1               5                   10                  15

Leu Ile Thr Pro Ser Glu Thr Ser Ser Trp Phe Asp Pro Phe Ile Glu
            20                  25                  30

Trp Ala Arg Ser Ser Pro Asn Met Thr Cys Val Asn Asn Arg Thr Gly
        35                  40                  45
```

-continued

```
Thr Arg Ser Leu Ala Thr Glu Gly Leu Ile Ser Phe Asn Phe Tyr Glu
    50              55              60

Ala Ser Arg Thr Val Arg Thr Tyr Gln Val Pro Lys Cys Ile Phe Met
65              70              75              80

Ser Ser Val Ser Lys Thr Ile Met Gln Gly Val Asp Leu Phe Glu Ser
            85              90              95

Leu Glu Ser Tyr Arg Arg Arg Tyr Tyr Ser Tyr Ile Ile Val Pro Val
            100             105             110

His Ala Ser Phe Gln Ile Phe Ile His Asp Leu Arg Thr Asp Leu Ser
            115             120             125

Ser Pro Thr Glu Glu Leu Thr Ser Pro Val Asp Lys Thr Leu Pro Asn
    130             135             140

Val Thr Ile Trp His Thr Pro Ser Gly Tyr Val Ile Arg Leu Leu Asp
145             150             155             160

Val Val Thr Pro Arg Phe Glu Glu Cys Thr Leu Phe Pro Asn His Thr
                165             170             175

Val Ile Phe Asp Met Thr Val Pro Cys Ser Gln Glu Val Tyr Leu Arg
            180             185             190

Gln Thr Gly Lys His Gln Phe Ala Ile Val Leu Thr Phe Thr Pro Ser
            195             200             205

Phe Phe Val Leu Asn Ile Gln Thr Ala Gln His Gln His Val Thr Glu
    210             215             220

Asn Asp Glu Asp Val Ile Leu Ile Phe Gly Asp Val Arg Ser Ile Asp
225             230             235             240

Val Lys Ala Pro Tyr Ser Lys Pro Val Leu Thr Leu Arg Gln Ser Tyr
                245             250             255

Arg Asp Asp Leu Leu Ile Val Ala Lys Thr Ser Ile Val Asn Ala Thr
            260             265             270

Tyr Pro Phe Ile Lys Thr Gln Asp Phe Leu Lys Gly Thr Leu Ser Gly
            275             280             285

Asn Tyr Leu Asp Phe Asn His Val Tyr Thr Glu Phe Asn Arg Leu Val
    290             295             300

Ile His Asn Leu Val Glu Gly Leu Cys Asp Ala Pro Pro Asp Asp Arg
305             310             315             320

Thr Val Ser Met Val Phe Ser Tyr Ala Val Leu Ala Arg Thr Leu Tyr
            325             330             335

His Thr Ser Asn Val Thr Ala Arg Leu Glu Asp Val Ala Leu Arg Tyr
            340             345             350

Val Arg Leu Thr Leu Ala Arg Thr Phe Leu Gln Gln Cys Phe Asp Val
            355             360             365

Gly Pro Arg Tyr Met Arg Phe Pro Thr Ile Asp Gly Ala Leu Ser Val
    370             375             380

Leu Leu Lys Leu Ile Arg Asn Ser Arg Asp Val Asp Gly Gly Leu Lys
385             390             395             400

Leu Ser Leu Thr Phe Ala Leu Ile Phe Gly Asn Asn Thr Asp Met Thr
                405             410             415

Lys Glu Arg Asp Leu Glu Asn Ala Leu Tyr Glu Met Lys Ser Ile His
            420             425             430

Arg Ala Gly Leu Val Ser Pro Leu Ser Pro Arg Gln Arg Ser Leu Leu
            435             440             445

Tyr Met Met Ala Tyr Val Thr His His Thr Thr Ala Phe Pro Asp Ile
    450             455             460

Arg Arg Glu Met Leu Ala Met Gln Thr Ser Leu Cys Ser Pro Gln Glu
```

-continued

```
465                 470                 475                 480

Leu Tyr Asn Trp Ala Pro His Val Ser Ser Ala Gly Leu Thr Met Gln
                485                 490                 495

Glu Met Phe Thr Pro Cys Ser Gly Ser Gly Arg Arg Asp Tyr Ser Glu
                500                 505                 510

Ala Arg Ile Ala Glu Ile Val Gln Leu Asn Pro Leu Thr Thr Lys Thr
                515                 520                 525

Pro Ala Asp Leu Tyr Arg Ile Leu Ala His Phe Asp Arg Ser Asn Leu
                530                 535                 540

Thr Asn Phe Pro Ala Leu Ser Cys Ile Ser His Leu Ser Gly Tyr Val
545                 550                 555                 560

Ala Val Thr Leu Arg Asp Val Thr Tyr Val Val Ser Ser Asn Val Met
                565                 570                 575

Leu Lys Gly Thr Ser Tyr Pro Val Thr Asn Leu Ala Val Asp Lys Thr
                580                 585                 590

Met Ile Val Thr Val Ser Pro Ala Gln His Pro Cys Glu Lys Thr Glu
                595                 600                 605

Val Ala His Ala Thr Arg Ser Ile Pro Ile Val Lys Asn Ile Thr Ile
                610                 615                 620

Gly Asn Asp Cys Glu Tyr Cys Lys Ser Ala Ile Met Glu Tyr Asp Glu
625                 630                 635                 640

Val Asn Gly Leu Ser Asn Ile Val Tyr Leu Ala Asp Thr Ala Asp Leu
                645                 650                 655

Val Leu Val Thr Asn Leu Asp Asn Arg Ile Leu Ala Ser Ser Pro Arg
                660                 665                 670

Thr Arg Tyr Ile Met Met Thr Ala Asn Gly Thr Leu Met Glu Ile Thr
                675                 680                 685

Ser Val Ile Ile Asp Ile Arg Gln Thr Ser
    690                 695
```

```
<210> SEQ ID NO 19
<211> LENGTH: 24
<212> TYPE: PRT
<213> ORGANISM: Human cytomegalovirus
<220> FEATURE:
<221> NAME/KEY: MISC_FEATURE
<222> LOCATION: (1)..(24)
<223> OTHER INFORMATION: HCMV gB signal sequence

<400> SEQUENCE: 19

Met Glu Ser Arg Ile Trp Cys Leu Val Val Cys Val Asn Leu Cys Ile
1               5                   10                  15

Val Cys Leu Gly Ala Ala Val Ser
            20
```

```
<210> SEQ ID NO 20
<211> LENGTH: 9
<212> TYPE: PRT
<213> ORGANISM: Artificial Sequence
<220> FEATURE:
<223> OTHER INFORMATION: 9 amino acid linker

<400> SEQUENCE: 20

Gly Gly Gly Ser Gly Ser Gly Gly Gly
1               5
```

```
<210> SEQ ID NO 21
<211> LENGTH: 20
<212> TYPE: PRT
```

<213> ORGANISM: Homo sapiens
<220> FEATURE:
<221> NAME/KEY: MISC_FEATURE
<222> LOCATION: (1)..(20)
<223> OTHER INFORMATION: Immonoglobulin light chain signal peptide
      sequence

<400> SEQUENCE: 21

Met Arg Leu Pro Ala Gln Leu Leu Gly Leu Leu Met Leu Trp Val Pro
1               5                   10                  15

Gly Ser Ser Gly
            20

<210> SEQ ID NO 22
<211> LENGTH: 5
<212> TYPE: PRT
<213> ORGANISM: Artificial Sequence
<220> FEATURE:
<223> OTHER INFORMATION: 5 amino acids linker

<400> SEQUENCE: 22

Gly Gly Gly Gly Ser
1               5

<210> SEQ ID NO 23
<211> LENGTH: 15
<212> TYPE: PRT
<213> ORGANISM: Artificial Sequence
<220> FEATURE:
<223> OTHER INFORMATION: 15 amino acids linker

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 22
<212> TYPE: DNA
<213> ORGANISM: Artificial Sequence
<220> FEATURE:
<223> OTHER INFORMATION: GPCMV GP83 Forward Primer

<400> SEQUENCE: 24
cgacgacgac gatgacgaaa ac                                              22

<210> SEQ ID NO 25
<211> LENGTH: 22
<212> TYPE: DNA
<213> ORGANISM: Artificial Sequence
<220> FEATURE:
<223> OTHER INFORMATION: GPCMV GP83 Reverse Primer

<400> SEQUENCE: 25
tcctcggtct caacgaaggg tc                                              22

<210> SEQ ID NO 26
<211> LENGTH: 17
<212> TYPE: DNA
<213> ORGANISM: Artificial Sequence
<220> FEATURE:
<223> OTHER INFORMATION: GPCMV GP83 FAM Probe

<400> SEQUENCE: 26
atccgagtta ggcagcg                                                    17

<210> SEQ ID NO 27

-continued

```
<211> LENGTH: 17
<212> TYPE: DNA
<213> ORGANISM: Artificial Sequence
<220> FEATURE:
<223> OTHER INFORMATION: Guinea pigs beta-actin Forward Primer

<400> SEQUENCE: 27
tggatcggcg gctcatc                                                    17

<210> SEQ ID NO 28
<211> LENGTH: 22
<212> TYPE: DNA
<213> ORGANISM: Artificial Sequence
<220> FEATURE:
<223> OTHER INFORMATION: Guinea pigs beta-actin Reverse Primer

<400> SEQUENCE: 28
catcgtactc ctgcttgctg at                                              22

<210> SEQ ID NO 29
<211> LENGTH: 15
<212> TYPE: DNA
<213> ORGANISM: Artificial Sequence
<220> FEATURE:
<223> OTHER INFORMATION: Guinea pigs beta-actin Probe

<400> SEQUENCE: 29
cactctccac cttcc                                                      15

<210> SEQ ID NO 30
<211> LENGTH: 9
<212> TYPE: PRT
<213> ORGANISM: Artificial Sequence
<220> FEATURE:
<223> OTHER INFORMATION: His tag

<400> SEQUENCE: 30

Leu Gly Gly His His His His His His
1               5

<210> SEQ ID NO 31
<211> LENGTH: 671
<212> TYPE: PRT
<213> ORGANISM: Human cytomegalovirus
<220> FEATURE:
<221> NAME/KEY: MISC_FEATURE
<222> LOCATION: (1)..(671)
<223> OTHER INFORMATION: gBVC37

<400> SEQUENCE: 31

Ser Ser Ser Thr Ser His Ala Thr Ser Ser Thr His Asn Gly Ser His
1               5                   10                  15

Thr Ser Arg Thr Thr Ser Ala Gln Thr Arg Ser Val Tyr Ser Gln His
            20                  25                  30

Val Thr Ser Ser Glu Ala Val Ser His Arg Ala Asn Glu Thr Ile Tyr
        35                  40                  45

Asn Thr Thr Leu Lys Tyr Gly Asp Val Val Gly Val Asn Thr Thr Lys
    50                  55                  60

Tyr Pro Tyr Arg Val Cys Ser Met Ala Gln Gly Thr Asn Leu Thr Arg
65                  70                  75                  80

Phe Glu Arg Asn Ile Ile Cys Thr Ser Met Lys Pro Ile Asn Glu Asp
                85                  90                  95

Leu Asp Glu Gly Ile Met Val Val Tyr Lys Arg Asn Ile Val Ala His
            100                 105                 110
```

```
Thr Phe Lys Val Arg Val Tyr Gln Lys Val Leu Thr Phe Arg Arg Gly
        115                 120                 125

Gly Gly Gly Ser Asn Thr Glu Tyr Val Ala Pro Pro Met Trp Glu Ile
    130                 135                 140

His His Ile Asn Lys Phe Ala Gln Cys Tyr Ser Ser Tyr Ser Arg Val
145                 150                 155                 160

Ile Gly Gly Thr Val Phe Val Ala Tyr His Arg Asp Ser Tyr Glu Asn
                165                 170                 175

Lys Thr Met Gln Leu Ile Pro Asp Asp Tyr Ser Asn Thr His Ser Thr
                180                 185                 190

Arg Tyr Val Thr Val Lys Asp Gln Trp His Ser Arg Gly Ser Glu Arg
                195                 200                 205

Glu Thr Cys Asn Leu Asn Cys Met Leu Thr Ile Thr Thr Ala Arg Ser
    210                 215                 220

Lys Tyr Pro Tyr His Phe Phe Ala Thr Ser Thr Gly Asp Val Val Tyr
225                 230                 235                 240

Ile Ser Pro Phe Tyr Asn Gly Thr Asn Arg Asn Ala Ser Tyr Phe Gly
                245                 250                 255

Glu Asn Ala Asp Lys Phe Phe Ile Phe Pro Asn Tyr Thr Ile Val Ser
                260                 265                 270

Asp Phe Gly Arg Pro Asn Ala Ala Pro Glu Thr His Arg Leu Val Ala
                275                 280                 285

Phe Leu Glu Arg Ala Asp Ser Val Ile Ser Trp Asp Ile Gln Asp Glu
    290                 295                 300

Lys Asn Val Thr Cys Gln Leu Thr Phe Trp Glu Ala Ser Glu Arg Thr
305                 310                 315                 320

Ile Arg Ser Glu Ala Glu Asp Ser Tyr His Phe Ser Ser Ala Lys Met
                325                 330                 335

Thr Ala Thr Phe Leu Ser Lys Lys Gln Glu Val Asn Met Ser Asp Ser
                340                 345                 350

Ala Leu Asp Cys Val Arg Asp Glu Ala Ile Asn Lys Leu Gln Gln Ile
    355                 360                 365

Phe Asn Thr Ser Tyr Asn Gln Thr Tyr Glu Lys Tyr Gly Asn Val Ser
    370                 375                 380

Val Phe Glu Thr Ser Gly Gly Leu Val Val Phe Trp Gln Gly Ile Lys
385                 390                 395                 400

Gln Lys Ser Leu Val Glu Leu Glu Arg Leu Ala Asn Arg Ser Ser Leu
                405                 410                 415

Asn Ile Thr His Thr Thr Gln Arg Ser Thr Ser Asp Asn Asn Thr Thr
                420                 425                 430

His Leu Ser Ser Met Glu Ser Val His Asn Leu Val Tyr Ala Gln Leu
    435                 440                 445

Gln Phe Thr Tyr Asp Thr Leu Arg Gly Tyr Ile Asn Arg Ala Leu Ala
    450                 455                 460

Gln Ile Ala Glu Ala Trp Cys Val Asp Gln Arg Arg Thr Leu Glu Val
465                 470                 475                 480

Phe Lys Glu Leu Ser Lys Ile Asn Pro Ser Ala Ile Leu Ser Ala Ile
                485                 490                 495

Tyr Asn Lys Pro Ile Ala Ala Arg Phe Met Gly Asp Val Leu Gly Leu
                500                 505                 510

Ala Ser Cys Val Thr Ile Asn Gln Thr Ser Val Lys Val Leu Arg Asp
    515                 520                 525
```

-continued

```
Met Asn Val Lys Asn Ser Thr Gly Arg Cys Tyr Ser Arg Pro Val Val
    530             535             540

Ile Phe Asn Phe Ala Asn Ser Ser Tyr Val Gln Tyr Gly Gln Leu Gly
545             550             555             560

Glu Asp Asn Glu Ile Leu Leu Gly Asn His Arg Thr Glu Glu Cys Gln
            565             570             575

Asn Gly Ser Leu Lys Ile Phe Ile Ala Gly Asn Ser Ala Tyr Glu Tyr
            580             585             590

Val Asp Tyr Leu Phe Asn Thr Thr Ile Asp Leu Ser Ser Ile Ser Thr
            595             600             605

Val Asp Ser Met Ile Ala Leu Asp Ile Asp Pro Leu Glu Asn Thr Asp
            610             615             620

Phe Arg Val Leu Glu Leu Tyr Ser Gln Lys Glu Leu Arg Ser Ser Asn
625             630             635             640

Val Phe Asp Leu Glu Glu Ile Met Arg Glu Phe Asn Ser Tyr Lys Gln
            645             650             655

Arg Val Lys Tyr Val Glu Asp Lys Val Val Asp Pro Leu Pro Pro
            660             665             670

<210> SEQ ID NO 32
<211> LENGTH: 435
<212> TYPE: PRT
<213> ORGANISM: Guinea pig cytomegalovirus
<220> FEATURE:
<221> NAME/KEY: MISC_FEATURE
<222> LOCATION: (1)..(435)
<223> OTHER INFORMATION: GPCMV-gB delta d4

<400> SEQUENCE: 32

Glu Glu Gly Ile Met Leu Ile Tyr Lys Arg Asn Ile Leu Pro Tyr Val
1               5               10              15

Phe Thr Ala Tyr Thr Tyr Gln Lys Glu Leu Leu Phe Gln Arg Ser Tyr
            20              25              30

Lys Gly His Arg Tyr Asp Tyr Leu Leu Gly Tyr Ser Arg Glu Phe Val
            35              40              45

Ala Leu Pro Met Trp Glu Ile Phe Leu Val Asn Ser Arg Gly Gln Cys
    50              55              60

Tyr Thr Ser His Gln Arg Val Ile Gly Ala Asp Arg Tyr Ile Ala Tyr
65              70              75              80

His Asn Asp Asn Glu Val Asn Glu Thr Met Trp Leu Met Arg Asp Asp
            85              90              95

Met Gly Asn Asp Asp Thr Tyr Arg Tyr Ile Thr Val Lys Glu His Ala
            100             105             110

Arg Thr Pro Gly Ser Val Ala Phe His Lys Glu Thr Cys Ser Met Asn
            115             120             125

Cys Ile Val Thr Lys Thr Lys Gly Lys Ser Lys Phe Pro Tyr Asp Met
    130             135             140

Phe Val Leu Pro Ser Gly Val Ile Val Asn Ile Ser Pro Phe Tyr Asn
145             150             155             160

Gly Ser Asn Gly Lys Thr Phe Arg Glu Gln Arg Glu Lys Phe His Ile
            165             170             175

Trp Ser Asn Tyr Ser Ile Leu Lys Asp Phe Gly Ser Arg Ala Leu Glu
            180             185             190

Ala Arg Ile Val Pro Lys Met Ala Phe Tyr Glu Arg Glu Asp Val Val
            195             200             205

Ile Gly Trp Glu Val Asn Asp Gln Ser Asn Val Thr Cys Glu Met Ile
```

-continued

```
       210               215               220

Leu Trp Glu Thr Val Asp Arg Ala Ile Arg Thr Glu Tyr Glu Asn Ala
225                     230               235               240

Phe His Tyr Val Ala Arg Thr Leu Thr Ser Thr Phe Val Glu Asn Lys
                245               250               255

Tyr Ser Pro Asp Asn Asn Leu Thr Glu Asp Asp Ile Lys Cys Phe Lys
            260               265               270

Asn Asp Ala Gln Lys Lys Ile Glu Glu Val Phe Leu Arg Asp Tyr Asn
        275               280               285

Glu Thr Tyr Asp Met Asp Gly Asn Ala Thr Tyr His Val Thr Thr Gly
    290               295               300

Gly Leu Val Ile Val Trp Gln Gly Leu Lys Gln Lys Ser Leu Lys Ala
305               310               315               320

Leu Glu Ile Ala Ala Asn Glu Ser Ala Val Ser Ala Thr Gly Ser Asn
            325               330               335

Ser Arg Arg Lys Arg Ser Leu Pro Asp Glu Ser Thr Gly Asp Ile Ser
            340               345               350

Tyr Ala Gln Leu Gln Phe Ala Tyr Asp Thr Leu Arg Thr Gly Gly Gly
        355               360               365

Ser Gly Ser Gly Gly Gly Leu Glu Asn Ile Asp Phe Lys Val Leu Glu
    370               375               380

Leu Tyr Ser Arg Asp Glu Leu Ala Gln Ala Asn Val Phe Asp Leu Glu
385               390               395               400

Ser Ile Met Arg Glu Tyr Asn Tyr Gln Lys Lys Arg Leu Asp Phe Val
            405               410               415

Val Glu Arg Val Ile Asn Pro Ile Pro Pro Leu Gly Gly His His His
            420               425               430

His His His
        435
```